(12) United States Patent
Glimcher et al.

(10) Patent No.: US 7,615,380 B2
(45) Date of Patent: Nov. 10, 2009

(54) METHODS FOR MODULATING AN IMMUNE RESPONSE BY MODULATING KRC ACTIVITY

(75) Inventors: Laurie H. Glimcher, West Newton, MA (US); Mohamed Oukka, Brighton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 254 days.

(21) Appl. No.: 10/701,401

(22) Filed: Nov. 3, 2003

(65) Prior Publication Data

US 2005/0026285 A1     Feb. 3, 2005

Related U.S. Application Data

(63) Continuation-in-part of application No. PCT/US02/14166, filed on May 3, 2002.

(60) Provisional application No. 60/288,369, filed on May 3, 2001.

(51) Int. Cl.
| | |
|---|---|
| G01N 33/566 | (2006.01) |
| G01N 33/536 | (2006.01) |
| G01N 33/48 | (2006.01) |
| C12N 15/12 | (2006.01) |
| C12R 1/00 | (2006.01) |
| C12Q 1/00 | (2006.01) |

(52) U.S. Cl. .......................... 436/501; 436/63; 436/86; 436/536

(58) Field of Classification Search ........................ None
See application file for complete search history.

(56) References Cited

FOREIGN PATENT DOCUMENTS

WO     WO-2004/060304 A2     7/2004

OTHER PUBLICATIONS

Guo et al, Proc Natl Acad Sci 101(25):9205-9210, 2004.*
Hult and Berglund, Curr Opin Biotechnol 14:395-400, 2003.*
Kuroiwa et al, Nature Genetics 36(7):775-80, 2004.*
Moreadith et al, J. Mol. Med. 75(3): 208-216, 1997*
Polejaeva et al, Theriogenology, 53(1):117-126, 2000.*
Rulicke et al, Experimental Physiology 85: 589-601, 2000.*
Bishop, Reprod. Nutr. Dev. 36: 607-618, 1998.*
Mullins et al, Journal of Clinical Investigation 97(7): 1557-1560, 1996.*
Houdebine, J. Biotech. 34: 269-287, 1994.*
Pearson, Nature 415(6867):8-9, 2002.*
Mullins et al, Hypertension 22: 630-633, 1993.*
Denning, Nat. Biotech. 19:559-562, 2001.*
Humpherys et al, Science 293:95-97, 2001.*
Wall et al, J Dairy Sci. 80:2213-2224, 1997.*
Yanagimachi, Mol. Cell Endocrinol. 187:241-248, 2002.*
Kappel et al, Current Opinion in Biotechnology 3: 548-553, 1992.*
Wall, Theriogenology 45: 57-68, 1996.*
Cameron, Molec. Biotech. 7: 253-265, 1997.*
Sigmund, Arterioscler. Throm. Vasc. Biol. 20: 1425-1429, 2000.*
Anders and Schlondorff, Exp. Nephrol. 8: 181-193, 2000.*
Schalkwyk et al, Genes Brain Behav, 6:299-303, 2007.*
Gerlai, Trends Neurosci, 19: 177-181, 1996.*
Deonarain, Expert Opin. Ther. Pat. 8: 53-69, 1998.*
Verma and Somia, Nature 389: 239-242, 1997.*
Eck et al, Goodman & Gilman's The Pharmacological Basis of Therapeutics, McGraw-Hill, New York, NY., pp. 77-101, 1996.*
Gorecki, Expert Opin. Emerging Drugs 6(2): 187-98, 2001.*
Cleland et al, Current Opinion in Biotechnology 12: 212-219, 2001.*
Rudinger, in J.A. Parsons, ed. "Peptide hormones", University Park Press, 1976.*
Ngo et al., In Merz et al., ed. "The protein folding problem and tertiary structure prediction", Birkhauser, 1994.*
Wells, Biochemistry 29:8509-8517, 1990.*
Skolnick et al, Trends in Biotech. 18:34-39, 2000.*
Bork, Genome Research 10:398-400, 2000.*
Doerks et al, Trends in Genetics 14:248-250, 1998.*
Smith et al, Nature Biotechnology 15:1222-1223, 1997.*
Affolter, et al., "Nuclear interpretation of Dpp signaling in Drosophila," *EMBO J.,* vol. 20(13):3298-305 (2001).
Allen, et al., "The kappa B transcriptional enhancer motif and signal sequences of V(D)J recombination are targets for the zinc finger protein HIVEP3/KRC: a site selection amplification binding study," *BMC Immunol.,* vol. 22;3(1):10 (2002).
Allen, et al., "Downregulation of KRC induces proliferation, anchorage independence, and mitotic cell death in HeLa cells," *Exp Cell Res.,* vol. 260(2):346-56 (2000).
Allen, et al., "Developmental anomalies and neoplasia in animals and cells deficient in the large zinc finger protein KRC," *Genes Chromosomes Cancer,* vol. 35(4):287-98 (2002).
Allen, Carl E. et al., "KRC controls cell growth by regulating the transcription of c-myc," Presented at the American Society of Biochemistry and Molecular Biology Annual Meeting, Washington, D.C., p. A1391, Abstract No. 473 (1998).
Angel P. et al., "Phorbol ester-inducible genes contain a common cis element recognized by a TPA-modulated trans-acting factor," *Cell,* vol. 49(6):729-39 (1987).

(Continued)

*Primary Examiner*—Q. Janice Li
*Assistant Examiner*—Kevin K. Hill
(74) *Attorney, Agent, or Firm*—Megan E. Williams, Esq.; Lahive & Cockfield, LLP

(57) ABSTRACT

This invention demonstrates that KRC molecules have multiple important functions as modulating agents in regulating a wide variety of cellular processes including: inhibiting NFkB transactivation, increasing TNF-alpha induced apoptosis, inhibiting JNK activation, inhibiting endogenous TNF-alpha expression, promoting immune cell proliferation and immune cell activation (e.g., in Th1 cells), activating IL-2 expression e.g., by activating the AP-1 transcription factor, and increasing actin polymerization. The present invention also demonstrates that KRC interacts with TRAF. Furthermore, the present invention demonstrates that KRC physically interacts with the c-Jun component of AP-1 to control its degradation Methods for identifying modulators of KRC activity are provided. Methods for modulating an immune response using agents that modulate KRC activity are also provided.

28 Claims, 23 Drawing Sheets

OTHER PUBLICATIONS

Arch, et al., "Tumor necrosis factor receptor-associated factors (TRAFs)—a family of adapter proteins that regulates life and death," *Genes Dev.*, vol. 12(18):2821-30 (1998).

Arias, et al., "Activation of cAMP and mitogen responsive genes relies on a common nuclear factor," *Nature*, vol. 370(6486):226-9 (1994).

Arora, et al., "The Drosophila schnurri gene acts in the Dpp/TGF beta signaling pathway and encodes a transcription factor homologous to the human MBP family," *Cell*, vol. 81(5)781-90 (1995).

Bachmeyer, et al., "Regulation by phosphorylation of the zinc finger protein KRC that binds the kappaB motif and V(D)J recombination signal sequences," *Nucleic Acids Res.*, vol. 27(2):643-8 (1999).

Behre, et al., "C-Jun is a JNK-independent coactivator of the PU.1 transcription factor," *J. Biol. Chem.*, vol. 274(8):4939-46 (1999).

Berhrens, et al., "Jun N-terminal kinase 2 modulates thymocyte apoptosis and T cell activation through c-Jun and nuclear factor of activated T cell (NF-AT)," *Proc. Natl. Acad. Sci. USA*, vol. 98(4):1769-74 (2001).

Bianchi, et al., "Integrin LFA-1 interacts with the transcriptional co-activator JAB1 to modulate AP-1 activity," *Nature*, vol. 404(6778):617-21 (2000).

Binetruy, et al., "Ha-Ras augments c-Jun activity and stimulates phosphorylation of its activation domain," *Nature*, vol. 351(6322):122-7 (1991).

Borden, et al., "The solution structure of the RING finger domain from the acute promyelocytic leukaemia proto-oncoprotein PML," *EMBO J.*, vol. 14(7):1532-41 (1995).

Cao, et al., "TRAF6 is a signal transducer for interleukin-1," Nature, vol. 383(6599):443-6 (1996).

Castellanos, et al., "Expressions of the leukocyte early activation antigen CD69 is regulated by the transcription factor AP-1," *J. Immunol.*, vol. 159(11)5463-73 (1997).

Claret, et al., "A new group of conserved coactivators that increase the specificity of AP-1 transcription factors," *Nature*, vol. 383(6599):453-7 (1996).

Cohn, et al., "Characterization of Sp1, AP-1, CBF and KRC binding sites and minisatellite DNA as functional elements of the metastasis-associated mts1/S100A4 gene intronic enhancer," *Nucleic Acids Res.*, vol. 29(16):3335-46 (2001).

Dai, et al., "The zinc finger protein schnurri acts as a Smad partner in mediating the transcriptional response to decapentaplegic," *Dev. Biol.*, vol. 227(2):373-87 (2000).

Deng, et al., "c-Fos transcriptional activity stimulated by H-Ras-activated protein kinase distinct from JNK and ERK," *Nature*, vol. 371(6493):171-5 (1994).

Dong, et al., "JNK is required for effector T-cell function but not for T-cell activation." *Nature*, vol. 405(6782):91-4 (2000).

Dumitru, et al., "TNF-alpha induction by LPS is regulated post-transcriptionally via a Tpl2/ERK-dependent pathway," *Cell*, vol. 103(7):1071-83 (2000).

Durand, et al., "A 275 basepair fragment at the 5' end of the interleukin 2 gene enhances expression from a heterologous promoter in response to signals from the T cell antigen receptor," *J. Exp. Med.*, vol. 165(2):395-407 (1987).

Ghosh, et al., "NF-KappaB and Rel Proteins: Evolutionarily conserved mediators of immune responses," Annu. Rev. Immunol., vol. 16:226-260 (1998).

Grieder, et al., "Schnurri is required for Drosophila Dpp signaling and encodes a zinc finger protein similar to the mammalian transcription factor PRDII-BF1,"*Cell*, vol. 81(5):791-800 (1995).

Hicar, et al., "Embryonic expression and regulation of the large zinc finger protein KRC," *Genesis*, vol. 33(1):8-20 (2002).

Hicar, et al., "Structure of the human zinc finger protein HIVEP3: molecular cloning, expression, exon-intron structure, and comparison with paralogous genes HIVEP1 and HIVEP2," *Genomics*, vol. 71(1):89-100 (2001).

Himes, et al., "High mobility group protein I(Y) is required for function and for c-Rel binding to CD28 response elements within the GM-CSF and IL-2 promoters," Immunity, vol. 5(5):479-89 (1996).

Hjelmsoe, et al., "The kappaB and V(D)J recombination signal sequence binding protein KRC regulates transcription of the mouse metastasis-associated gene S100A4/mts1," *J. Biol. Chem.*, vol. 275(2):913-20 (2000).

Ip, et al., "Signal transduction by the c-Jun N-terminal kinase (JNK)—from inflammation to development," *Curr. Opin. Cell Biol.*, vol. 10(2):205-19 (1998).

Isakov, et al., "Protein kinase C(theta) in T cell activation," *Annu. Rev. Immunol.*, vol. 20:761-94 (2002).

Jain, et al., "Transcriptional regulation of the IL-2 gene," *Curr. Opin. Immunol.*, vol. 7(3):333-42 (1995).

Jain, et al., "Nuclear factor of activated T cells contains Fos and Jun," *Nature*, vol. 356(6372):801-4 (1992).

Jochum, et al., "AP-1 in mouse development and tumorigenesis," *Oncogene*, vol. 20(19):2401-12 (2001).

Kamei, et al,. "A CBP integrator complex mediates transcriptional activation and AP-1 inhibition by nuclear receptors," *Cell*, vol. 85(3):403-14 (1996).

Karin M., "The NF-kappa B activation pathway: its regulation and role in inflammation and cell survival," *Cancer J. Sci. Am.*, vol. 4 Suppl 1:S92-9 (1998).

Karin, et al., "AP-1 function and regulation," *Curr. Opin. Cell Biol.*, vol. 9(2):240-6 (1997).

Lee, et al., "TRAF2 is essential for JNK but not NF-kappaB activation and regulates lymphocyte proliferation and survival," *Immunity*, vol. 7(5):703-13 (1997).

Lee, et al., "Steroid receptor coactivator-1 coactivates activating protein-1-mediated transactivations through interaction with the c-Jun and c-Fos subunits," *J. Biol. Chem.*, vol. 273(27):16651-4 (1998).

Lee, et al., "Activating protein-1, nuclear factor-kappaB, and serum response factor as novel target molecules of the cancer-amplified transcription coactivator ASC-2," *Mol. Endocrinol.*, vol. 14(6):915-25 (2000).

Leppa, et al., "Diverse functions of JNK signaling and c-Jun in stress response and apoptosis," *Oncogene*, vol. 18(45):6158-62 (1999).

Liberati, et al., "Smads bind directly to the Jun family of AP-1 transcription factors," *Proc. Natl. Acad. Sci. USA*, vol. 96(9):4844-9 (1999).

Lindsten, et al., "Regulation of lymphokine messenger RNA stability by a surface-mediated T cell activation pathway," *Science*, vol. 244(4902):339-43 (1989).

Macian, et al., "Transcriptional mechanisms underlying lymphocyte tolerance," *Cell*, vol. 109(6):719-31 (2002).

Mak, et al., "The V(D)J recombination signal sequence and kappa B binding protein Rc binds DNA as dimers and forms multimeric structures with its DNA ligands," *Nucleic Acids Res.*, vol. 22(3):383-90 (1994).

Mak, et al., "KRC transcripts: identification of an unusual alternative splicing event," *Immunogenetics*, vol. 48(1):32-9 (1998).

Matunis, et al., "Punt and schnurri regulate a somatically derived signal that restricts proliferation of committed progenitors in the germline," *Development*, vol. 124(21):4383-91 (1997).

Mondino, et al., "Defective transcription of the IL-2 gene is associated with impaired expression of c-Fos, FosB, and JunB in anergic T helper 1 cells," *J. Immunol.*, vol. 157(5):2048-57 (1996).

Moreau, et al., "Bone-specific expression of the alpha chain of the nascent polypeptide-associated complex, a coactivator potentiating c-Jun-mediated transcription," *Mol. Cell Biol.*, vol. 18(3):1312-21 (1998).

Murphy, et al., "Molecular interpretation of ERK signal duration by immediate early gene products," *Nat. Cell Biol.*, vol. 4(8):566-64 (2002).

Nakano, et al., "TRAF5, an activator of NF-kappaB and putative signal transducer for the lymphotoxin-beta receptor," *J. Biol. Chem.*, vol. 271(25):14661-4 (1996).

Oukka, et al., "A mammalian homolog of Drosophila schnurri, KRC, regulates TNF receptor-driven responses and interacts with TRAF2," *Mol. Cell.*, vol. 9(1):121-31 (2002).

Pessah, et al., "C-Jun associates with the oncoprotein Ski and suppresses Smad2 transcriptional activity," *J. Biol. Chem.*, vol. 277(32):29094-100 (2002).

Rayter, et al., "p21ras mediates control if IL-2 gene promoter function in T cell activation," *EMBO J.*, vol. 11(12):4549-56 (1992).

Rooney, et al., "Coordinate and cooperative roles for NF-AT and AP-1 in the regulation of the murine IL-4 gene," *Immunity*, vol. 2(5):473-83 (1995).

Rothe, et al., "A novel family of putative signal transducers associated with the cytoplasmic domain of the 75 kDa tumor necrosis factor receptor," *Cell*, vol. 78(4):681-92 (1994).

Staehling-Hampton, et al., "A Drosophila protein related to the human zinc finger transcription factor PRDII/MBPI/HIV-EP1 is required for dpp signaling," *Development*, vol. 121(10):3393-403 (1995).

Sun, et al., "PKC-theta is required for TCR-induced NF-kappaB activation in mature but not immature T lymphocytes," *Nature*, vol. 404(6776):402-7 (2000).

Szabo, et al., "A novel transcription factor, T-bet, directs Th1 lineage commitment," *Cell*, vol. 100(6):655-69 (2000).

Takagi, et al., "Murine Schnurri-2 is required for positive selection of thymocytes," *Nat. Immunol.*, vol. 2(11):1048-53 (2001).

Torres-Vazquez, et al., "The transcription factor Schnurri plays a dual role in mediating Dpp signaling during embryogenesis," *Development*, vol. 128(9):1657-70 (2001).

Torres-Vazquez, et al., "Schnurri is required for dpp-dependent patterning of the Drosophila wing," *Dev. Biol.*, vol. 227(2):388-402 (2000).

Udagawa, et al., "Schnurri interacts with Mad in a Dpp-dependent manner," *Genes Cells*, vol. 5(5):359-69 (2000).

Ullman, et al., "Jun family members are controlled by a calcium-regulated, cyclosporin A-sensitive signaling pathway in activated T lymphocytes," *Genes Dev.*, vol. 7(2):188-96 (1993).

Wajant, et al., "TNF receptor associated factors in cytokine signalling," *Cytokine Growth Factor Rev.*, vol. 10(1):15-26 (1999).

Wallach, et al., "Tumor necrosis factor receptor and Fas signaling mechanisms," *Annu. Rev. Immunol.*, vol. 17:331-67 (1999).

Weiss, et al., "Regulation of c-Jun NH(2)-terminal kinase (Jnk) gene expression during T cell activation," *J. Exp. Med.*, vol. 191(1):139-46 (2000).

Wu, et al., "1EX-1L, an apoptosis inhibitor involved in NF-kappaB-mediated cell survival," *Science*, vol. 281(5379):998-1001 (1998).

Wu, et al., "The mouse DNA binding protein Rc for the kappa B motif of transcription and for the V(D)J recombination signal sequences contains composite DNA-protein interaction domains and belongs to a new family of large transcriptional proteins," *Genomics*, vol. 35(3):415-24 (1996).

Wu, "ZAS: C2H2 zinc finger proteins involved in growth and development," *Gene Expr.*, vol. 10(4):137-52 (2002).

Wu, et al., "The DNA-binding ability of HIVEP3/KRC decreases upon activation of V(D)J recombination," *Immunogenetics*, vol. 53(7):564-71 (2001).

Yeh, et al., "Early lethality, functional NF-kappaB activation, and increased sensitivity to TNF-induced cell death in TRAF2-deficient mice," *Immunity*, vol. 7(5):715-25 (1997).

Zhang, et al., "Smad3 and Smad4 cooperate with c-Jun/c-Fos to mediate TGF-beta-induced transcription," *Nature*, vol. 394(6696):909-13 (1998).

International Preliminary Report on Patentability for Application No. PCT/US2004/036641, dated May 18, 2006.

Glimcher, Laurie H. et al., "Control of Postnatal Bone Mass by the Zinc Finger Adapter Protein Schnurri-3," *Ann. N.Y. Acad. Sci.*, vol. 1116:174-181 (2007).

Jones, Dallas C. et al., "Regulation of Adult Bone Mass by the Zinc Finger Adapter Protein Schnurri-3," *Science*, vol. 312:1223-1227 (2006).

Jones, Dallas C. et al., "Schnurri-3: A Key Regulator of Postnatal Skeletal Remodeling," *Adv. Exp. Med. Biol.*, Osteoimmunology, Interactions of the Immune and Skeletal Systems, Yongwon Choi, Ed., Springer, vol. 602, Chapter 1, pp. 1-13 (2007).

Jones, Dallas C. et al., "Schnurri-3 is an essential regulator of osteoblast function and adult bone mass," *Ann. Rheum. Dis*, vol. 66(Suppl III):iii49-iii51 (2007).

Oukka, Mohamed et al., "*Schnurri-3* (KRC) Interacts with c-Jun to Regulate the IL-2 Gene in T Cells," *J. Exp. Med.*, vol. 199(1):15-24 (2004).

Affolter, et al. Nuclear interpretation of Dpp signaling in Drosophila. EMBO J. Jul. 2,2001;20(13):3298-305.

Allen, et al. The kappa B transcriptional enhancer motif and signal sequences of V(D)J recombination are targets for the zinc finger protein HIVEP3/KRC: a site selection amplification binding study. BMC Immunol. Aug. 22, 2002;3(1):10.

Allen, et al. Downregulation of KRC induces proliferation, anchorage independence, and mitotic cell death in HeLa cells. Exp Cell Res. Nov. 1, 2000;260(2):346-56.

Allen, et al. Developmental anomalies and neoplasia in animals and cells deficient in the large zinc finger protein KRC. Genes Chromosomes Cancer. Dec. 2002;35(4):287-98.

Allen, et al. KRC Controls Cell Growth by Regulating the Transcription of c-Myc. Mechanisms of Transcription Control, p. A1391, Abstract No. 473, April, 1998.

Angel P, et al. Phorbol ester-inducible genes contain a common cis element recognized by a TPA-modulated trans-acting factor. Cell. Jun. 19, 1987;49(6):729-39.

Arch, et al. Tumor necrosis factor receptor-associated factors (TRAFs)—a family of adapter proteins that regulates life and death. Genes Dev. Sep. 15, 1998;12(18):2821-30.

Arias, et al. Activation of cAMP and mitogen responsive genes relies on a common nuclear factor. Nature, Jul. 21, 1994;307(6486):226-9.

Arora, et al. The Drosophila schnurri gene acts in the Dpp/TGF beta signaling pathway and encodes a transcription factor homologous to the human MBP family. Cell. Jun. 2, 1995;81(5):781-90.

Bachmeyer, et al. Regulation by phosphorylation of the zinc finger protein KRC that binds the kappaB motif and V(D)J recombination signal sequences. Nucleic Acids Res. Jan. 15, 1999;27(2)643-8.

Behre, et al. C-Jun is a JNK-independent coactivator of the PU.1 transcription factor. J. Biol Chem. Feb. 19, 1999;274(8):4939-46.

Behrens, et al. Jun N-terminal kinase 2 modulates thymocyte apoptosis and T cell activation through c-Jun and nuclear factor of activated T cell (NF-AT). Proc Natl Acad Sci U S A. Feb. 13, 2001;98(4):1769-74.

Bianchi, et al. Integrin LFA-1 interacts with the transcriptional co-activator JAB1 to modulate AP-1 activity. Nature. Apr. 6, 2000;404(6778):617-21.

Binetruy, et al. Ha-Ras augments c-Jun activity and stimulates phosphorylation of its activation domain. Nature. May 9, 1991;351(6322):122-7.

Borden, et al. The solution structure of the RING finger domain from the acute promyelocytic leukaemia proto-oncoprotein PML. EMBO J. Apr. 3, 1995;14(7):1532-41.

Cao, et al. TRAF6 is a signal transducer for interleukin-1. Nature. Oct. 3, 1996;383(6599):443-6.

Castellanos, et al. Expression of the leukocyte early activation antigen CD69 is regulated by the transcription factor AP-1. J Immunol. Dec. 1, 1997;159(11):5463-73.

Claret, et al. A new group of conserved coactivators that increase the specificity of AP-1 transcription factors. Nature. Oct. 3, 1996;383(6599):453-7.

Cohn, et al. Characterization of Sp1, AP-1, CBF and KRC binding sites and minisatellite DNA as functional elements of the metastasis-associated mts1/S100A4 gene intronic enhancer. Nucleic Acids Res. Aug. 15, 2001;29(16):3335-46.

Dia, et al. The zinc finger protein schnurri acts as a Smad partner in mediating the transcriptional response to decapentaplegic. Dev Biol. Nov. 15, 2000;227(2)378-87.

Deng, et al. c-Fos transcriptional activity stimulated by H-Ras-activated protein kinase distinct from JNK and ERK. Nature. Sep. 8, 1994;371(6493):171-5.

Dong, et al. JNK is required for effector T-cell function but not for T-cell activation. Nature. May 4, 2000;405(6782):91-4.

Dumitru, et al. TNF-alpha induction by LPS is regulated post-transcriptionally via a Tpl2/ERK-dependent pathway. Cell. Dec. 22, 2000;103(7)1071-83.

Durand, et al. A 275 basepair fragment at the 5' end of the interleukin 2 gene enhances expression from a heterologous promoter in response to signals from the T cell antigen receptor. J Exp Med. Feb. 1, 1987;165(2):395-407.

Ghosh, et al. NF-KappaB and Rel Proteins: Evolutionarily conserved mediators of immune responses. Annu Rev Immunol. 1998. 16:226-260.

Grieder, et al. Schnurri is required for Drosophila Dpp signaling and encodes a zinc finger protein similar to the mammalian transcription factor PRDII-BF1. Cell. Jun. 2, 1995;81(5):791-800.

Hicar, et al. Embryonic expression and regulation of the large zinc finger protein KRC. Genesis. May 2002;33(1):8-20.

Hicar, et al. Structure of the human zinc finger HIVEP3: molecular cloning, expression, exon-intron structure, and comparison with paralogous genes HIVEP1 and HIVEP2. Genomics. Jan. 1, 2001;71(1):89-100.

Himes, et al. High mobility group protein I(Y) is required for function and for c-Rel binding to CD28 response elements within GM-CSF and IL-2 promoters. Immunity. Nov. 1996;5(5):479-89.

Hjelmsoe, et al. The kappaB and V(D)J recombination signal sequence binding protein KRC regulates transcription of the mouse metastasis-associated gene S100A4/mts1. J Biol Chem. Jan. 14, 2000;275(2):913-20.

Ip, et al. Signal transduction by the c-Jun N-terminal kinase (JNK)—from inflammation to development. Curr Opin Cell Biol. Apr. 1998;10(2):205-19.

Isakov, et al. Protein kinase C(theta) in T cell activation. Annu Rev Immunol. 2002;20:761.94.

Jain, et al. Transcriptional regulation of the IL-2 gene. Curr Opin Immunol. Jun. 1995;7(3):333-42.

Jain, et al. Nuclear factor of activated T cells contains Fos and Jun. Nature. Apr. 30, 1992;356(6372):801-4.

Jochum, et al. AP-1 in mouse development and tumorigenesis. Oncogene. Apr. 30, 2001;20(19):2401-12.

Kamei, et al. A CBP integrator complex mediates transcriptional activation and AP-1 inhibition by nuclear receptors. Cell. May 3, 1996;85(3):403-14.

Karin M. The NF-kappa B activation pathway: its regulation and role in inflammation and cell survival. Cancer J Sci Am. May 1998;4 Suppl 1:S92-9.

Karin, et al. AP-1 function and regulation. Curr Opin Cell Biol. Apr. 1997;9(2):240-6.

Lee, et al. TRAF2 is essential for JNK but not NF-kappaB activation and regulates lymphocyte proliferation and survival. Immunity. Nov. 1997;7(5):703-13.

Lee, et al. Steroid receptor coactivator-1 coactivates activating protein-1-mediated transactivations through interaction with the c-Jun and c-fos subunits. J Biol Chem. Jul. 3, 1998;273(27):16651-4.

Lee, et al. Activating protein-1, nuclear factor-kappaB, and serum response factor as novel target molecules of the cancer-amplified transcription coactivator ASC-2. Mol Endocrinol. Jun. 2000;14(6):915-25.

Leppa, et al. Diverse functions of JNK signaling and c-Jun in stress response and apoptosis. Oncogene. Nov. 1, 1999;18(45):6158-62.

Liberati, et al. Smads bind directly to the Jun family of AP-1 transcription factors. Proc Natl Acad Sci U S A. Apr. 27, 1999;96(9):4844-9.

Lindsten, et al. Regulation of lymphokine messenger RNA stability by a surface-mediated T cell activation pathway. Science. Apr. 21, 1989;244(4902):339-43.

Macian, et al. Transcriptional mechanisms underlying lymphocyte tolerance. Cell. Jun. 14, 2002;109(6):719-31.

Mak, et al. The V(D)J recombination signal sequence and kappa B binding protein Rc binds DNA as dimers and forms multimeric structures with its DNA ligands. Nucleic Acids Res. Feb. 11, 1994;22(3):383-90.

Mak, et al. KRC transcripts: identification of an unusual alternative splicing event. Immunogenetics. Jun. 1998;48(1):32-9.

Matunis, et al. Punt and schnurri regulate a somatically derived signal that restricts proliferation of committed progenitors in the germline. Development. Nov. 1997;124(21):4383-91.

Mondino, et al. Defective transcription of the IL-2 gene is associated with impaired expression of c-Fos, FosB, and JunB in anergic T helper 1 cells. J Immunol. Sep. 1, 1996;157(5):2048-57.

Moreau, et al. Bone-specific expression of the alpha chain of the nascent polypeptide-associated complex, a coactivator potentiating c-Jun-mediated transcription. Mol Cell Biol. Mar. 1998;18(3):1312-21.

Murphy, et al. Molecular interpretation of ERK signal duration by immediate early gene products. Nat Cell Biol. Aug. 2002;4(8):556-64.

Nakano, et al. TRAF5, an acivator of NF-kappaB and putative signal transducer for the lymphotoxin-beta receptor. J Biol Chem. Jun. 21, 1996;271(25):14661-4.

Oukka, et al. A mammalian homolog of Drosophila schnurri, KRC, regulates TNF receptor-driven responses and interacts with TRAF2. Mol Cell. Jan. 2002;9(1):121-31.

Pessah, et al. C-Jun associates with the oncoprotein Ski and suppresses Smad2 transcriptional activity. J Biol Chem. Aug. 9, 2002;277(32):29094-100.

Rayter, et al. p21ras mediates control of IL-2 gene promoter function in T cell activation. EMBO J. Dec. 1992;11(12):4549-56.

Rooney, et al. Coordinate and cooperative roles for NF-AT and AP-1 in the regulation of the murine IL-4 gene. Immunity. May 1995;2(5):473-83.

Rothe, et al. A novel family of putative signal transducers associated with the cytoplasmic domain of the 75 kDa tumor necrosis factor receptor. Cell. Aug. 26, 1994;78(4):681-92.

Staehling-Hampton, et al. A Drosophila protein related to the human zinc finger transcription factor PRDII/MBPI/HIV-EP1 is required for dpp signaling. Development. Oct. 1995;121(10):3393-403.

Sun, et al. PKC-theta is required for TCR-induced NF-kappaB activation in mature but not immature T lymphocytes. Nature. Mar. 23, 2000;404(6776):402-7.

Szabo, et al. A novel transcription factor, T-bet, directs Th1 lineage commitment. Cell. Mar. 17, 2000;100(6):655-69.

Takagi, et al. Murine Schnurri-2 is required for positive selection of thymocytes. Nat Immunol. Nov 2001;2(11):1048-53.

Torres-Vazquez, et al. The transcription factor Schnurri plays a dual role in mediating Dpp signaling during embryogenesis. Development. May 2001;128(9):1657-70.

Torres-Vazquez, et al. schnurri is required for dpp-dependent patterning of the Drosophila wing. Dev Biol. Nov. 15, 2000;227(2):388-402.

Udagawa, et al. Schnurri interacts with Mad in a Dpp-dependent manner. Genes Cell. May 2000;5(5):359-69.

Ullman, et al. Jun family members are controlled by a calcium-regulated, cyclosporin A-sensitive signaling pathway in activated T lymphocytes. Genes Dev. Feb. 1993;7(2):188-96.

Wajant, et al. TNF receptor associated factors in cytokine signaling. Cytokine Growth Factor Rev. Mar. 1999;10(1):15-26.

Wallach, et al. Tumor necrosis factor receptor and Fas signaling mechanisms. Annu Rev Immunol. 1999;17:331-67.

Weiss, et al. Regulation of c-Jun NH(2)-terminal kinase (Jnk) gene expression during T cell activation. J Exp Med. Jan. 3, 2000;191(1):139-46.

Wu, et al. IEX-1L, an apoptosis inhibitor involved in NF-kappaB-mediated cell survival. Science. Aug. 14, 1998;281(5379):998-1001.

Wu, et al. The mouse DNA binding protein Rc for the kappa B motif of transcription and for the V(D)J recombination signal sequences contains composite DNA-protein interaction domains and belongs to a new family of large transcriptional proteins. Genomics. Aug. 1, 1996;35(3):415-24.

Wu. ZAS: C2H2 zinc finger proteins involved in growth and development. Gene Expr. 2002;10(4):137-52.

Wu, et al. The DNA-binding ability of HIVEP3/KRC decreases upon activation of V(D)J recombination. Immunogenetics. Sep. 2001;53(7):564-71.

Yeh, et al. Early lethality, functional NF-kappaB activation, and increased sensitivity to TNF-induced cell death in TRAF2-deficient mice. Immunity. Nov. 1997;7(5):715-25.

Zhang, et al. Smad3 and Smad4 cooperate with c-Jun/c-Fos to mediate TGF-beta-induced transcription. Nature. Aug. 27, 1998;394(6696):909-13.

* cited by examiner

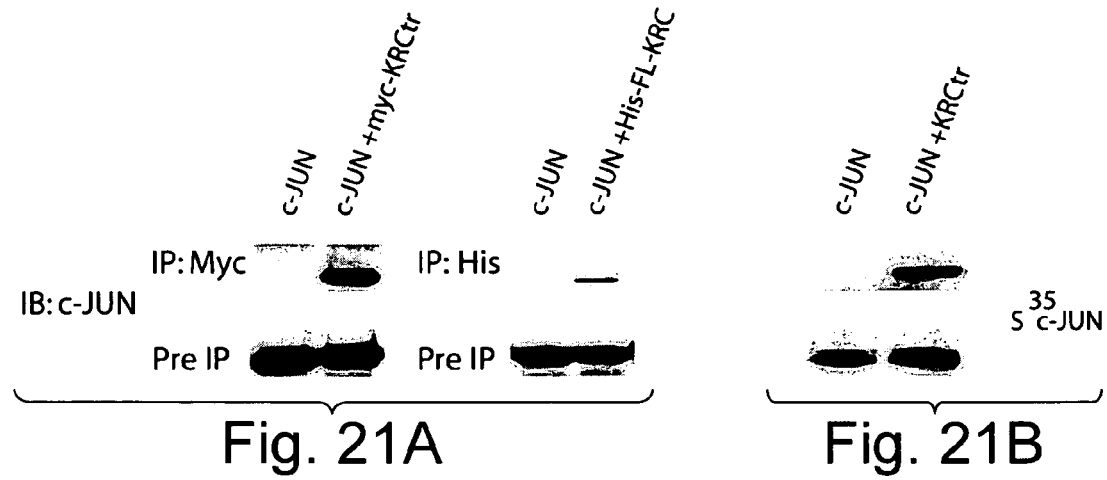
Fig. 21A
Fig. 21B
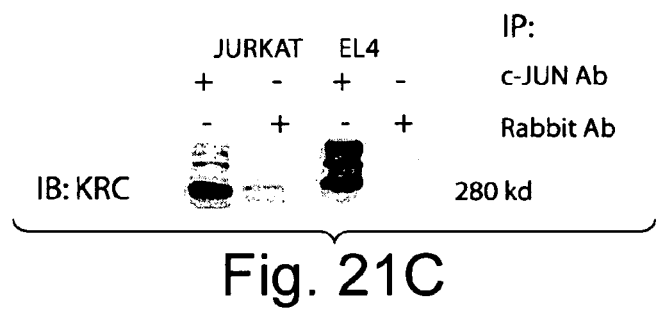
Fig. 21C
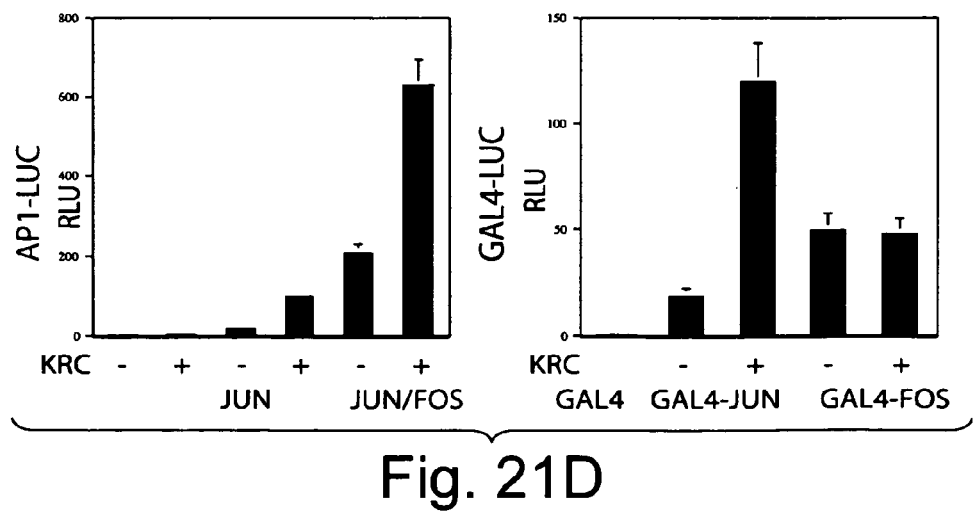
Fig. 21D

METHODS FOR MODULATING AN IMMUNE RESPONSE BY MODULATING KRC ACTIVITY

RELATED APPLICATIONS

This application claims the benefit of priority to PCT application PCT/US02/14166, filed May 3, 2002, now pending, and U.S. Provisional Application Ser. No. 60/288,369, filed May 3, 2001, the entire contents of each of these applications are incorporated herein by this reference.

GOVERNMENT FUNDING

Work described herein was supported, at least in part, under grants AI 029673 and AR 046983 awarded by the National Institutes of Health. The U.S. government therefore may have certain rights in this invention.

BACKGROUND OF THE INVENTION

Transcription factors are a group of molecules within the cell that function to connect the pathways from extracellular signals to intracellular responses. Immediately after an environmental stimulus, these proteins which reside predominantly in the cytosol are translocated to the nucleus where they bind to specific DNA sequences in the promoter elements of target genes and activate the transcription of these target genes. One family of transcription factors, the ZAS (zinc finger-acidic domain structures) DNA binding protein family is involved in the regulation of gene transcription, DNA recombination, and signal transduction (Mak, C. H., et al. 1998. *Immunogenetics* 48: 32-39).

Zinc finger proteins are identified by the presence of highly conserved Cys2His2 zinc fingers (Mak, C. H., et al. 1998. *Immunogenetics* 48: 32-39). The zinc fingers are an integral part of the DNA binding structure called the ZAS domain. The ZAS domain is comprised of a pair of zinc fingers, a glutamic acid/aspartic acid-rich acidic sequence and a serine/threonine rich sequence (Mak, C. H., et al. 1998. *Immunogenetics* 48: 32-39). The ZAS domains have been shown to interact with the kB like cis-acting regulatory elements found in the promoter or enhancer regions of genes. The ZAS proteins recognize nuclear factor kB binding sites which are present in the enhancer sequences of many genes, especially those involved in immune responses (Bachmeyer, et al. 1999. *Nuc. Acid Res.* 27, 643-648). The ZAS DNA binding proteins have been shown to be transcription regulators of these target genes (Bachmeyer, et al. 1999. *Nuc. Acid Res.* 27, 643-648; Wu et al. 1998. *Science* 281, 998-1001).

The zinc finger transcription factor Kappa Recognition Component ("KRC") is a member of the ZAS DNA binding family of proteins (Bachmeyer, et al. 1999. *Nuc. Acid Res.* 27, 643-648; Wu et al. 1998. *Science* 281, 998-1001). The KRC gene was identified as a DNA binding protein for the heptameric consensus signal sequences involved in somatic V(D)J recombination of the immune receptor genes (Mak, C. H., et al. 1994. *Nuc. Acid Res.* 22: 383-390). KRC is a substrate for epidermal growth factor receptor kinase and p34cdc2 kinase in vitro (Bachmeyer, et al. 1999. *Nuc. Acid Res.* 27, 643-648). However, other functions of KRC and the signal transduction pathways that activate KRC in vivo were not known.

Gene-specific transcription factors provide a promising class of targets for novel therapeutics because they provide substantial specificity and are known to be involved in human disease. A number of extremely effective presently marketed drugs act, at least indirectly, by modulating gene transcription. For instance, in many cases of heart disease, the LDL receptor is pathogenically down-regulated at the level of transcription by intracellular sterol levels. The drug compactin, an inhibitor of HMG CoA reductase, functions by up-regulating transcription of the LDL receptor gene which leads to clearance of cholesterol from the blood stream.

In another example, transcription factors can be modulated to regulate an immune response. In autoimmune diseases, self-tolerance is lost and the immune system attacks "self" tissue as if it were a foreign target. Many autoimmune diseases are presently known, such as multiple sclerosis (MS), rheumatoid arthritis, insulin-dependent diabetes mellitus, hemolytic anemias, rheumatic fever, Crohn's disease, Guillain-Barre syndrome, psoriasis, glomerulonephritis, autoimmune hepatitis, multiple sclerosis, etc. In diseases such as these, inhibiting the immune response is desirable. In addition, inhibiting the body's immune response is beneficial in prevention, for example, of organ transplant rejection. Conversely, enhancing the immune response is beneficial in certain circumstances such as the treatment of AIDS, cancer, atherosclerosis and diabetic complications (Sen, P. et al. 1996. *FASEB Journal* 10:709-720, 1996).

Urgently needed are efficient methods of identifying pharmacological agents or drugs which are active at the level of gene transcription. Specifically, agents for use modulating such cellular processes in T cells are needed to regulate the immune response. Agents and methods of using such agents in modulation of cell survival, proliferation, differentiation and/or motility would be of great benefit.

SUMMARY OF THE INVENTION

The present invention is based, at least in part, on the discovery that KRC molecules have multiple important functions as modulating agents in regulating a wide variety of cellular processes. The invention is based, at least in part, on the discovery that KRC inhibits NFkB transactivation, increases TNF-alpha induced apoptosis, inhibits JNK activation, inhibits endogenous TNF-alpha expression, promotes immune cell proliferation and immune cell activation (e.g., in T cells (such as Th1 cells), B cells, or macrophages), activates IL-2 expression e.g., by activating the AP-1 transcription factor, and increases actin polymerization. The present invention also demonstrates that KRC interacts with TRAF. Furthermore, the present invention demonstrates that KRC physically interacts with the c-Jun component of AP-1 to control its degradation.

In one aspect, the invention pertains to a method for modulating the expression and/or biological activity of a KRC polypeptide in a subject comprising contacting an immune cell from the subject with a compound that modulates the expression and/or biological activity of a KRC polypeptide in the immune cell such that the expression and/or biological activity of the KRC polypeptide in the subject is modulated.

In one embodiment, the step of contacting occurs in vivo. In another embodiment, the step of contacting occurs in vitro.

In one embodiment, the cell is selected from the group consisting of: a T cell, a B cell, and a macrophage.

In one embodiment, KRC activity is enhanced. In another embodiment, KRC activity is inhibited.

In one embodiment, the agent is selected from the group consisting of: a nucleic acid molecule encoding a polypeptide comprising a biologically active KRC domain, a polypeptide comprising a biologically active KRC domain, and a small molecule KRC agonist.

In one embodiment, the agent is selected from the group consisting of: an intracellular antibody, a nucleic acid molecule that is antisense to a nucleic acid molecule encoding KRC, a KRC siRNA molecule, a dominant negative KRC molecule, and a small molecule KRC antagonist.

In another embodiment, the biological activity is selected from the group consisting of: modulation of TNFα production, modulation of IL-2 production, modulation of JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In one embodiment, cytokine gene expression is inhibited.

In another aspect, the invention pertains to a method for modulating apoptosis in an immune cell comprising contacting an immune cell with a compound that modulates the expression and/or biological activity of KRC in the immune cell such that apoptosis in the subject is modulated.

In yet another aspect, the invention pertains to a method for modulating inflammation in a subject comprising contacting an immune cell from the subject with a compound that modulates the expression and/or biological activity of KRC in the immune cell such that inflammation in the subject is modulated.

In one embodiment, the step of contacting occurs in vivo. In another embodiment, the step of contacting occurs in vitro.

In one embodiment, the cell is selected from the group consisting of: a T cell, a B cell, and a macrophage.

In one embodiment, KRC activity is enhanced. In another embodiment, KRC activity is inhibited.

In one embodiment, the agent is selected from the group consisting of: a nucleic acid molecule encoding a polypeptide comprising a biologically active KRC domain, a polypeptide comprising a biologically active KRC domain, and a small molecule KRC agonist.

In another embodiment, the agent is selected from the group consisting of: an intracellular antibody, a nucleic acid molecule that is antisense to a nucleic acid molecule encoding KRC, a KRC siRNA molecule, a dominant negative KRC molecule, and a small molecule KRC antagonist.

In one embodiment, the activity is selected from the group consisting of: modulation of TNFα production, modulation of IL-2 production, modulation of JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In one embodiment, apoptosis is inhibited.

In another aspect, the invention pertains to a method for modulating immune cell proliferation comprising contacting an immune cell with a compound that modulates the expression and/or biological activity of KRC in the immune cell such that immune cell proliferation is modulated.

In still another aspect, the invention pertains to a method for modulating immune cell activation comprising contacting an immune cell from the subject with a compound that modulates the expression and/or biological activity of KRC in said immune cell such that immune cell activation is modulated.

In one embodiment, the cell is selected from the group consisting of: a T cell, a B cell, and a macrophage.

In one embodiment, the cell is a Th1 cell.

In another embodiment, IL-2 expression is increased.

In another embodiment, the step of contacting occurs in vivo. In another embodiment, the step of contacting occurs in vitro.

In one embodiment, KRC activity is enhanced. In another embodiment, KRC activity is inhibited.

In one embodiment, the agent is selected from the group consisting of: a nucleic acid molecule encoding a polypeptide comprising a biologically active KRC domain, a polypeptide comprising a biologically active KRC domain, and a small molecule KRC agonist In one embodiment, the agent is selected from the group consisting of: an intracellular antibody, a nucleic acid molecule that is antisense to a nucleic acid molecule encoding KRC, a KRC siRNA molecule, a dominant negative KRC molecule, and a small molecule KRC antagonist.

In one embodiment, the activity is selected from the group consisting of: modulation of TNFα production, modulation of IL-2 production, modulation of JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In one embodiment, immune cell proliferation is increased. In another embodiment, immune cell activation is increased.

In still another aspect, the invention pertains to a method for inhibiting metastatic growth of a tumor cell in a subject comprising contacting a tumor cell from the subject with a compound that modulates the expression and/or biological activity of KRC in the tumor cell such that metastatic growth of the tumor cell in the subject is modulated.

In still another aspect, the invention pertains to a method for modulating the interaction between a KRC molecule and a KRC-binding partner molecule comprising contacting an immune cell with a compound that modulates the interaction between KRC and a KRC-binding partner in the immune cell such that the interaction between KRC and a KRC-binding partner is modulated.

In one embodiment, the KRC-binding partner is TRAF or c-Jun.

In one embodiment, the step of contacting occurs in vivo. In another embodiment, the step of contacting occurs in vitro.

In one embodiment, the interaction between a KRC molecule and a KRC-binding partner molecule is inhibited.

In one embodiment, the agent is selected from the group consisting of: an intracellular antibody, a nucleic acid molecule that is antisense to a TRAF molecule, a nucleic acid molecule that is antisense to a c-Jun molecule, a nucleic acid molecule that is antisense to a KRC molecule, a dominant negative KRC molecule, a dominant negative c-Jun molecule and a dominant negative TRAF molecule.

In one embodiment, the portion of KRC that interacts with TRAF or c-Jun comprises amino acid residues 204-1055 of KRC.

In one embodiment, cytokine gene expression is inhibited.

In another aspect, the invention pertains to a method for modulating apoptosis in an immune cell comprising contacting an immune cell with an agent that modulates the interaction between a KRC molecule and a KRC-binding partner in the immune cell such that apoptosis in the cell is modulated.

In another aspect, the invention pertains to a method for modulating inflammation in a subject comprising contacting an immune cell from the subject with an agent that modulates the interaction between a KRC molecule and a KRC-binding partner molecule in the immune cell such that inflammation in the subject is modulated.

In one embodiment, the step of contacting occurs in vivo. In another embodiment, the step of contacting occurs in vitro.

In one embodiment, the KRC-binding partner is TRAF or c-Jun.

In another embodiment, the interaction between a KRC molecule and a KRC-binding partner molecule is inhibited.

In one embodiment, the agent is selected from the group consisting of: an intracellular antibody, a nucleic acid molecule that is antisense to a TRAF molecule, a nucleic acid molecule that is antisense to a c-Jun molecule a nucleic acid molecule that is antisense to a KRC molecule, a dominant negative KRC molecule, a dominant negative c-Jun molecule and a dominant negative TRAF molecule.

In another embodiment, the portion of KRC that interacts with TRAF or c-Jun comprises amino acid residues 204-1055 of KRC.

In one embodiment, apoptosis is inhibited.

In another aspect, the invention pertains to a method for identifying a compound which modulates an interaction between a first and a second polypeptide comprising:
(a) contacting a cell having a first polypeptide comprising a TRAF-interacting portion of a KRC molecule and a second polypeptide comprising a KRC-interacting portion of a TRAF molecule in the presence and the absence of a test compound; and
(b) determining the degree of interaction between the first and the second polypeptide in the presence and the absence of the test compound to thereby identify a compound which modulates an interaction between a first and a second polypeptide.

In still another aspect, the invention pertains to a method for identifying a compound which modulates an interaction between a first and a second polypeptide comprising:
(a) contacting a cell having a first polypeptide comprising a c-Jun-interacting portion of a KRC molecule and a second polypeptide comprising a KRC-interacting portion of a c-Jun molecule in the presence and the absence of a test compound; and
(b) determining the degree of interaction between the first and the second polypeptide in the presence and the absence of the test compound to thereby identify a compound which modulates an interaction between a first and a second polypeptide.

In one embodiment, the first polypeptide comprises amino acid residues 204 to 1055 of KRC.

In another embodiment, the first polypeptide comprises at least one KRC zinc finger domain.

In still another embodiment, the second polypeptide comprises a TRAF C domain.

In another embodiment, the second polypeptide is a TRAF 1 polypeptide. In another embodiment, the second polypeptide is a TRAF2 polypeptide. In another embodiment, the second polypeptide is a c-Jun polypeptide.

In another embodiment, the first polypeptide is derived from an exogenous source. In another embodiment, the second polypeptide is derived from an exogenous source.

In one embodiment, the cell is a yeast cell.

In another embodiment, the step of determining the ability of the test compound to modulate the interaction of the first polypeptide and the second polypeptide comprises determining the ability of the compound to modulate growth of the yeast cell on nutritionally selective media.

In another embodiment, the step of determining the ability of the test compound to modulate the interaction of the first polypeptide and the second polypeptide comprises determining the ability of the compound to modulate expression of a reporter gene in the yeast cell.

In still another embodiment, determining the ability of the test compound to modulate the interaction of the first polypeptide and the second polypeptide comprises determining the ability of the test compound to modulate the coimmunoprecipitation of the first polypeptide and the second polypeptide.

In yet another embodiment, determining the ability of the test compound to modulate the interaction of the first polypeptide and the second polypeptide comprises determining the ability of the test compound to modulate signaling via a signal transduction pathway involving KRC in the cell.

In one embodiment, the NFkB-dependent transactivation or JNK phosphorylation is measured.

In another embodiment, AP-1 ubiquitination or degradation of c-fos and/or c-Jun is measured.

In one embodiment, the binding of first and second polypeptide is inhibited. In another embodiment, the binding of first and second polypeptide is stimulated.

In another aspect, the invention pertains to a non-human animal, in which the gene encoding the KRC gene is misexpressed.

In one embodiment, animal is a transgenic animal.

In one embodiment, the transgenic animal is a mouse.

In one embodiment, the KRC gene is disrupted by removal of DNA encoding all or part of the KRC protein.

In one embodiment, the animal is homozygous for the disrupted gene. In another embodiment, the animal is heterozygous for the disrupted gene.

In another embodiment, the animal is a transgenic mouse with a transgenic disruption of the KRC gene. In one embodiment, the disruption is an insertion or deletion.

In another aspect, the invention pertains to a method of identifying a compound that modulates a mammalian KRC biological activity comprising:
(a) contacting cells deficient in KRC or a molecule in a signaling pathway involving KRC with a test compound; and
(b) determining the effect of the test compound on the KRC biological activity, the test compound being identified as a modulator of the biological activity based on the ability of the test compound to modulate the biological activity in the cells deficient in KRC or a molecule in a signaling pathway involving KRC to thereby identify a compound that modulates a mammalian KRC biological activity.

In one embodiment, the cells are in a non-human animal deficient in KRC or a molecule in a signal transduction pathway involving KRC and the cells are contacted with the test compound by administering the test compound to the animal.

In one embodiment, the activity is selected from the group consisting of: modulation of TNFα production, modulation of IL-2 production, modulation of JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In another aspect, the invention pertains to a method of identifying compounds useful in modulating a biological activity of mammalian KRC comprising:
a) providing an indicator composition comprising mammalian KRC or a molecule in a signal transduction pathway involving KRC;
b) contacting the indicator composition with each member of a library of test compounds;

c) selecting from the library of test compounds a compound of interest that modulates the expression, processing, post-translational modification, and/or biological activity of KRC or the molecule in a signal transduction pathway involving KRC; to thereby identify a compound that modulates a biological activity of mammalian KRC.

In one embodiment, the indicator composition is a cell that expresses KRC, and a molecule selected from the group consisting of: TRAF, c-Jun, c-Fos and AP-1 protein.

In one embodiment, the indicator composition is a cell free composition.

In another embodiment, the activity is selected from the group consisting of:

modulation of TNFα production, modulation of IL-2 production, modulation of JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In another aspect, the invention pertains to a method of identifying a compound useful in modulating an autoimmune disease comprising:

a) providing an indicator composition comprising mammalian KRC or a molecule in a signal transduction pathway involving KRC;

b) contacting the indicator composition with each member of a library of test compounds;

c) selecting from the library of test compounds a compound of interest that downmodulates the expression, processing, post-translational modification, and/or activity of KRC or a molecule in a signal transduction pathway involving KRC; to thereby identify a compound that modulates an autoimmune disease.

In one embodiment, the activity of KRC is measured by measuring the binding of KRC to TRAF or c-Jun.

In another embodiment, the activity of KRC is measured by measuring ubiquitination of AP-1.

In one embodiment, the autoimmune disease is selected from the group consisting of: systemic lupus erythematosus; rheumatoid arthritis; goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; multiple sclerosis, inflammatory bowel disease, ulcerative colitis, Crohn's disease, and type I diabetes mellitus.

In yet another aspect, the invention pertains to a method of identifying a compound useful in treating a malignancy comprising:

a) providing an indicator composition comprising mammalian KRC or a molecule in a signal transduction pathway involving KRC;

b) contacting the indicator composition with each member of a library of test compounds;

c) selecting from the library of test compounds a compound of interest that modulates the expression, processing, post-translational modification, and/or activity of KRC or a molecule in a signal transduction pathway involving KRC; to thereby identify a compound that modulates a malignancy.

In one embodiment, the activity of KRC is measured by measuring the binding of KRC to TRAF or c-Jun.

In another embodiment, the activity of KRC is measured by measuring ubiquitination of AP-1.

In one embodiment, the malignancy is selected from the group consisting of: acute lymphoblastic leukemia; acute myeloid leukemia; adrenocortical carcinoma; AIDS-related lymphoma; cancer of the bile duct; bladder cancer; bone cancer, osteosarcomal malignant fibrous histiocytomal brain stem gliomal brain tumor; breast cancer; bronchial adenomas; carcinoid tumors; adrenocortical carcinoma; central nervous system lymphoma; cancer of the sinus, cancer of the gall bladder; gastric cancer; cancer of the salivary glands; cancer of the esophagus; neural cell cancer; intestinal cancer (e.g., of the large or small intestine); cervical cancer; colon cancer; colorectal cancer; cutaneous T-cell lymphoma; B-cell lymphoma; T-cell lymphoma; endometrial cancer; epithelial cancer; endometrial cancer; intraocular melanoma; retinoblastoma; hairy cell leukemia; liver cancer; Hodgkin's disease; Kaposi's sarcoma; acute lymphoblastic leukemia; lung cancer; non-Hodgkin's lymphoma; melanoma; multiple myeloma; neuroblastoma; prostate cancer; retinoblastoma; Ewing's sarcoma; vaginal cancer; Waldenstrom's macroglobulinemia; adenocarcinomas; ovarian cancer, chronic lymphocytic leukemia, pancreatic cancer; and Wilm's tumor.

BRIEF DESCRIPTION OF THE FIGURES

FIG. 1(A) shows a schema of KRC constructs used. FIG. 1(B) upper panel depicts the interaction of KRC tr with TRAFs in mammalian cells. 293 T cells were cotransfected with the indicated FLAG-TRAFs and MYC-tagged KRC tr, and immunoprecipitated with anti-MYC antibody, followed by blotting with anti-FLAG antibody. FIG. 1(B) lower panel depicts the direct western blot of overexpressed TRAFS and KRC tr with anti-FLAG or anti-MYC. FIG. 1(C) depicts the differential interaction of KRC tr with TRAF proteins. The coimmunoprecipitation experiments were performed in the presence of 300 mM NaCl instead of 137 mM NaCl. FIG. 1(D) depicts KRC tr interacting with TRAF2 lacking the Ring finger domain. 293 T cells were transfected with MYC-KRC tr and with FLAG tagged TRAF2 or with FLAG-tagged TRAF2 (87-501). FIG. 1(E) depicts the interaction of KRC tr with endogenous TRAF2 but not with endogenous TRAF5 or TRAF6. 293T were transfected with an expression vector encoding an MYC-tagged KRC tr, or empty plasmid. Lysates from 293T cells were incubated with anti-MYC antibodies. Coimmunoprecipitated endogenous TRAF was detected by western blotting with specific anti-TRAF antibodies.

FIG. 11(A) shows IL-2 promoter transactivation by KRC in Jurkat T cells activated by PMA/Ionomycin. FIG. 11(B) shows transactivation of a composite NFAT-AP 1 reporter by KRC. FIG. 11(C) shows transactivation of an AP-1 reporter by KRC.

FIG. 12(A) shows IL-2 promoter transactivation by KRC in Jurkat T cells activated by the Raji B cell APC line and the superantigen SEE. FIG. 12(B) shows transactivation of a composite NFAT-AP1 reporter by KRC. FIG. 12(C) shows transactivation of an AP-1 reporter by KRC.

FIG. 13(A) shows stable transfectants and FIG. 13(B) shows CD3 and CD3+CD28 stimulated cells.

FIG. 14(A) shows KRC transactivation of the AP-1 reporter is blocked by dominant negative Ras and Raf. FIG. 14(B) shows KRC transactivation of the AP-1 reporter is blocked by dominant negative PKC-theta and by the specific PKC-theta inhibitor Rottlerin.

FIG. 19(A) Stably transfected Jurkat T cell clones with vector (vec) or KRC (Jurkat-KRC) were stimulated with PMA (50 ng/mL) plus ionomycin (2 μM) for 6 hours. IL-2 mRNA abundance was determined by RT-PCR with tubulin as an internal control. FIG. 19(B) Jurkat cells were transiently transfected with an IL-2-Luciferase reporter along with Vector, KRC, or KRCtr (amino acids 204-1055) and, in all cases, a CMV-β-Gal reporter as an internal control (see text for details). 24 hours later, cells were stimulated with PMA plus ionomycin for 6 hours (upper panel) or Raji cells loaded with SEE for 8 hours (lower panel). Luciferase activity was determined and normalized for β-Galactosidase activity. FIG. 19(C) Jurkat cells were transiently transfected with NFAT/AP-1-, NFAT-, or AP-1-Luciferase reporters and treated as above.

FIG. 20(A) Jurkat cells were transiently transfected with AP-1 Luciferase reporter along with KRC and RasN17 DN vectors. 24 hours later cells were pretreated with Rottlerin (10 μM) and stimulated for 6 hours with PMA plus ionomycin. Luciferase activity was measured as above. FIG. 20(B) Jurkat cells were transfected with a GAL4 Luciferase reporter along with a GAL4 DNA binding domain, GAL4-ATF2, or GAL4-ELK1 with or without KRC. 24 hours later, cells were stimulated with PMA plus ionomycin and analyzed for Luciferase activity as above. FIG. 20(C) Jurkat cells were transiently transfected with FLAG-JNK2, and either Vector, KRC, or MKK7. 48 hours later, cells were stimulated with PMA plus ionomycin for 6 hours and JNK activity was determined by immunoprecipitation/kinase assay. Equal amounts of FLAG-Jnk2 protein were immunoprecipitated, as judged by anti-FLAG western blot (lower panel).

FIGS. 21(A)-21(D) show that KRC physically interacts with c-Jun and acts as a transcriptional coactivator. FIG. 21(A) 293T cells were transfected with c-Jun and myc-KRCtr. 48 hours later, lysates were immunoprecipitated with anti-Myc antibody. Immunoprecipitates were probed by western blotting with anti-c-Jun antibody. FIG. 21(B) (left panel) 293T cells were cotransfected with c-Jun and full length His-KRC. 48 hours later, lysates were immunoprecipitated with anti-His antibody (DE8 Omniprobe) and precipitates were probed by western blotting with anti-c-Jun antibody. (right panel) In vitro translated and S35-labelled c-Jun and His-KRCtr were mixed and immunoprecipitated with anti-His antibody. Recovered c-Jun protein was visualized by autoradiography. FIG. 21(C) Jurkat or EL4 T cells were stimulated with PMA plus ionomycin for 45 minutes. Lysates were immunoprecipitated with anti-c-Jun antibody, and immunoprecipitates were probed with specific anti-KRC rabbit antisera. FIG. 21(D) (upper panel) 293T cells were transfected with AP-1 Luciferase along with c-Jun, c-Fos, and KRC. 24 hours later, Luciferase activity was determined as above. (lower panel) 293T cells were transfected with GAL4 Luciferase along with GAL4, GAL4-c-Jun 1-224, or GAL4-c-Fos 208-313. 24 hours later, luciferase activity was determined as above.

FIG. 22(A) shows that the stability of the c-Fos protein in the presence of cycloheximide was compromised in the presence of KRC and dramatically stabilized in the presence of the KRC dominant negative expressing only the ZAS2 domain or in the presence of the antisense KRC. FIG. 22(B), shows that overexpression of antisense KRC, by inhibiting the expression of endogenous KRC, decreased the rate of c-Jun degradation. FIG. 22(C), show that overexpression of full-length KRC, in the presence of low dose cycloheximide blocked endogeneous protein synthesis and led to the rapid degradation of c-Jun. FIG. 22(D) shows the specificity of KRC for the c-Jun/c-Fos AP-1 pair since KRC was unable to promote the degradation of other fos family members Fra1, Fra2 and Fos B.

DETAILED DESCRIPTION OF THE INVENTION

Figure 1A:
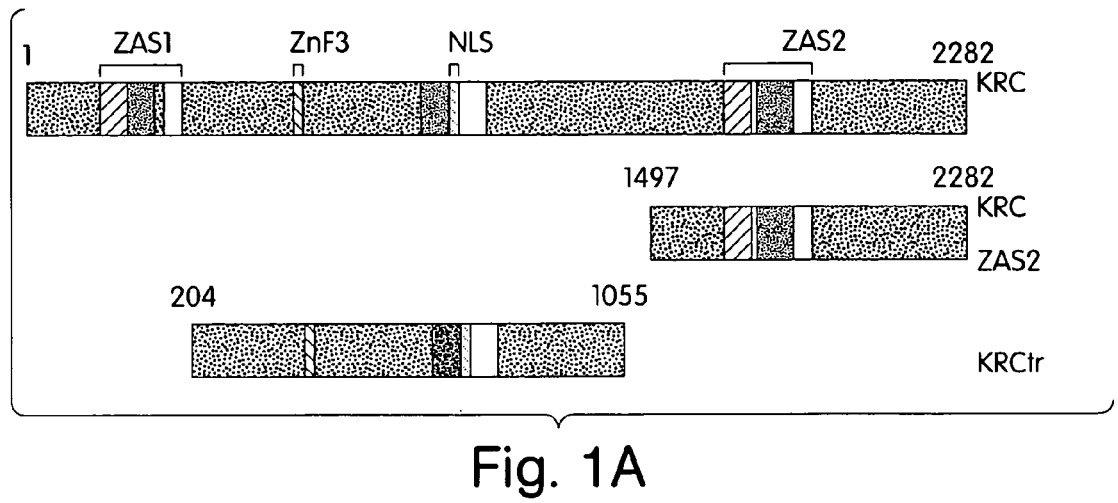
FIGS. 1(A)-1(E) show the interaction of amino acid residues 204 to 1055 of KRC ("KRC tr") (amino acids 204-1055 of SEQ ID NO:2) with TRAF family members.

The present invention is based, at least in part, on the discovery that KRC molecules regulate a wide variety of cellular processes, including inhibiting NFkB transactivation, increasing TNF-alpha induced apoptosis, inhibiting JNK activation, inhibiting endogenous TNF-alpha expression, activating immune cell proliferation and immune cell activation (e.g., in Th1 cells), activating IL-2 expression e.g., by activating the AP-1 transcription factor, and increasing actin polymerization.

The present invention also demonstrates that that KRC interacts with TRAF molecules. The interaction between KRC and TRAF involves the C domain of TRAF and amino acid residues 204 to 1055 of KRC. Furthermore, the present invention demonstrates that KRC physically interacts with the c-Jun component of AP-1 to control its degradation. The KRC protein (for κB binding and putative recognition component of the V(D)J Rss) is a DNA binding protein comprised of 2282 amino acids. KRC has been found to be present in T cells, B cells, and macrophages. The KRC cDNA sequence is set forth in SEQ ID NO:1. The amino acid sequence of KRC is set forth in SEQ ID NO:2. KRC is a member of a family of zinc finger proteins that bind to the kB motif (Bachmeyer, C, et al., 1999. Nuc. Acids. Res. 27(2):643-648). Zinc finger proteins are divided into three classes represented by KRC and the two MHC Class I gene enhancer binding proteins, MBP1 and MBP2 (Bachmeyer, C, et al., 1999. Nuc. Acids. Res. 27(2):643-648).

Zinc finger proteins are identified by the presence of highly conserved Cys2His2 zinc fingers. The zinc fingers are an integral part of the DNA binding structure called the ZAS domain. The ZAS domain is comprised of a pair of zinc fingers, a glutamic acid/aspartic acid-rich acidic sequence and a serine/threonine rich sequence. The ZAS domains have been shown to interact with the kB like cis-acting regulatory elements found in the promoter or enhancer regions of genes. The genes targeted by these zinc finger proteins are mainly involved in immune responses.

The KRC ZAS domain, in particular, has a pair of Cys2-His2 zinc fingers followed by a glutamic acid/aspartic acid-rich acidic sequence and five copies of the serine/threonine-proline-X-arginine/lysine sequence. Southwestern blotting experiments, electrophoretic mobility shift assays (EMSA) and methylation interference analysis has also demonstrated that KRC recombinant proteins bind to the κB motif as well as to the Rss sequence (Bachmeyer, et al. 1999. Nuc. Acid Res. 27, 643-648; Wu et al. 1998. Science 281, 998-1001) and do so in highly ordered complexes (Mak, C. H., et al. 1994. Nuc. Acid Res. 22, 383-390.; Wu et al. 1998. Science 281, 998-1001).

Similar zinc finger-acidic domain structures are present in human KBP1, MBP1 and MBP2, rat ATBP1 and ATBP2, and mouse αA-CRYBP proteins. KRC has recently been shown to regulate transcription of the mouse metastasis-associated gene, s100A4/mts1*, by binding to the Sb element (a kB like sequence) of the gene. (Hjelmsoe, I., et al. 2000. J. Biol. Chem. 275(2): 913-920). KRC is regulated by post-translational modification as evidenced by the fact that pre-B cell nuclear protein kinases phosphorylate KRC proteins on serine and tyrosine residues. Phosphorylation increases DNA binding, providing a mechanism by which KRC may respond to signals transmitted from the cell surface (Bachmeyer, C, et al., 1999. Nuc. Acids. Res. 27(2):643-648). Two prominent ser/thr-specific protein kinases that play a central role in signal transduction are cyclic AMP-dependent protein kinase A (PKA) and the protein kinase C (PKC family). Numerous other serine/threonine specific kinases, including the family of mitogen-activated protein (MAP) kinases serve as important signal transduction proteins which are activated in either growth-factor receptor or cytokine receptor signaling. Other protein ser/thr kinases important for intracellular signaling are Calcium-dependent protein kinase (CaM-kinase II) and the c-raf-protooncogene. KRC is known to be a substrate for epidermal growth factor receptor kinase and p34cdc2 kinase in vitro.

The results of a yeast two hybrid screen using amino acid residues 204 to 1055 of KRC (which includes the third zinc finger) as bait demonstrate that KRC interacts with the TRAF family of proteins and that this interaction occurs through the TRAF C domain and that KRC interacts with higher affinity with TRAF2 than with TRAF5 and TRAF6. (See Example 1).

Recent research has lead to the isolation of polypeptide factors named TRAFs for tumor necrosis factor receptor associated factors, which participate in the TNFR signal transduction cascade. Six members of the TRAF family of proteins have been identified in mammalian cells (reviewed in Arch, R. H., et al. 1998. *Genes Dev.* 12, 2821-2830). All TRAF proteins, with the exception of TRAF1, contain an amino terminal RING finger domain with a characteristic pattern of cysteines and histidines that coordinate the binding of $Zn^{2+}$ ions (Borden, K. L. B., et al. 1995. *EMBO J* 14, 1532-1521), which is followed by a stretch of multiple zinc fingers. All TRAFs share a highly conserved carboxy-terminal domain (TRAF-C domain) which is required for receptor binding and can be divided into two parts, a highly conserved domain which mediates homo and heterodimerization of TRAF proteins and also the association of the adapter proteins with their associated receptors and an amino-terminal half that displays a coiled-coil configuration. TRAF molecules have distinct patterns of tissue distribution, are recruited by different cell surface receptors and have distinct functions as revealed most clearly by the analysis of TRAF-deficient mice (see Lomaga, M. A., et al. 1999. *Genes Dev.* 13, 1015-24; Nakano, H., et al. 1999. *Proc. Natl. Acad. Sci. USA* 96, 9803-9808; Nguyen, L. T., et al. 1999. *Immunity* 11, 379-389; Xu, Y., et al. 1996. *Immunity* 5, 407-415.; Yeh, W. C., et al. 1997. *Immunity* 7, 715-725).

Tumor necrosis factor (TNF) is a cytokine produced mainly by activated macrophages which elicits a wide range of biological effects. These include an important role in endotoxic shock and in inflammatory, immunoregulatory, proliferative, cytotoxic, and anti-viral activities (reviewed by Goeddel, D. V. et al., 1986. *Cold Spring Harbor Symposia on Quantitative Biology* 51: 597-609; Beutler, B. and Cerami, A., 1988. *Ann. Rev. Biochem.* 57: 505-518; Old, L. J., 1988. *Sci. Am.* 258(5): 59-75; Fiers, W. 1999. *FEBS Lett.* 285(2): 199-212). The induction of the various cellular responses mediated by TNF is initiated by its interaction with two distinct cell surface receptors, an approximately 55 kDa receptor termed TNFR1 and an approximately 75 kDa receptor termed TNFR2. Human and mouse cDNAs corresponding to both receptor types have been isolated and characterized (Loetscher, H. et al., 1990. *Cell* 61:351; Schall, T. J. et al., 1990. *Cell* 61: 361; Smith, C. A. et al., 1990 *Science* 248: 1019; Lewis, M. et al., 1991. *Proc. Natl. Acad. Sci. USA* 88: 2830-2834; Goodwin, R. G. et al., 1991. *Mol. Cell. Biol.* 11:3020-3026).

TNFα binds to two distinct receptors, TNFR1 and TNFR2, but in most cell types NFκB activation and JNK/SAPK activation occur primarily through TNFR1. TNFR1 is known to interact with TRADD which functions as an adaptor protein for the recruitment of other proteins including RIP, a serine threonine kinase, and TRAF2. Of the six known TRAFs, TRAF2, TRAF5 and TRAF6 have all been linked to NFκB activation (Cao, Z., et al. 1996. *Nature* 383: 443-6; Rothe, M., et al. 1994. *Cell* 78: 681-692; Nakano, H., et al. 1996. *J. Biol. Chem.* 271:14661-14664), and TRAF2 in particular has been linked to activation of the JNK/SAPK proteins as shown unequivocally by the failure of TNFα to activate this MAP kinase in cells lacking TRAF2 or expressing a dominant negative form of TRAF2 (Yeh, W. C., et al. 1997. *Immunity* 7: 715-725; Lee, S. Y., et al. 1997. *Immunity* 7:1-20).

Various aspects of the invention are described in further detail in the following subsections:

I. Definitions

As used herein, the term "KRC" refers to κB binding and putative recognition component of the V(D)J Rss. The nucleotide sequence of KRC is set forth in SEQ ID NO:1 and the amino acid sequence of KRC is set forth in SEQ ID NO:2. The amino acid sequence of the ZAS domain of KRC is set forth in amino acids 1497-2282 of SEQ ID NO:2. The amino acid sequence of KRC tr is shown in amino acid residues 204 to 1055 of SEQ ID NO:2. As used herein, the term "KRC", unless specifically used to refer a specific SEQ ID NO, will be understood to refer to a KRC family polypeptide as defined below.

"KRC family polypeptide" is intended to include proteins or nucleic acid molecules having a KRC structural domain or motif and having sufficient amino acid or nucleotide sequence identity with a KRC molecule as defined herein. Such family members can be naturally or non-naturally occurring and can be from the same or different species. For example, a family can contain a first protein of human origin, as well as other, distinct proteins of human origin or, alternatively, can contain homologues of non-human origin. Preferred members of a family may also have common functional characteristics. Preferred KRC polypeptides comprise one or more of the following KRC characteristics: a pair of Cys2-His2 zinc fingers followed by a Glu- and Asp-rich acidic domain and five copies of the ser/Thr-Pro-X-Arg/Lys sequence thought to bind DNA.

As used herein, the term "KRC activity", "KRC biological activity" or "activity of a KRC polypeptide" includes the ability to modulate an immune response (e.g., by inhibiting or enhancing immune cell activation and/or proliferation, such as by modulating cytokine gene expression), cell survival (e.g., by modulating apoptosis), and/or the ability to modulate a signaling pathway (e.g., an NFkB signaling pathway, a JNK signaling pathway), the ability to modulate actin polymerization, ubiquitination of AP-1, degradation of c-Jun, degradation of c-Fos, effector T cell function, T cell anergy and/or T cell differentiation.

As used herein, the various forms of the term "modulate" are intended to include stimulation (e.g., increasing or upregulating a particular response or activity) and inhibition (e.g., decreasing or downregulating a particular response or activity).

As described in the appended Examples, KRC increases immune cell activation and cytokine production. In addition, when KRC is overexpressed, it results in the inhibition of NFkB and JNK signaling pathways. Inhibition of these pathways is associated with cellular inflammatory and apoptotic responses. In one embodiment, the KRC activity is a direct activity, such as an association with a KRC-target molecule or binding partner. As used herein, a "target molecule", "binding partner" or "KRC binding partner" is a molecule with which a KRC protein binds or interacts in nature, such that KRC mediated function is achieved.

As used herein the term "TRAF" refers to TNF Receptor Associated Factor (See e.g., Wajant et al, 1999, *Cytokine Growth Factor Rev* 10:15-26). The "TRAF" family includes a family of cytoplasmic adapter proteins that mediate signal transduction from many members of the TNF-receptor superfamily and the interleukin-1 receptor (see e.g., Arch, R. H. et al., 1998, *Genes Dev.* 12:2821-2830). As used herein, the term "TRAF C domain" refers to the highly conserved sequence motif found in TRAF family members.

As used herein, the terms "TRAF interacting portion of a KRC molecule" or "c-Jun interacting portion of a KRC molecule" includes a region of KRC that interacts with TRAF or c-Jun. In a preferred embodiment, a region of KRC that interacts with TRAF or c-Jun is amino acid residues 204-1055 of SEQ ID NO:2. As used herein, the term "KRC interacting portion of a TRAF molecule" or "KRC interacting portion of a TRAF molecule" includes a region of TRAF or c-Jun that interacts with KRC. In a preferred embodiment, a region of TRAF that interacts with KRC is the TRAF C domain.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

As used herein, the term "contacting" (i.e., contacting a cell e.g. an immune cell, with a compound) is intended to include incubating the compound and the cell together in vitro (e.g., adding the compound to cells in culture) or administering the compound to a subject such that the compound and cells of the subject are contacted in vivo. The term "contacting" is not intended to include exposure of cells to a KRC modulator that may occur naturally in a subject (i.e., exposure that may occur as a result of a natural physiological process).

As used herein, the term "test compound" includes a compound that has not previously been identified as, or recognized to be, a modulator of KRC activity and/or expression and/or a modulator of cell growth, survival, differentiation and/or migration.

The term "library of test compounds" is intended to refer to a panel comprising a multiplicity of test compounds.

As used herein, the term "cell free composition" refers to an isolated composition which does not contain intact cells. Examples of cell free compositions include cell extracts and compositions containing isolated proteins.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "immune response" includes immune cell-mediated (e.g., T cell and/or B cell-mediated) immune responses that are influenced by modulation of immune cell activation. Exemplary immune responses include B cell responses (e.g., antibody production), T cell responses (e.g., proliferation, cytokine production and cellular cytotoxicity), and activation of cytokine responsive cells, e.g., macrophages. In a preferred embodiment of the invention, an immune response is T cell mediated. As used herein, the term "downregulation" with reference to the immune response includes a diminution in any one or more immune responses, preferably T cell responses, while the term "upregulation" with reference to the immune response includes an increase in any one or more immune responses, preferably T cell responses. It will be understood that upregulation of one type of immune response may lead to a corresponding downregulation in another type of immune response. For example, upregulation of the production of certain cytokines (e.g., IL-10) can lead to downregulation of cellular immune responses. In addition, it will be understood that KRC may have one effect on immune responses in the context of T cell receptor-mediated signaling and another in the context of TNFα-mediated signaling.

As used herein, the term "immune cell" includes cells that are of hematopoietic origin and that play a role in the immune response. immune cells include lymphocytes, such as B cells and T cells; natural killer cells; and myeloid cells, such as monocytes, macrophages, eosinophils, mast cells, basophils, and granulocytes.

As used herein, the term "T cell" includes $CD4^+$ T cells and $CD8^+$ T cells. The term T cell also includes both T helper 1 (Th1) type T cells and T helper 2 (Th2) type T cells, also referred to herein as "effector T cells". The terms "antigen presenting cell" and "APC", as used interchangeably herein, include professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "receptor" includes immune cell receptors that bind antigen, complexed antigen (e.g., in the context of MHC molecules), or antibodies. Activating receptors include T cell receptors (TCRs), B cell receptors (BCRs), cytokine receptors, LPS receptors, complement receptors, and Fc receptors. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

As used herein, the term "dominant negative" includes KRC molecules (e.g., portions or variants thereof) that compete with native (i.e., wild-type) KRC molecules, but which do not have KRC activity. Such molecules effectively decrease KRC activity in a cell.

As used herein, the term "inflammation" includes a response to injury which results in a dilation of the blood capillaries, a decrease in blood flow and an accumulation of leucocytes at the site of injury.

As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. As used herein, the term "modulating apoptosis" includes modulating programmed cell death in a cell, such as a epithelial cell. As used herein, the term "modulates apoptosis" includes either up regulation or down regulation of apoptosis in a cell. Modulation of apoptosis is discussed in more detail below and can be useful in ameliorating various disorders, e.g., neurological disorders.

As used herein, the term "NFkB signaling pathway" refers to any one of the signaling pathways known in the art which involve activation or deactivation of the transcription factor NFkB, and which are at least partially mediated by the NFkB factor (Karin, 1998, *Cancer J from Scientific American*, 4:92-99; Wallach et al, 1999, *Ann Rev of Immunology*, 17:331-367). Generally, NFkB signaling pathways are responsive to a number of extracellular influences e.g. mitogens, cytokines, stress, and the like. The NFkB signaling pathways involve a range of cellular processes, including, but not limited to, modulation of apoptosis. These signaling pathways often comprise, but are by no means limited to, mechanisms which involve the activation or deactivation via phosphorylation state of an inhibitor peptide of NFkB (IkB), thus indirectly activating or deactivating NFkB.

As used herein, the term "JNK signaling pathway" refers to any one of the signaling pathways known in the art which involve the Jun amino terminal kinase (JNK) (Karin, 1998, *Cancer J from Scientific American*, 4:92-99; Wallach et al, 1999, *Ann Rev of Immunology*, 17:331-367). This kinase is generally responsive to a number of extracellular signals e.g. mitogens, cytokines, stress, and the like. The JNK signaling pathways mediate a range of cellular processes, including, but not limited to, modulation of apoptosis. In a preferred embodiment, JNK activation occurs through the activity of one or more members of the TRAF protein family (See, e.g., Wajant et al, 1999, *Cytokine Growth Factor Rev* 10:15-26).

As used herein, "AP-1" refers to the transcription factor activator protein 1 (AP-1) which is a family of DNA-binding factors that are composed of dimers of two proteins that bind to one another via a leucine zipper motif. The best characterized AP-1 factor comprises the proteins Fos and Jun. (Angel, P. and Karin, M. (1991) *Biochim. Biophys. Acta* 1072:129-157; Orengo, I. F., Black, H. S., et al. (1989) *Photochem. Photobiol.* 49:71-77; Curran, T. and Franza, B. R., Jr. (1988) *Cell* 55, 395-397). The AP-1 dimers bind to and transactivate promoter regions on DNA that contain cis-acting phorbol 12-tetradecanoate 13-acetate (TPA) response elements to induce transcription of genes involved in cell proliferation, metastasis, and cellular metabolism (Angel, P., et al. (1987) *Cell* 49, 729-739. AP-1 is induced by a variety of stimuli and is implicated in the development of cancer and autoimmune disease.

As used herein, the term "nucleic acid" is intended to include fragments or equivalents thereof (e.g., fragments or equivalents thereof KRC, TRAF, c-Jun or c-Fos). The term "equivalent" is intended to include nucleotide sequences encoding functionally equivalent KRC proteins, i.e., proteins which have the ability to bind to the natural ligand(s) of the KRC antigen. In a preferred embodiment, a functionally equivalent KRC protein has the ability to bind TRAF in the cytoplasm of an immune cell, e.g., a T cell. In another preferred embodiment, a functionally equivalent KRC protein has the ability to bind c-Jun in the nucleoplasm of an immune cell, e.g., a T cell.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

The nucleotide sequence of a DNA or RNA molecule coding for a KRC polypeptide of the invention (or a portion thereof) can be used to derive the KRC amino acid sequence, using the genetic code to translate the DNA or RNA molecule into an amino acid sequence. Likewise, for any KRC -amino acid sequence, corresponding nucleotide sequences that can encode KRC protein can be deduced from the genetic code (which, because of its redundancy, will produce multiple nucleic acid sequences for any given amino acid sequence). Thus, description and/or disclosure herein of a KRC nucleotide sequence should be considered to also include description and/or disclosure of the amino acid sequence encoded by the nucleotide sequence. Similarly, description and/or disclosure of a KRC amino acid sequence herein should be considered to also include description and/or disclosure of all possible nucleotide sequences that can encode the amino acid sequence.

One aspect of the invention pertains to isolated nucleic acid molecules that encode KRC proteins or biologically active portions thereof, as well as nucleic acid fragments sufficient for use as hybridization probes to identify KRC -encoding nucleic acids (e.g., KRC mRNA) and fragments for use as PCR primers for the amplification or mutation of KRC nucleic acid molecules. It will be understood that in discussing the uses of KRC nucleic acid molecules, e.g., as shown in SEQ. ID NO:1 or a nucleotide sequence encoding another KRC family polypeptide, that fragments of such nucleic acid molecules as well as full length KRC nucleic acid molecules can be used. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid molecule of the present invention, e.g., a nucleic acid molecule having the nucleotide sequence of SEQ ID NO: 1 or a nucleotide sequence encoding another KRC family polypeptide, or a portion thereof, can be isolated using standard molecular biology techniques and the sequence information provided herein. For example, using all or portion of the nucleic acid sequence of SEQ ID NO: 1 or a nucleotide sequence encoding another KRC family polypeptide as a hybridization probe, KRC nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed,* Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1 or a nucleotide sequence encoding another KRC family polypeptide can be isolated by the polymerase chain reaction (PCR) using synthetic oligonucleotide primers designed based upon the sequence of SEQ ID NO: 1 or a nucleotide sequence encoding another KRC family polypeptide respectively.

Nucleic acid sequences encoding other KRC family polypeptides can be identified based on nucleic acid and/or amino acid identity with KRC, possession of KRC domains, and/or possession of a KRC activity as defined herein.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to KRC nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO: 1 a nucleic acid molecule encoding another KRC family polypeptide.

In another preferred embodiment, an isolated nucleic acid molecule of the invention comprises a nucleic acid molecule which is a complement of the nucleotide sequence shown in SEQ ID NO: 1 or a nucleotide sequence encoding another KRC family polypeptide or a portion of any of these nucleotide sequences. A nucleic acid molecule which is complementary to the nucleotide sequence shown in SEQ ID NO: 1 or a nucleotide sequence encoding another KRC family polypeptide is one which is sufficiently complementary to the nucleotide sequence shown in SEQ ID NO: 1 or a nucleotide sequence encoding another KRC family polypeptide respectively, such that it can hybridize to the nucleotide sequence shown in SEQ ID NO: 1 or a nucleotide sequence encoding another KRC family polypeptide respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1 or a nucleotide sequence encoding another KRC family polypeptide or a portion thereof, e.g, an intracellular domain, an extracellular domain, a transmembrane domain, a zinc finger domain, a glutamic acid/aspartic acid-rich domain or a serine/threonin-proline-X-arginine/lysine domain.

Moreover, the nucleic acid molecule of the invention can comprise only a portion of the nucleic acid sequence of SEQ ID NO: 1 a nucleic acid molecule encoding another KRC family polypeptide for example a fragment which can be used as a probe or primer or a fragment encoding a biologically active portion of a KRC protein. The nucleotide sequence determined from the cloning of the KRC genes allows for the generation of probes and primers designed for use in identifying and/or cloning yet other KRC family members, as well as KRC family homologues from other species. The probe/primer typically comprises a substantially purified oligonucleotide. In one embodiment, the oligonucleotide comprises a region of nucleotide sequence that hybridizes under stringent conditions to at least about 12 or 15, preferably about 20 or 25, more preferably about 30, 35, 40, 45, 50, 55, 60, 65, 75, or 100 consecutive nucleotides of a sense sequence of SEQ ID NO: 1 or a nucleotide sequence encoding another KRC family polypeptide or of a naturally occurring allelic variant or mutant of SEQ ID NO: 1 or a nucleotide sequence encoding another KRC family polypeptide. In another embodiment, a nucleic acid molecule of the present invention comprises a nucleotide sequence which is at least about 400, 450, 500, 550, 600, 650, 700, 750, 800, 900, 1000, 1100, 1200, 1300, 1400, 1500, or more nucleotides in length and hybridizes under stringent hybridization conditions to a nucleic acid molecule of SEQ ID NO: 1 or a nucleotide sequence encoding another KRC family polypeptide or the complement thereof.

In another embodiment, a nucleic acid molecule of the invention comprises at least about 100, 200, 300, 400, 500, 600, 700, 800, 900, 1000, 1100, 1200, 1300, 1400, 1500, or more contiguous nucleotides of SEQ ID NO: 1 or a nucleic acid molecule encoding another KRC family polypeptide.

In other embodiments, a nucleic acid molecule of the invention has at least 70% identity, more preferably 80% identity, and even more preferably 90% identity with a nucleic acid molecule comprising: at least about 300, 400, 500, 600, 700, 800, 900, 1000, 1100, 1200, 1300, 1400 or about 1500 nucleotides of SEQ ID NO: 1 or a nucleic acid molecule encoding another KRC family polypeptide.

Probes based on the KRC nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues, particularly epithelial cells or tissues, particularly epithelial cells or tissues, which misexpress a KRC protein, such as by measuring a level of a KRC-encoding nucleic acid in a sample of cells from a subject e.g., detecting KRC mRNA levels or determining whether a genomic KRC gene has been mutated or deleted.

A nucleic acid fragment encoding a "biologically active portion of a KRC protein" can be prepared by isolating a portion of the nucleotide sequence of SEQ ID NO: 1 or a nucleotide sequence encoding another KRC family polypeptide which encodes a polypeptide having a KRC biological activity (e.g., the ability to modulate proliferation, apoptosis, and/or signaling via an NFkB or JNK signaling pathway), expressing the encoded portion of the KRC protein (e.g., by recombinant expression in vitro) and assessing the activity of the encoded portion of the KRC protein.

Nucleic acid molecules that differ from SEQ ID NO: 1 or a nucleic acid molecule encoding another KRC family polypeptide due to degeneracy of the genetic code, and thus encode the same KRC protein as that encoded by SEQ ID NO: 1 or a nucleic acid molecule encoding another KRC family polypeptide are encompassed by the invention. Accordingly, in another embodiment, an isolated nucleic acid molecule of the invention has a nucleotide sequence encoding a protein having an amino acid sequence shown in SEQ ID NO: 2 or an amino acid sequence of another KRC family polypeptide.

In addition to the KRC nucleotide sequence shown in SEQ ID NO: 1 or a nucleotide sequence encoding another KRC family polypeptide, it will be appreciated by those skilled in the art that DNA sequence polymorphisms that lead to changes in the amino acid sequences of the KRC proteins may exist within a population (e.g., the human population). Such genetic polymorphism in the KRC genes may exist among individuals within a population due to natural allelic variation. As used herein, the terms "gene" and "recombinant gene" refer to nucleic acid molecules which include an open reading frame encoding a KRC protein, preferably a mammalian KRC protein, and can further include non-coding regulatory sequences, and introns. Such natural allelic variations include both functional and non-functional KRC proteins and can typically result in 1-5% variance in the nucleotide sequence of a KRC gene. Any and all such nucleotide variations and resulting amino acid polymorphisms in KRC genes that are the result of natural allelic variation and that do not alter the functional activity of a KRC protein can be used in the claimed methods.

Moreover, nucleic acid molecules encoding other KRC family members and, thus, which have a nucleotide sequence which differs from the KRC family sequence of SEQ ID NO: 1 or a nucleotide sequence encoding another KRC family polypeptide are intended to be within the scope of the invention. Moreover, nucleic acid molecules encoding KRC proteins from different species, and thus which have a nucleotide sequence which differs from the KRC sequence of SEQ ID NO: 1 or a nucleotide sequence encoding another KRC family polypeptide can be used in the claimed methods.

Nucleic acid molecules corresponding to natural allelic variants and homologues of the KRC molecules of the invention can be isolated, e.g., based on their homology to the KRC nucleic acids disclosed herein using the cDNAs disclosed herein, or portions thereof, as a hybridization probe according to standard hybridization techniques. For example, a KRC DNA can be isolated from a human genomic DNA library using all or portion of SEQ ID NO: 1 or a nucleotide sequence encoding another KRC family polypeptide as a hybridization probe and standard hybridization techniques (e.g., as described in Sambrook, J., et al. *Molecular Cloning: A Laboratory Manual. 2nd, ed, Cold Spring Harbor Laboratory*, Cold Spring Harbor, N.Y., 1989). Moreover, a nucleic acid molecule encompassing all or a portion of a KRC gene can be isolated by the polymerase chain reaction using oligonucleotide primers designed based upon the sequence of SEQ ID NO: 1 or a nucleic acid molecule encoding another KRC family polypeptide. For example, mRNA can be isolated from cells (e.g., by the guanidinium-thiocyanate extraction procedure of Chirgwin et al., 1979, *Biochemistry* 18: 5294-5299) and cDNA can be prepared using reverse transcriptase (e.g., Moloney MLV reverse transcriptase, available from Gibco/BRL, Bethesda, MD; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or a nucleic acid molecule encoding another KRC family polypeptide. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a KRC nucleotide sequence can be prepared by standard synthetic techniques, e.g., using an automated DNA synthesizer.

In another embodiment, an isolated nucleic acid molecule of the invention can be identified based on shared nucleotide sequence identity using a mathematical algorithm. Such algorithms are outlined in more detail below.

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO: 1 or a nucleotide sequence encoding another KRC family polypeptide or its complement. In other embodiment, the nucleic acid molecule is at least 30, 50, 100, 150, 200, 250, 300, 350, 400, 450, 500, 550, or 600 nucleotides in length. As used herein, the term "hybridizes under stringent" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 450° C., followed by one or more washes in 0.2 ×SSC, 0.1% SDS at 50-650° C. Preferably, an isolated nucleic acid molecule of the invention that hybridizes under stringent conditions to the sequence of SEQ ID NO: 1 or a nucleic acid molecule encoding another KRC family polypeptide or its complement corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the KRC nucleotide sequences shown in SEQ ID NO: 1 or a nucleic acid molecule encoding another KRC family polypeptide it will be appreciated by those skilled in the art that DNA sequence polymorphisms that lead to minor changes in the nucleotide or amino acid sequences of a KRC may exist within a population. Such genetic polymorphism in a KRC gene may exist among individuals within a population due to natural allelic variation. Such natural allelic variations can typically result in 1-2 % variance in the nucleotide sequence of the gene. Such nucleotide variations and resulting amino acid polymorphisms in a KRC that are the result of natural allelic variation and that do not alter the functional activity of a KRC polypeptide are within the scope of the invention.

In addition to naturally-occurring allelic variants of KRC sequences that may exist in the population, the skilled artisan will further appreciate that minor changes may be introduced by mutation into nucleotide sequences, e.g., of SEQ ID NO: 1 or a nucleic acid molecule encoding another KRC family polypeptide, thereby leading to changes in the amino acid sequence of the encoded protein, without altering the functional activity of a KRC protein. For example, nucleotide substitutions leading to amino acid substitutions at "non-essential" amino acid residues may be made in the sequence of SEQ ID NO: 1 or a nucleic acid molecule encoding another KRC family polypeptide. A "non-essential" amino acid residue is a residue that can be altered from the wild-type sequence of a KRC nucleic acid molecule (e.g., the sequence of SEQ ID NO: 1 or a nucleic acid molecule encoding another KRC family polypeptide) without altering the functional activity of a KRC molecule. Exemplary residues which are non-essential and, therefore, amenable to substitution, can be identified by one of ordinary skill in the art by performing an amino acid alignment of KRC-related molecules and determining residues that are not conserved. Such residues, because they have not been conserved, are more likely amenable to substitution.

Accordingly, another aspect of the invention pertains to nucleic acid molecules encoding KRC proteins that contain changes in amino acid residues that are not essential for a KRC activity. Such KRC proteins differ in amino acid sequence from SEQ ID NO: 2 or an amino acid sequence of another KRC family polypeptide yet retain an inherent KRC activity. An isolated nucleic acid molecule encoding a non-natural variant of a KRC protein can be created by introducing one or more nucleotide substitutions, additions or deletions into the nucleotide sequence of SEQ ID NO: 1 or a nucleic acid molecule encoding another KRC family polypeptide such that one or more amino acid substitutions, additions or deletions are introduced into the encoded protein. Mutations can be introduced into SEQ ID NO: 1 or a nucleic acid molecule encoding another KRC family polypeptide by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a KRC is preferably replaced with another amino acid residue from the same side chain family.

Alternatively, in another embodiment, mutations can be introduced randomly along all or part of a KRC coding sequence, such as by saturation mutagenesis, and the resultant mutants can be screened for their ability to bind to DNA and/or activate transcription, to identify mutants that retain functional activity. Following mutagenesis, the encoded a KRC mutant protein can be expressed recombinantly in a host cell and the functional activity of the mutant protein can be determined using assays available in the art for assessing a KRC activity.

Yet another aspect of the invention pertains to isolated nucleic acid molecules encoding a KRC fusion proteins. Such nucleic acid molecules, comprising at least a first nucleotide sequence encoding a full-length KRC protein, polypeptide or peptide having a KRC activity operatively linked to a second nucleotide sequence encoding a non- KRC protein, polypeptide or peptide, can be prepared by standard recombinant DNA techniques.

In a preferred embodiment, a mutant KRC protein can be assayed for KRC activity as described herein.

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the KRC protein is derived, or substantially free from chemical precursors or other chemicals when chemically synthesized. The language "substantially free of cellular material" includes preparations of KRC protein in which the protein is separated from cellular components of the cells from which it is isolated or recombinantly produced.

Isolated KRC proteins, and biologically active portions thereof can also be used as modulating agents, as well as polypeptide fragments suitable for use as immunogens to raise anti-KRC antibodies. In one embodiment, native KRC proteins can be isolated from cells or tissue sources by an appropriate purification scheme using standard protein purification techniques. In another embodiment, KRC proteins are produced by recombinant DNA techniques. Alternative to recombinant expression, a KRC protein or polypeptide can be synthesized chemically using standard peptide synthesis techniques. It will be understood that in discussing the uses of KRC proteins (e.g., as shown in SEQ. ID NO:2 or an amino acid sequence encoding another KRC family polypeptide), that fragments of such proteins that are not full length KRC polypeptides (e.g., that comprise one or more KRC domains, e.g a domain comprising amino acid residues corresponding to residues 204-1055 of SEQ ID NO:2) are included.

Another aspect of the invention pertains to isolated KRC proteins. Preferably, the KRC proteins comprise the amino acid sequence encoded by SEQ ID NO: 1 or a nucleotide sequence encoding another KRC family polypeptide or a portion thereof. In another preferred embodiment, the protein comprises the amino acid sequence of SEQ ID NO: 2 or an amino acid sequence of another KRC family polypeptide or a portion thereof. In other embodiments, the protein has at least 50%, at least 60 % amino acid identity, more preferably 70% amino acid identity, more preferably 80%, and even more preferably, 90% or 95% amino acid identity with the amino acid sequence shown in SEQ ID NO: 2 or an amino acid sequence of another KRC family polypeptide or a portion thereof, e.g., the consensus domains set forth above.

Preferred portions of KRC polypeptide molecules are biologically active, i.e., encode a portion of the KRC polypeptide having the ability to modulate cell survival, proliferation, differentiation and/or motility. Preferably, the cell is a T cell, e.g., a Th1 cell.

Biologically active portions of a KRC protein include peptides comprising amino acid sequences sufficiently homologous to or derived from the amino acid sequence of the KRC protein, which include less amino acids than the full length KRC proteins, and exhibit at least one activity of a KRC protein.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity =# of identical positions/total # of positions×100). The percent identity between the two sequences is a function of the number of identical positions shared by the sequences, taking into account the number of gaps, and the length of each gap, which are introduced for optimal alignment of the two sequences. As used herein amino acid or nucleic acid "identity " is equivalent to amino acid or nucleic acid "homology ".

The comparison of sequences and determination of percent identity between two sequences can be accomplished using a mathematical algorithm. A non-limiting example of a mathematical algorithm utilized for comparison of sequences is the algorithm of Karlin and Altschul, 1990, *Proc. Nail. Acad. Sci*. USA 87:2264, modified as in Karlin and Altschul, 1993, *Proc. Nail. Acad. Sci*. USA 90:5 873. Such an algorithm is incorporated into the NBLAST and XBLAST programs (version 2.0) of Altschul, et al., 1990, *J. Mol. Biol*. 215:403. BLAST nucleotide searches can be performed with the NBLAST program score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., 1997, *Nucleic Acids Research* 25(17):3389. When utilizing BLAST and Gapped BLAST programs, the default parameters of the respective programs (e.g., XBLAST and NBLAST) can be used. See www.ncbi.nlm.nih.gov. Another preferred, non-limiting algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a mathematical algorithm utilized for the alignment of protein sequences is the Lipman-Pearson algorithm (Lipman and Pearson, 1985, *Science* 227:1435). When using the Lipman-Pearson algorithm, a PAM250 weight residue table, a gap length penalty of 12, a gap penalty of 4, and a Kutple of 2 can be used. A preferred, non-limiting example of a mathematical algorithm utilized for the alignment of nucleic acid sequences is the Wilbur-Lipman algorithm (Wilbur and Lipman, 1983, *Proc. Nati. Acad. Sci. USA* 80:726). When using the Wilbur-Lipman algorithm, a window of 20, gap penalty of 3, Ktuple of 3 can be used. Both the Lipman-Pearson algorithm and the Wilbur- Lipman algorithm are incorporated, for example, into the MEGALIGN program (e.g., version 3.1.7) which is part of the DNASTAR sequence analysis software package.

Additional algorithms for sequence analysis are known in the art, and include ADVANCE and ADAM., described in Torelli and Robotti, 1994, *Comput. Appi. Biosci.* 10:3; and FASTA, described in Pearson and Lipman, 1988, *Proc. Nati. Acad. Sci. USA* 85:2444.

In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2,3,4, 5, or 6.

Protein alignments can also be made using the Geneworks global protein alignment program (e.g., version 2.5.1) with the cost to open gap set at 5, the cost to lengthen gap set at 5, the minimum diagonal length set at 4, the maximum diagonal offset set at 130, the consensus cutoff set at 50% and utilizing the Pam 250 matrix.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al., 1990, *J Mol. Biol.* 215:403-10. BLAST nucleotide searches can be performed with the NBLAST program, score=100, wordlength= 12 to obtain nucleotide sequences homologous to KRC nucleic acid molecules of the invention. BLAST protein searches can be performed with the XBLAST program, score=50, wordlength=3 to obtain amino acid sequences homologous to KRC protein molecules of the invention. To obtain gapped alignments for comparison purposes, Gapped BLAST can be utilized as described in Altschul et al., 1997, *Nucleic Acids Res.* 25(17):3389-3402. When utilizing BLAST and Gapped BLAST programs, the default parameters of the respective programs (e.g., XBLAST and NIBLAST) can be used. For example, the nucleotide sequences of the invention can be analyzed using the default BLASTN matrix 1-3 with gap penalties set at: existence 11 and extension 1. The amino acid sequences of the invention can be analyzed using the default settings: the Blosum62 matrix with gap penalties set at existence 11 and extension 1.

The invention also provides KRC chimeric or fusion proteins. As used herein, a KRC "chimeric protein" or "fusion protein" comprises a KRC polypeptide operatively linked to a non-KRC polypeptide. An "KRC polypeptide" refers to a polypeptide having an amino acid sequence corresponding to KRC polypeptide, whereas a "non-KRC polypeptide " refers to a polypeptide having an amino acid sequence corresponding to a protein which is not substantially homologous to the KRC protein, e.g., a protein which is different from the KRC protein and which is derived from the same or a different organism. Within a KRC fusion protein the KRC polypeptide can correspond to all or a portion of a KRC protein. In a preferred embodiment, a KRC fusion protein comprises at least one biologically active portion of a KRC protein, e.g., a KRC consensus domain. Within the fusion protein, the term "operatively linked " is intended to indicate that the KRC polypeptide and the non-KRC polypeptide are fused in-frame to each other. The non-KRC polypeptide can be fused to the N-terminus or C-terminus of the KRC polypeptide.

For example, in one embodiment, the fusion protein is a GST-KRC member fusion protein in which the KRC member sequences are fused to the C-terminus of the GST sequences. In another embodiment, the fusion protein is a KRC -HA fusion protein in which the KRC member nucleotide sequence is inserted in a vector such as pCEP4-HA vector (Herrscher, R. F. et al., 1995, *Genes Dev.* 9:3067-3082) such that the KRC member sequences are fused in frame to an influenza haemagglutinin epitope tag. Such fusion proteins can facilitate the purification of a recombinant KRC member.

Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a KRC fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A KRC encoding nucleic acid can be cloned into such an expression vector such that the fusion moiety is linked in-frame to the KRC protein.

In another embodiment, the fusion protein is a KRC protein containing a heterologous signal sequence at its N-terminus. In certain host cells (e.g., mammalian host cells), expression and/or secretion of KRC can be increased through use of a heterologous signal sequence. The KRC fusion proteins of the invention can be incorporated into pharmaceutical compositions and administered to a subject in vivo. Use of KRC fusion proteins may be useful therapeutically for the treatment of disorders, e.g., as soluble antagonists of the KRC ligand. Disorders that would benefit from such treatment include, e.g. cancer or Alzheimer's disease. Such Fc fusion proteins can be used as soluble antagonists of the KRC ligand. Moreover, the KRC-fusion proteins of the invention can be used as immunogens to produce anti- KRC antibodies in a subject.

Preferably, a KRC chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A KRC-encoding nucleic acid can be cloned into such an expression vector such that the fusion moiety is linked in-frame to the KRC protein.

In one embodiment, a KRC-Fc fusion protein can be made using techniques that are known in the art. For example, as taught in the instant examples, a soluble KRC-Fc fusion protein can be constructed by joining the cDNA sequence encoding the extracellular region of KRC to the hinge-$C_H2$-$C_H3$ regions of human immunoglobulin (Ig). Any isotype may be used in making such a construct, for example, Fc γ1, γ2, γ3, ε or α. Cells can be transfected with a plasmid carrying the KRC-Ig construct, cultured, and conditioned medium harvested. The fusion protein can then be purified, e.g., using a column of immobilized protein A.

The nucleic acids of the invention can be prepared by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Preferably a host cell is a mammalian cell, e.g., a human cell. In particularly preferred embodiments, it is a epithelial cell.

As used herein, the term "transgenic cell" refers to a cell containing a transgene.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "rodent" refers to all members of the phylogenetic order Rodentia.

As used herein, the term "misexpression" includes a non-wild type pattern of gene expression. Expression as used herein includes transcriptional, post transcriptional, e.g., mRNA stability, translational, and post translational stages. Misexpression includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-translational modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or non-expression of a gene or transgene, e.g., that can be induced by a deletion of all or part of the gene or its control sequences.

As used herein, the term "knockout" refers to an animal or cell therefrom, in which the insertion of a transgene disrupts an endogenous gene in the animal or cell therefrom. This disruption can essentially eliminate KRC in the animal or cell.

In preferred embodiments, misexpression of the gene encoding the KRC protein is caused by disruption of the KRC gene. For example, the KRC gene can be disrupted through removal of DNA encoding all or part of the protein.

In preferred embodiments, the animal can be heterozygous or homozygous for a misexpressed KRC gene, e.g., it can be a transgenic animal heterozygous or homozygous for a KRC transgene.

In preferred embodiments, the animal is a transgenic mouse with a transgenic disruption of the KRC gene, preferably an insertion or deletion, which inactivates the gene product.

In another aspect, the invention features, a nucleic acid molecule which, when introduced into an animal or cell, results in the misexpression of the KRC gene in the animal or cell. In preferred embodiments, the nucleic acid molecule, includes an KRC nucleotide sequence which includes a disruption, e.g., an insertion or deletion and preferably the insertion of a marker sequence. The nucleotide sequence of the wild type KRC is known in the art and described in, for example, Mak, C. H., et al. (1998) *Immunogenetics* 48:32-39, the contents of which are incorporated herein by reference.

As used herein, the term "marker sequence" refers to a nucleic acid molecule that (a) is used as part of a nucleic acid construct (e.g., the targeting construct) to disrupt the expression of the gene of interest (e.g., the KRC gene) and (b) is used to identify those cells that have incorporated the targeting construct into their genome. For example, the marker sequence can be a sequence encoding a protein which confers a detectable trait on the cell, such as an antibiotic resistance gene, e.g., neomycin resistance gene, or an assayable enzyme not typically found in the cell, e.g., alkaline phosphatase, horseradish peroxidase, luciferase, beta-galactosidase and the like.

As used herein, "disruption of a gene" refers to a change in the gene sequence, e.g., a change in the coding region. Disruption includes: insertions, deletions, point mutations, and rearrangements, e.g., inversions. The disruption can occur in a region of the native KRC DNA sequence (e.g., one or more exons) and/or the promoter region of the gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is a disruption. Preferred disruptions reduce KRC levels to about 50% of wild type, in heterozygotes or essentially eliminate KRC in homozygotes.

As used herein, the term "antibody" is intended to include immunoglobulin molecules and immunologically active portions of immunoglobulin molecules, i.e., molecules that contain an antigen binding site which binds (immunoreacts with) an antigen, such as Fab and F(ab')$_2$ fragments, single chain antibodies, intracellular antibodies, scFv, Fd, or other fragments. Preferably, antibodies of the invention bind specifically or substantially specifically to KRC, TRAF, c-Jun or c-Fos molecules (i.e., have little to no cross reactivity with non-KRC, non-TRAF, non-c-Jun or non-c-Fos molecules). The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used herein, the term "disorders that would benefit from the modulation of KRC activity or expression" or "KRC associated disorder" includes disorders in which KRC activity is aberrant or which would benefit from modulation of a KRC activity. Preferably, KRC associated disorders involve aberrant proliferation of cells, e.g., excessive or unwanted proliferation of cells or deficient proliferation of cells. In one embodiment, KRC associated disorders are disorders such as inflammation. Examples of KRC associated disorders include: disorders involving aberrant or unwanted proliferation of cells, e.g., inflammation, autoimmunity, neoplasia, or cell death, e.g., apoptosis, or necrosis. Further examples of KRC associated disorders include carcinomas, adenocarcinomas, and other neoplasias. KRC disorders may also include disorders that have been linked generally to aberrant TNF receptor activity or function, including Crohn's Disease (Baert and Rutgeerts, 1999, *Int J Colorectal Dis*, 14:47-51) and certain cardiovascular diseases (Ferrari, 1999, *Pharmacol Res*, 40:97-105). They may also include disorders characterized by uncontrolled or aberrant levels of apoptosis, for example myelokathexis (Aprikyan et al., 2000, *Blood*, 95:320-327), and autoimmune lymphoproliferative syndrome (Jackson and Puck, 1999, *Curr Op Pediatr*, 11:521-527; Straus et al., 1999, *Ann Intern Med*, 130:591-601).

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation.

Various aspects of the invention are described in further detail below:

II. Screening Assays to Identify KRC Modulating Agents

Modulators of KRC activity can be known (e.g., dominant negative inhibitors of KRC activity, antisense KRC intracellular antibodies that interfere with KRC activity, peptide inhibitors derived from KRC) or can be identified using the methods described herein. The invention provides methods (also referred to herein as "screening assays") for identifying other modulators, i.e., candidate or test compounds or agents (e.g., peptidomimetics, small molecules or other drugs) which modulate KRC activity and for testing or optimizing the activity of other agents.

For example, in one embodiment, molecules which bind, e.g., to KRC or a molecule in a signaling pathway involving KRC (e.g., TRAF, NF-kB, JNK, or AP-1)or have a stimulatory or inhibitory effect on the expression and or activity of KRC or a molecule in a signal transduction pathway involving KRC can be identified. For example, c-Jun, NF-kB, TRAF, and JNK function in a signal transduction pathway involving KRC, therefore, any of these molecules can be used in the subject screening assays. Although the specific embodiments described below in this section and in other sections may list one of these molecules as an example, other molecules in a signal transduction pathway involving KRC can also be used in the subject screening assays.

In one embodiment, the ability of a compound to directly modulate the expression, post-translational modification (e.g., phosphorylation), or activity of KRC is measured in an indicator composition using a screening assay of the invention.

The indicator composition can be a cell that expresses the KRC protein or a molecule in a signal transduction pathway involving KRC, for example, a cell that naturally expresses or, more preferably, a cell that has been engineered to express the protein by introducing into the cell an expression vector encoding the protein. Preferably, the cell is a mammalian cell, e.g., a human cell. In one embodiment, the cell is a T cell.

Alternatively, the indicator composition can be a cell-free composition that includes the protein (e.g., a cell extract or a composition that includes e.g., either purified natural or recombinant protein).

Compounds identified using the assays described herein can be useful for treating disorders associated with aberrant expression, post-translational modification, or activity of KRC or a molecule in a signaling pathway involving KRC e.g: disorders that would benefit from modulation of TNFα production, modulation of IL-2 production, modulation of a JNK signaling pathway, modulation of an NFkB signaling pathway, modulation of AP-1 activity, modulation of Ras and Rac activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, or modulation of T cell differentiation.

Conditions that can benefit from modulation of a signal transduction pathway involving KRC include autoimmune disorders as well as malignancies and immunodeficiency disorders. Compounds which modulate KRC expression and/or activity can also be used to modulate the immune response.

The subject screening assays can be performed in the presence or absence of other agents. In one embodiment, the subject assays are performed in the presence of an agent that provides a T cell receptor-mediated signal.

In another aspect, the invention pertains to a combination of two or more of the assays described herein. For example, a modulating agent can be identified using a cell-based or a cell-free assay, and the ability of the agent to modulate the activity of KRC or a molecule in a signal transduction pathway involving KRC can be confirmed in vivo, e.g., in an animal such as an animal model for multiple myeloma, neoplastic diseases, renal cell carcinoma or autoimmune diseases.

Moreover, a modulator of KRC or a molecule in a signaling pathway involving KRC identified as described herein (e.g., an antisense nucleic acid molecule, or a specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate the activity and/or expression of KRC e.g., by performing screening assays such as those described above using molecules with which KRC interacts, e.g., molecules that act either upstream or downstream of KRC in a signal transduction pathway.

The cell based and cell free assays of the invention are described in more detail below.

A. Cell Based Assays

The indicator compositions of the invention can be cells that expresses a KRC protein or non-KRC protein in the KRC signaling pathway (such as, e.g., TRAF, NF-kB, JNK, Jun, or AP-1) for example, a cell that naturally expresses endogenous KRC or, more preferably, a cell that has been engineered to express an exogenous KRC, TRAF, NF-kB, JNK, Jun, or AP-1 protein by introducing into the cell an expression vector encoding the protein. Alternatively, the indicator composition can be a cell-free composition that includes KRC or a non-KRC protein such as TRAF, NF-kB, JNK, Jun, or AP-1 (e.g., a cell extract from a cell expressing the protein or a composition that includes purified KRC, TRAF, NF-kB, JNK, Jun, or AP-1 protein, either natural or recombinant protein).

Compounds that modulate expression and/or activity of KRC, or a non-KRC protein that acts upstream or downstream of can be identified using various "read-outs."

For example, an indicator cell can be transfected with an expression vector, incubated in the presence and in the absence of a test compound, and the effect of the compound on the expression of the molecule or on a biological response regulated by can be determined. The biological activities of include activities determined in vivo, or in vitro, according to standard techniques. Activity can be a direct activity, such as an association with -target molecule (e.g., a protein such as the Jun or TRAF protein. Alternatively, activity is an indirect activity, such as a cellular signaling activity occurring downstream of the interaction of the protein with an target molecule or a biological effect occurring as a result of the signaling cascade triggered by that interaction. For example, biological activities of KRC described herein include: modulation of TNFα production, modulation of IL-2 production, modulation of a JNK signaling pathway, modulation of an NFkB signaling pathway, modulation of AP-1 activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, or modulation of T cell differentiation.

To determine whether a test compound modulates protein expression, in vitro transcriptional assays can be performed. In one example of such an assay, a regulatory sequence (eg., the full length promoter and enhancer) of KRC can be operably linked to a reporter gene such as chloramphenicol acetyltransferase (CAT) or luciferase and introduced into host cells. Other techniques are known in the art.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired protein in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of protein desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as an indicator cell in the screening assay. Preferably a cell line is used which expresses low levels of endogenous KRC (or, e.g., TRAF, Jun) and is then engineered to express recombinant protein. Cells for use in the subject assays include both eukaryotic and prokaryotic cells. For example, in one embodiment, a cell is a bacterial cell. In another embodiment, a cell is a fungal cell, such as a yeast cell. In another embodiment, a cell is a vertebrate cell, e.g., an avian cell or a mammalian cell (e.g., a murine cell, or a human cell).

In one embodiment, the level of expression of the reporter gene in the indicator cell in the presence of the test compound is higher than the level of expression of the reporter gene in the indicator cell in the absence of the test compound and the test compound is identified as a compound that stimulates the expression of KRC (or, e.g., TRAF, Jun). In another embodiment, the level of expression of the reporter gene in the indicator cell in the presence of the test compound is lower than the level of expression of the reporter gene in the indicator cell in the absence of the test compound and the test compound is identified as a compound that inhibits the expression of KRC (or, e.g., TRAF, Jun).

In one embodiment, the invention provides methods for identifying compounds that modulate cellular responses in which KRC is involved.

In one embodiment differentiation of cells, e.g., T cells, can be used as an indicator of modulation of KRC or a signal transduction pathway involving KRC. Cell differentiation can be monitored directly (e.g. by microscopic examination of the cells for monitoring cell differentiation), or indirectly, e.g., by monitoring one or more markers of cell differentiation (e.g., an increase in mRNA for a gene product associated with cell differentiation, or the secretion of a gene product associated with cell differentiation, such as the secretion of a protein (e.g., the secretion of cytkines) or the expression of a cell surface marker (such as CD69). Standard methods for detecting mRNA of interest, such as reverse transcription-polymerase chain reaction (RT-PCR) and Northern blotting, are known in the art. Standard methods for detecting protein secretion in culture supernatants, such as enzyme linked immunosorbent assays (ELISA), are also known in the art. Proteins can also be detected using antibodies, e.g., in an immunoprecipitation reaction or for staining and FACS analysis.

In another embodiment, the ability of a compound to modulate effector T cell function can be determined. For example, in one embodiment, the ability of a compound to modulate T cell proliferation, cytokine production, and/or cytotoxicity can be measured using techniques well known in the art.

In one embodiment, the ability of a compound to modulate IL-2 production can be determined. Production of IL-2 can be monitored, for example, using Northern or Western blotting. IL-2 can also be detected using an ELISA assay or in a bioassay, e.g., employing cells which are responsive to IL-2 (e.g., cells which proliferate in response to the cytokine or which survive in the presence of the cytokine) using standard techniques.

In another embodiment, the ability of a compound to modulate apoptosis can be determined. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other exemplary assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay. In another embodiment, the transcription of genes associated with a cell signaling pathway involved in apoptosis (e.g., JNK) can be detected using standard methods.

In another embodiment, mitochondrial inner membrane permeabilization can be measured in intact cells by loading the cytosol or the mitochondrial matrix with a die that does not normally cross the inner membrane, e.g., calcein (Bernardi et al. 1999. Eur. J. Biochem. 264:687; Lemasters, J., J. et al. 1998. Biochem. Biophys. Acta 1366:177. In another embodiment, mitochondrial inner membrane permeabilization can be assessed, e.g., by determining a change in the mitochondrial inner membrane potential ($\Delta\Psi m$). For example, cells can be incubated with lipophilic cationic fluorochromes such as DiOC6 (Gross et al. 1999. Genes Dev. 13:1988) (3,3'dihexyloxacarbocyanine iodide) or JC-1 (5,5', 6,6'-tetrachloro-1,1', 3,3'-tetraethylbenzimidazolylcarbocyanine iodide). These dyes accumulate in the mitochondrial matrix, driven by the $\Psi m$. Dissipation results in a reduction of the fluorescence intensity (e.g., for DiOC6 (Gross et al. 1999. Genes Dev. 13:1988) or a shift in the emission spectrum of the dye. These changes can be measured by cytofluorometry or microscopy.

In yet another embodiment, the ability of a compound to modulate translocation of KRC to the nucleus can be determined. Translocation of KRC to the nucleus can be measured, e.g., by nuclear translocation assays in which the emission of two or more fluorescently-labeled species is detected simultaneously. For example, the cell nucleus can be labeled with a known fluorophore specific for DNA, such as Hoechst 33342. The KRC protein can be labeled by a variety of methods, including expression as a fusion with GFP or contacting the sample with a fluorescently-labeled antibody specific for KRC. The amount KRC that translocates to the nucleus can be determined by determining the amount of a first fluorescently-labeled species, i.e., the nucleus, that is distributed in a correlated or anti-correlated manner with respect to a second fluorescently-labeled species, i.e., KRC, as described in U.S. Pat. No. 6,400,487, the contents of which are hereby incorporated by reference.

In one embodiment, the effect of a compound on a JNK signaling pathway can be determined. The JNK group of MAP kinases is activated by exposure of cells to environmental stress or by treatment of cells with pro-inflammatory cytokines. A combination of studies involving gene knockouts and the use of dominant-negative mutants have implicated both MKK4 and MKK7 in the phosphorylation and activation of JNK. Targets of the JNK signal transduction pathway include the transcription factors ATF2 and c-Jun. JNK binds to an $NH_2$-terminal region of ATF2 and c-Jun and phosphorylates two sites within the activation domain of each transcription factor, leading to increased transcriptional activity. JNK is activated by dual phosphorylation on Thr-183 and Tyr-185. To determine the effect of a compound on a JNK signal transduction pathway, the ability of the compound to modulate the activation status of various molecules in the signal transduction pathway can be determined using standard techniques. For example, in one embodiment, the phosphorylation status of JNK can be examined by immunoblotting with the anti-ACTIVE-JNK antibody (Promega), which specifically recognizes the dual phosphorylated TPY motif.

In another embodiment, the effect of a compound on an NFkB signal transduction pathway can be determined. The ability of the compound to modulate the activation status of various components of the NFkB pathway can be determined using standard techniques. NFkB constitutes a family of Rel domain-containing transcription factors that play essential roles in the regulation of inflammatory, anti-apoptotic, and immune responses. The function of the NFkB/Rel family members is regulated by a class of cytoplasmic inhibitory proteins termed IBs that mask the nuclear localization domain of NFkB causing its retention in the cytoplasm. Activation of NFkB by TNF-α and IL-1 involves a series of signaling intermediates, which may converge on the NFkB-inducing kinase (NIK). This kinase in turn activates the IB kinase (IKK) isoforms. These IKKs phosphorylate the two regulatory serines located in the N termini of IB molecules, triggering rapid ubiquitination and degradation of IB in the 26S proteasome complex. The degradation of IB unmasks a nuclear localization signal present in the NFkB complex, allowing its rapid translocation into the nucleus, where it engages cognate B enhancer elements and modulates the transcription of various NFkB-responsive target genes. In one embodiment, the ability of a compound to modulate one or more of: the status of NFkB inhibitors, the ability of NFkB to translocate to the nucleus, or the activation of NFkB dependent gene transcription can be measured.

In one embodiment, the ability of a compound to modulate AP-1 activity can be measured. The AP-1 complex is comprised of the transcription factors Fos and Jun. The AP-1 complex activity is controlled by regulation of Jun and Fos transcription and by posttranslation modification, for example, the activation of several MAPKS, ERK, p38 and JN, is required for AP-1 transcriptional activity. In one embodiment, the modulation of transcription mediated by AP-1 can be measured. In another embodiment, the ability of a compound to modulate the activity of AP-1, e.g., by modulating its phosphorylation or its ubiquitination can be measured. In one embodiment, the ubiquitination of AP-1 can be measured using techniques known in the art. In another embodiment, the degradation of AP-1 (or of c-Jun and/or c-Fos) can be measured using known techniques.

The loss of AP-1 has been associated with T cell anergy. Accordingly, in one embodiment, the ability of a test compound to modulate T cell anergy can be determined, e.g, by assaying secondary T cell responses. If the T cells are unresponsive to the secondary activation attempts, as determined by IL-2 synthesis and/or T cell proliferation, a state of anergy or has been induced. Standard assay procedures can be used to measure T cell anergy, for example, T cell proliferation can be measured, for example, by assaying [$^3$H] thymidine incorporation. In another embodiment, signal transduction can be measured, e.g., activation of members of the MAP kinase cascade or activation of the AP-1 complex can be measured. In another embodiment, intracellular calcium mobilization, protein levels members of the NFAT cascade can be measured.

In another embodiment, the effect of a compound on Ras and Rac activity can be measured using standard techniques. In one embodiment, actin polymerization, e.g., by measuring the immunofluorescence of F-actin can be measured.

The ability of the test compound to modulate KRC (or a molecule in a signal transduction pathway involving to KRC) binding to a substrate or target molecule (e.g., TRAF or Jun in the case of KRC ) can also be determined. Determining the ability of the test compound to modulate KRC binding to a target molecule (e.g., a binding partner such as a substrate) can be accomplished, for example, by coupling the target molecule with a radioisotope or enzymatic label such that binding of the target molecule to KRC or a molecule in a signal transduction pathway involving KRC can be determined by detecting the labeled KRC target molecule in a complex. Alternatively, KRC be coupled with a radioisotope or enzymatic label to monitor the ability of a test compound to modulate KRC binding to a target molecule in a complex. Determining the ability of the test compound to bind to KRC can be accomplished, for example, by coupling the compound with a radioisotope or enzymatic label such that binding of the compound to KRC can be determined by detecting the labeled compound in a complex. For example, targets can be labeled with $^{125}$I, $^{35}$S, $^{14}$C, or $^3$H, either directly or indirectly, and the radioisotope detected by direct counting of radioemmission or by scintillation counting. Alternatively, compounds can be labeled, e.g., with, for example, horseradish peroxidase, alkaline phosphatase, or luciferase, and the enzymatic label detected by determination of conversion of an appropriate substrate to product.

In another embodiment, the ability of KRC or a molecule in a signal transduction pathway involving KRC to be acted on by an enzyme or to act on a substrate can be measured. For example, in one embodiment, the effect of a compound on the phosphorylation of KRC can be measured using techniques that are known in the art.

It is also within the scope of this invention to determine the ability of a compound to interact with KRC or a molecule in a signal transduction pathway involving KRC without the labeling of any of the interactants. For example, a microphysiometer can be used to detect the interaction of a compound with a KRC molecule without the labeling of either the compound or the molecule (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and Exemplary target molecules of KRC include: Jun and TRAF (e.g., TRAF2).

In another embodiment, a different (i.e., non-KRC) molecule acting in a pathway involving KRC that acts upstream or downstream of KRC can be included in an indicator composition for use in a screening assay. Compounds identified in a screening assay employing such a molecule would also be useful in modulating KRC activity, albeit indirectly. For example, the ability of TRAF (e.g., TRAF2) to activate NFKβ dependent gene expression can be measured.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

The cells of the invention can express endogenous or another protein in a signaling pathway involving or can be engineered to do so. For example, a cell that has been engineered to express the protein and/or a non protein which acts upstream or downstream of can be produced by introducing into the cell an expression vector encoding the protein.

Recombinant expression vectors that can be used for expression of KRC or a molecule in a signal transduction pathway involving KRC (e.g., a protein which acts upstream or downstream of KRC ) are known in the art. For example, the cDNA is first introduced into a recombinant expression vector using standard molecular biology techniques. A cDNA can be obtained, for example, by amplification using the polymerase chain reaction (PCR) or by screening an appropriate cDNA library. The nucleotide sequences of cDNAs for or a molecule in a signal transduction pathway involving (e.g., human, murine and yeast) are known in the art and can be used for the design of PCR primers that allow for amplification of a cDNA by standard PCR methods or for the design of a hybridization probe that can be used to screen a cDNA library using standard hybridization methods.

Following isolation or amplification of a cDNA molecule encoding KRC or a non-KRC molecule in a signal transduction pathway involving KRC the DNA fragment is introduced into an expression vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule in a form suitable for expression of the nucleic acid in a host cell, which means that the recombinant expression vectors include one or more regulatory sequences, selected on the basis of the host cells to be used for expression and the level of expression desired, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell, those which direct expression of the nucleotide sequence only in certain host cells (e.g., tissue-specific regulatory sequences) or those which direct expression of the nucleotide sequence only under certain conditions (e.g., inducible regulatory sequences).

When used in mammalian cells, the expression vector's control functions are often provided by viral regulatory elements. For example, commonly used promoters are derived from polyoma virus, adenovirus, cytomegalovirus and Simian Virus 40. Non-limiting examples of mammalian expression vectors include pCDM8 (Seed, B., (1987) *Nature* 329: 840) and pMT2PC (Kaufman et al. (1987), *EMBO J.* 6:187-195). A variety of mammalian expression vectors carrying different regulatory sequences are commercially available.

For constitutive expression of the nucleic acid in a mammalian host cell, a preferred regulatory element is the cytomegalovirus promoter/enhancer. Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad Sci. USA* 89:5547-5551; Gossen, M. et al. (1995) *Science* 268:1766-1769; PCT Publication No. WO 94/29442; and PCT Publication No. WO 96/01313). Still further, many tissue-specific regulatory sequences are known in the art, including the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916) and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

Vector DNA can be introduced into mammalian cells via conventional transfection techniques. As used herein, the various forms of the term "transfection" are intended to refer to a variety of art-recognized techniques for introducing foreign nucleic acid (e.g., DNA) into mammalian host cells, including calcium phosphate co-precipitation, DEAE-dextran-mediated transfection, lipofection, or electroporation. Suitable methods for transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on a separate vector from that encoding KRC or, more preferably, on the same vector. Cells stably transfected with the introduced nucleic acid can be identified by drug selection (e.g., cells that have incorporated the selectable marker gene will survive, while the other cells die).

In one embodiment, within the expression vector coding sequences are operatively linked to regulatory sequences that allow for constitutive expression of the molecule in the indicator cell (e.g., viral regulatory sequences, such as a cytomegalovirus promoter/enhancer, can be used). Use of a recombinant expression vector that allows for constitutive expression of KRC or a molecule in a signal transduction pathway involving KRC in the indicator cell is preferred for identification of compounds that enhance or inhibit the activity of the molecule. In an alternative embodiment, within the expression vector the coding sequences are operatively linked to regulatory sequences of the endogenous gene for KRC or a molecule in a signal transduction pathway involving KRC (i.e., the promoter regulatory region derived from the endogenous gene). Use of a recombinant expression vector in which expression is controlled by the endogenous regulatory sequences is preferred for identification of compounds that enhance or inhibit the transcriptional expression of the molecule.

In yet another aspect of the invention, the KRC protein or fragments thereof can be used as "bait protein" e.g., in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with KRC ("binding proteins" or "bp") and are involved in KRC activity. Such KRC-binding proteins are also likely to be involved in the propagation of signals by the KRC proteins or KRC targets such as, for example, downstream elements of an KRC-mediated signaling pathway. Alternatively, such KRC-binding proteins can be KRC inhibitors.

The two-hybrid system is based on the modular nature of most transcription factors, which consist of separable DNA-binding and activation domains. Briefly, the assay utilizes two different DNA constructs. In one construct, the gene that codes for an KRC protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an KRC dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the KRC protein or a molecule in a signal transduction pathway involving KRC.

B. Cell-Free Assays

In another embodiment, the indicator composition is a cell free composition. KRC or a non-KRC protein in a signal transduction pathway involving KRC expressed by recombinant methods in a host cells or culture medium can be isolated from the host cells, or cell culture medium using standard methods for protein purification. For example, ion-exchange chromatography, gel filtration chromatography, ultrafiltration, electrophoresis, and immunoaffinity purification with antibodies can be used to produce a purified or semi-purified protein that can be used in a cell free composition. Alternatively, a lysate or an extract of cells expressing the protein of interest can be prepared for use as cell-free composition.

In one embodiment, compounds that specifically modulate KRC activity or the activity of a molecule in a signal transduction pathway involving KRC are identified based on their ability to modulate the interaction of KRC with a target molecule to which KRC binds. The target molecule can be a DNA molecule, e.g., an KRC-responsive element, such as the regulatory region of a chaperone gene) or a protein molecule. Suitable assays are known in the art that allow for the detection of protein—protein interactions (e.g., immunoprecipitations, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of KRC with a target molecule.

In one embodiment, the amount of binding of KRC or a molecule in a signal transduction pathway involving KRC to the target molecule in the presence of the test compound is greater than the amount of binding of KRC to the target molecule in the absence of the test compound, in which case the test compound is identified as a compound that enhances binding of KRC to a target. In another embodiment, the amount of binding of the KRC to the target molecule in the presence of the test compound is less than the amount of binding of the KRC (or e.g., Jun or TRAF) to the target molecule in the absence of the test compound, in which case the test compound is identified as a compound that inhibits binding of KRC to the target. Binding of the test compound to KRC or a molecule in a signal transduction pathway involving KRC can be determined either directly or indirectly as described above. Determining the ability of KRC protein to bind to a test compound can also be accomplished using a technology such as real-time Biomolecular Interaction Analysis (BIA) (Sjolander, S. and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between KRC (or e.g., Jun or TRAF) protein and a target molecule, the complete KRC protein can be used in the method, or, alternatively, only portions of the protein can be used. For example, an isolated KRC interacting domain (e.g., consisting of amino acids 204-1055 or a larger subregion including an interacting domain) can be used. An assay can be used to identify test compounds that either stimulate or inhibit the interaction between the KRC protein and a target molecule. A test compound that stimulates the interaction between the protein and a target molecule is identified based upon its ability to increase the degree of interaction between, e.g., KRC and a target molecule as compared to the degree of interaction in the absence of the test compound and such a compound would be expected to increase the activity of KRC in the cell. A test compound that inhibits the interaction between the protein and a target molecule is identified based upon its ability to decrease the degree of interaction between the protein and a target molecule as compared to the degree of interaction in the absence of the compound and such a compound would be expected to decrease KRC activity.

In one embodiment of the above assay methods of the present invention, it may be desirable to immobilize either KRC (or a molecule in a signal transduction pathway involving KRC, e.g., Jun or TRAF) or a respective target molecule for example, to facilitate separation of complexed from uncomplexed forms of one or both of the proteins, or to accommodate automation of the assay. Binding of a test compound to a KRC or a molecule in a signal transduction pathway involving KRC, or interaction of an KRC protein (or a molecule in a signal transduction pathway involving KRC) with a target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided in which a domain that allows one or both of the proteins to be bound to a matrix is added to one or more of the molecules. For example, glutathione-S-transferase fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or KRC protein, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of binding or activity determined using standard techniques.

Other techniques for immobilizing proteins on matrices can also be used in the screening assays of the invention. For example, either an KRC protein or a molecule in a signal transduction pathway involving KRC, or a target molecule can be immobilized utilizing conjugation of biotin and streptavidin. Biotinylated protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with protein or target molecules but which do not interfere with binding of the protein to its target molecule can be derivatized to the wells of the plate, and unbound target or KRC protein is trapped in the wells by antibody conjugation. Methods for detecting such complexes, in addition to those described above for the GST-immobilized complexes, include immunodetection of complexes using antibodies reactive with KRC or a molecule in a signal transduction pathway involving KRC or target molecule, as well as enzyme-linked assays which rely on detecting an enzymatic activity associated with the KRC protein or target molecule.

C. Assays Using Knock-Out Cells

In another embodiment, the invention provides methods for identifying compounds that modulate a biological effect of KRC or a molecule in a signal transduction pathway involving KRC using cells deficient in KRC (or e.g., Jun or TRAF). As described in the Examples, inhibition of KRC activity (e.g., by disruption of the KRC gene) in T cells results, e.g., in a deficiency of IL-2 production. Thus, cells deficient in KRC or a molecule in a signal transduction pathway involving KRC can be used identify agents that modulate a biological response regulated by KRC by means other than modulating KRC itself (i.e., compounds that "rescue" the KRC deficient phenotype). Alternatively, a "conditional knock-out" system, in which the gene is rendered non-functional in a conditional manner, can be used to create deficient cells for use in screening assays. For example, a tetracycline-regulated system for conditional disruption of a gene as described in WO 94/29442 and U.S. Pat. No. 5,650,298 can be used to create cells, or animals from which cells can be isolated, be rendered deficient in KRC (or a molecule in a signal transduction pathway involving KRC e.g., Jun or TRAF) in a controlled manner through modulation of the tetracycline concentration in contact with the cells. Specific cell types, e.g., lymphoid cells (e.g., thymic, splenic and/or lymph node cells) or purified cells such as T cells from such animals can be used in screening assays. In one embodiment, the entire 5.4 kB exon 2 of KRC can be replaced, e.g., with a neomycin cassette, resulting in an allele that produces no KRC protein. This embodiment is described in the appended examples.

In the screening method, cells deficient in KRC or a molecule in a signal transduction pathway involving KRC can be contacted with a test compound and a biological response regulated by KRC or a molecule in a signal transduction pathway involving KRC can be monitored. Modulation of the response in cells deficient in KRC or a molecule in a signal transduction pathway involving KRC (as compared to an appropriate control such as, for example, untreated cells or cells treated with a control agent) identifies a test compound as a modulator of the KRC regulated response.

In one embodiment, the test compound is administered directly to a non-human knock out animal, preferably a mouse (e.g., a mouse in which the KRC gene or a gene in a signal transduction pathway involving KRC is conditionally disrupted by means described above, or a chimeric mouse in which the lymphoid organs are deficient in KRC or a molecule in a signal transduction pathway involving KRC as described above), to identify a test compound that modulates the in vivo responses of cells deficient in KRC. In another embodiment, cells deficient in KRC are isolated from the non-human KRC or a molecule in a signal transduction pathway involving KRC deficient animal, and contacted with the test compound ex vivo to identify a test compound that modulates a response regulated by KRC in the cells Cells deficient in KRC or a molecule in a signal transduction pathway involving KRC can be obtained from a non-human animals created to be deficient in KRC or a molecule in a signal transduction pathway involving KRC Preferred non-human animals include monkeys, dogs, cats, mice, rats, cows, horses, goats and sheep. In preferred embodiments, the deficient animal is a mouse. Mice deficient in KRC or a molecule in a signal transduction pathway involving KRC can be made using methods known in the art. One example of such a method and the resulting KRC heterozygous and homozygous animals is described in the appended examples. Non-human animals deficient in a particular gene product typically are created by homologous recombination. In an exemplary embodiment, a vector is prepared which contains at least a portion of the gene into which a deletion, addition or substitution has been introduced to thereby alter, e.g., functionally disrupt, the endogenous KRC. The gene preferably is a mouse gene. For example, a mouse KRC gene can be isolated from a mouse genomic DNA library using the mouse KRC cDNA as a probe. The mouse KRC gene then can be used to construct a homologous recombination vector suitable for modulating an endogenous KRC gene in the mouse genome. In a preferred embodiment, the vector is designed such that, upon homologous recombination, the endogenous gene is functionally disrupted (i.e., no longer encodes a functional protein; also referred to as a "knock out" vector).

Alternatively, the vector can be designed such that, upon homologous recombination, the endogenous gene is mutated or otherwise altered but still encodes functional protein (e.g., the upstream regulatory region can be altered to thereby alter the expression of the endogenous KRC protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In one embodiment of the screening assay, compounds tested for their ability to modulate a biological response regulated by KRC or a molecule in a signal transduction pathway involving KRC are contacted with deficient cells by administering the test compound to a non-human deficient animal in vivo and evaluating the effect of the test compound on the response in the animal.

The test compound can be administered to a non-knock out animal as a pharmaceutical composition. Such compositions typically comprise the test compound and a pharmaceutically acceptable carrier. As used herein the term "pharmaceutically acceptable carrier" includes any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions. Pharmaceutical compositions are described in more detail below.

In another embodiment, compounds that modulate a biological response regulated by KRC or a signal transduction pathway involving KRC are identified by contacting cells deficient in KRC ex vivo with one or more test compounds, and determining the effect of the test compound on a read-out. In one embodiment, KRC deficient cells contacted with a test compound ex vivo can be readministered to a subject.

For practicing the screening method ex vivo, cells deficient, e.g., in KRC, Jun or TRAF can be isolated from a non-human deficient animal or embryo by standard methods and incubated (i.e., cultured) in vitro with a test compound. Cells (e.g., T cells) can be isolated from e.g., KRC, Jun or TRAF deficient animals by standard techniques.

In another embodiment, cells deficient in more than one member of a signal transduction pathway involving KRC can be used in the subject assays.

Following contact of the deficient cells with a test compound (either ex vivo or in vivo), the effect of the test compound on the biological response regulated by KRC or a molecule in a signal transduction pathway involving KRC can be determined by any one of a variety of suitable methods, such as those set forth herein, e.g., including light microscopic analysis of the cells, histochemical analysis of the cells, production of proteins, induction of certain genes, e.g., cytokine gene, such as IL-2.

D. Test Compounds

A variety of test compounds can be evaluated using the screening assays described herein. The term "test compound" includes any reagent or test agent which is employed in the assays of the invention and assayed for its ability to influence the expression and/or activity of KRC or a molecule in a signal transduction pathway involving KRC. More than one compound, e.g., a plurality of compounds, can be tested at the same time for their ability to modulate the expression and/or activity of, e.g., KRC in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). J. Am. Chem. Soc. 114:10987; DeWitt et al. (1993). Proc. Natl. Acad. Sci. USA 90:6909) peptoids (Zuckermann. (1994). J. Med. Chem. 37:2678) oligocarbamates (Cho et al. (1993). Science. 261:1303-), and hydantoins (DeWitt et al. supra). An approach for the synthesis of molecular libraries of small organic molecules with a diversity of 104-105 as been described (Carell et al. (1994). Angew. Chem. Int. Ed. Engl. 33:2059-; Carell et al. (1994) Angew. Chem. Int. Ed. Engl. 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Other exemplary methods for the synthesis of molecular libraries can be found in the art, for example in: Erb et al. (1994). Proc. Natl. Acad. Sci. USA 91:11422-; Horwell et al. (1996) Immunopharmacology 33:68-; and in Gallop et al. (1994); J. Med. Chem. 37:1233-.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl. Acad. Sci. USA 89:1865-1869) or on phage (Scott and Smith (1990) Science 249:386-390); (Devlin (1990) Science 249:404-406); (Cwirla et al. (1990) Proc.

*Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of KRC (e.g., dominant negative mutant forms of the molecule).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by KRC. It will be understood that it may be desirable to formulate such compound(s) as pharmaceutical compositions (described supra) prior to contacting them with cells.

Once a test compound is identified that directly or indirectly modulates, e.g., KRC expression or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

The instant invention also pertains to compounds identified in the subject screening assays.

III. Pharmaceutical Compositions

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, the test compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

IV. Methods for Modulating Biological Responses Regulated by KRC

The present invention provides for both prophylactic and therapeutic methods of treating a subject at risk of (or susceptible to) a disorder or having a disorder associated with an aberrant cell proliferation or survival. For example, an immune system disorder or condition associated with an undesirable immune response (such as an unwanted or excessive inflammatory response, an autoimmune disorder, graft-versus-host disease (GVHD), an allogeneic transplant) or an immune system disorder or condition that would benefit from an enhanced immune response, e.g. an immunosuppressed individual.

In one aspect, the invention provides a method for preventing in a subject, a disease or condition associated with an aberrant or unwanted immune response or, alternatively, an abnormally low immune response, by administering to the subject an agent which downmodulates the activity of KRC. Subjects at risk for such disorders can be identified by, for example, any or a combination of diagnostic or prognostic assays known in the art. Administration of a prophylactic agent can occur prior to the manifestation of symptoms characteristic of the aberrant immune response, such that a disease or disorder is prevented or, alternatively, delayed in its progression. Depending on the type of immune response aberrancy, for example, a KRC antagonist or agonist agent can be used for treating a subject. The appropriate agent can be determined based on screening assays described herein. In a preferred embodiment, the agent may be a peptide comprising the amino acid residues 204-1055 of KRC, a peptide that binds to KRC, a KRC ZAS domain or a small molecule.

Another aspect of the invention pertains to methods of modulating KRC activity for therapeutic purposes. KRC activity can be modulated in order to modulate the immune response. Because KRC upregulates immune responses, enhanced KRC activity and/or expression results in upregulation of immune responses, whereas inhibition of KRC activity results in downregulation of immune responses.

Modulatory methods of the invention involve contacting a cell (e.g., a T cell) with an agent that modulates the activity of KRC. An agent that modulates KRC activity can be an agent as described herein, such as a KRC peptide (e.g., the agent may be a peptide comprising the amino acid residues 204-1055 of KRC, a peptide that binds to KRC, a KRC ZAS domain or a small molecule), a nucleic acid molecule encoding one of the aforementioned peptides, a KRC agonist or antagonist, a peptidomimetic of a KRC agonist or antagonist, a KRC peptidomimetic, or other small molecule identified using the screening methods described herein.

These modulatory methods can be performed in vitro (e.g., by contacting the cell with the agent) or, alternatively, in vivo (e.g., by administering the agent to a subject). As such, the present invention provides methods of treating an individual afflicted with a condition or disorder that would benefit from up- or down-modulation of a KRC polypeptide, e.g., a disorder characterized by an unwanted, insufficient, or aberrant immune response. In one embodiment, the method involves administering an agent (e.g., an agent identified by a screening assay described herein), or combination of agents that modulates (e.g., upregulates or downregulates) KRC activity.

Inhibition of KRC activity is desirable in situations in which KRC is abnormally upregulated and/or in which decreased KRC activity is likely to have a beneficial effect, for example in a situation of an excessive or unwanted immune response. Such situations include conditions, disorders, or diseases such as an autoimmune disorder, a transplant (e.g., a bone marrow transplant, a stem cell transplant, a heart transplant, a lung transplant, a liver transplant, a kidney transplant, a cornea transplant, or a skin transplant), graft versus host disease (GVHD), an allergy, or in inflammatory disorder. Likewise, upregulation of KRC activity is desirable in situations in which KRC is abnormally downregulated and/or in which increased KRC activity is likely to have a beneficial effect (e.g., in a neoplasia).

As used herein, the term "autoimmunity" refers to the condition in which a subject's immune system starts reacting against his or her own tissues. Non-limiting examples of autoimmune diseases and disorders having an autoimmune component that would benefit from modulation of a KRC activity include type 1 diabetes, arthritis (including rheumatoid arthritis, juvenile rheumatoid arthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, iritis, conjunctivitis, keratoconjunctivitis, ulcerative colitis, asthma, allergic asthma, cutaneous lupus erythematosus, scleroderma, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The terms "neoplasia," "hyperplasia," and "tumor" are often commonly referred to as "cancer," which is a general name for more than 100 disease that are characterized by uncontrolled, abnormal growth of cells. Examples of malignancies include but are not limited to acute lymphoblastic leukemia; acute myeloid leukemia; adrenocortical carcinoma; AIDS-related lymphoma; cancer of the bile duct; bladder cancer; bone cancer, osteosarcomal malignant fibrous histiocytomal brain stem gliomal brain tumor; breast cancer; bronchial adenomas; carcinoid tumors; adrenocortical carcinoma; central nervous system lymphoma; cancer of the sinus, cancer of the gall bladder; gastric cancer; cancer of the salivary glands; cancer of the esophagus; neural cell cancer; intestinal cancer (e.g., of the large or small intestine); cervical cancer; colon cancer; colorectal cancer; cutaneous T-cell lymphoma; B-cell lymphoma; T-cell lymphoma; endometrial cancer; epithelial cancer; endometrial cancer; intraocular melanoma; retinoblastoma; hairy cell leukemia; liver cancer; Hodgkin's disease; Kaposi's sarcoma; acute lymphoblastic leukemia; lung cancer; non-Hodgkin's lymphoma; melanoma; multiple myeloma; neuroblastoma; prostate cancer; retinoblastoma; Ewing's sarcoma; vaginal cancer; Waldenstrom's macroglobulinemia; adenocarcinomas; ovarian cancer, chronic lymphocytic leukemia, pancreatic cancer; and Wilm's tumor.

Exemplary agents for use in upmodulating KRC (i.e., KRC agonists) include, e.g., nucleic acid molecules encoding KRC polypeptides, KRC peptides, and compounds that stimulate the interaction of KRC with TRAF or c-Jun, for example (e.g., compounds identified in the subject screening assays).

Exemplary agents for use in downmodulating KRC (i.e., KRC antagonists) include agents that inhibit the activity of KRC in an immune cell (e.g., compounds identified in the subject screening assays).

A. Downregulation of Immune Responses

There are numerous embodiments of the invention for downregulating the function of a KRC polypeptide to thereby downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both.

For example, KRC activity can be inhibited by contacting a cell which expresses KRC with an agent that inhibits KRC. Such an agent can be a compound identified by the screening assays described herein. In another embodiment, the agent is a peptide. In a preferred embodiment, the agent can interact with the amino acid residues 204-1055 of KRC to inhibit KRC activity.

An immune response can be further inhibited by the use of an additional agent that can thereby downmodulate the immune response, as described further herein.

Agents that inhibit a KRC activity can be identified by their ability to inhibit immune cell proliferation and/or effector function, or to induce anergy when added to an in vitro assay. A number of art-recognized readouts of cell activation can be employed to measure, e.g., cell proliferation or effector function (e.g., cytokine production or phagocytosis) in the presence of the activating agent. The ability of a test agent to block this activation can be readily determined by measuring the ability of the agent to effect a decrease in proliferation or effector function being measured.

In another embodiment, immune responses can be downregulated in a subject by removing immune cells from the patient, contacting the immune cells in vitro with an agent (e.g., a small molecule) that downregulates KRC activity, and reintroducing the in vitro-stimulated immune cells into the patient.

Downregulating immune responses by inhibiting KRC activity is useful in downmodulating the immune response, e.g., in situations of tissue, skin and organ transplantation, in graft-versus-host disease (GVHD), or allergies, or in autoimmune diseases such as systemic lupus erythematosus and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which inhibits the activity of KRC, e.g., by blocking the interaction of KRC with, for example, TRAF or c-Jun, in immune cells (such as a KRC, TRAF, or c-Jun peptide or a small molecule) alone or in conjunction with another downmodulatory agent can inhibit the generation of an immune response. Moreover, inhibition of KRC activity by inhibition of, for example, KRC-TRAF interaction may also be sufficient to anergize the immune cells, thereby inducing tolerance in a subject.

Other downmodulatory agents that can be used in connection with the downmodulatory methods of the invention include, for example, blocking antibodies against other immune cell markers, or soluble forms of other receptor ligand pairs (e.g., agents that disrupt the interaction between CD40 and CD40 ligand (e.g., anti CD40 ligand antibodies)), antibodies against cytokines, or immunosuppressive drugs (e.g., FK506, cyclosporin, rapamycin, steroids).

For example, inhibition of KRC activity may also be useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents that inhibit an activity of KRC may lead to long-term relief from the disease. Additionally, co-administration of agents which block costimulation of immune cells by disrupting receptor-ligand interactions may be useful in inhibiting immune cell activation to prevent production of autoantibodies or cytokines which may be involved in the disease process. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840-856).

Inhibition of immune cell activation is useful therapeutically in the treatment of allergies and allergic reactions, e.g., by inhibiting IgE production. An agent that inhibits KRC activity can be administered to an allergic subject to inhibit immune cell-mediated allergic responses in the subject. Inhibition of KRC activity can be accompanied by exposure to allergen in conjunction with appropriate MHC molecules.

Allergic reactions can be systemic or local in nature, depending on the route of entry of the allergen and the pattern of deposition of IgE on mast cells or basophils. Thus, immune cell-mediated allergic responses can be inhibited locally or systemically by administration of an agent that inhibits KRC activity.

Downregulation of immune cell activation through inhibition of KRC activity may also be important therapeutically in pathogenic infections of immune cells (e.g., by viruses or bacteria). For example, in the acquired immune deficiency syndrome (AIDS), viral replication is stimulated by immune cell activation. Inhibition of KRC activity may result in inhibition of viral replication and thereby ameliorate the course of AIDS.

Downregulation of immune cell activation via inhibition of KRC activity interaction may also be useful in treating inflammatory disorders and in promoting the maintenance of pregnancy when there exists a risk of immune-mediated spontaneous abortion.

Exemplary Inhibitory Compounds

Since inhibition of KRC activity is associated with an decreased immune response, to downmodulate or inhibit the immune response, cells (e.g., T cells) are contacted with an agent that inhibits KRC activity. The immune cells may be contacted with the agent in vitro and then the cells can be administered to a subject or, alternatively, the agent may be administered to the subject (e.g., directly to an articular site at which T growth and/or differentiation is desired). The methods of the invention using KRC inhibitory compounds can be used in the treatment of disorders in which the immune response is diminished, blocked, inhibited, downregulated or the like.

Inhibitory compounds of the invention can be, for example, intracellular binding molecules that act to specifically inhibit the expression or activity of KRC. As used herein, the term "intracellular binding molecule" is intended to include molecules that act intracellularly to inhibit the expression or activity of a protein by binding to the protein or to a nucleic acid (e.g., an mRNA molecule) that encodes the protein. Examples of intracellular binding molecules, described in further detail below, include antisense nucleic acids, intracellular antibodies, peptidic compounds that inhibit the interaction of KRC with a target molecule (e.g., calcineurin) and chemical agents that specifically inhibit KRC activity.

i. Antisense Nucleic Acid Molecules

In one embodiment, an inhibitory compound of the invention is an antisense nucleic acid molecule that is complementary to a gene encoding KRC, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences encoding KRC disclosed herein, antisense nucleic acids of the invention can be designed according to the rules of Watson and Crick base pairing. The antisense nucleic acid molecule can be complementary to the entire coding region of KRC mRNA, but more preferably is an oligonucleotide which is antisense to only a portion of the coding or noncoding region of KRC mRNA. For example, the antisense oligonucleotide can be complementary to the region surrounding the translation start site of KRC mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a KRC protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment, an antisense nucleic acid of the invention is a compound that mediates RNAi. RNA interfering agents include, but are not limited to, nucleic acid molecules including RNA molecules which are homologous to the target gene or genomic sequence, e.g., KRC, TRAF, c-Jun and/or c-Fos, or a fragment thereof, "short interfering RNA" (siRNA), "short hairpin" or "small hairpin RNA" (shRNA), and small molecules which interfere with or inhibit expression of a target gene by RNA inerference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591) can be used to catalytically cleave KRC mRNA transcripts to thereby inhibit translation of KRC mRNA. A ribozyme having specificity for a KRC-encoding nucleic acid can be designed based upon the nucleotide sequence of SEQ ID NO:1 a nucleic acid molecule encoding another KRC family polypeptide. For example, a derivative of a *Tetrahymena* L-19 IVS RNA can be constructed in which the nucleotide sequence of the active site is complementary to the nucleotide sequence to be cleaved in a KRC-encoding mRNA. See, e.g., Cech et al. U.S. Pat. No. 4,987,071; and Cech et al. U.S. Pat. No. 5,116,742. Alternatively, KRC mRNA can be used to select a catalytic RNA having a specific ribonuclease activity from a pool of RNA molecules. See, e.g., Bartel, D. and Szostak, J. W., 1993, *Science* 261:1411-1418.

Alternatively, gene expression can be inhibited by targeting nucleotide sequences complementary to the regulatory region of KRC (e.g., the KRC promoter and/or enhancers) to form triple helical structures that prevent transcription of the KRC gene in target cells. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In yet another embodiment, the KRC nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., 1996, *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al., 1996, supra; Perry-O'Keefe et al., 1996, *Proc. Natl. Acad. Sci. USA* 93: 14670-675.

PNAs of KRC nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of KRC nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., 1996, supra)); or as probes or primers for DNA sequencing or hybridization (Hyrup B. et al., 1996, supra; Perry-O'Keefe supra).

In another embodiment, PNAs of KRC can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of KRC nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B., 1996, supra). The synthesis of PNA-DNA chimeras can be performed as described in Hyrup B., 1996, supra and Finn P. J. et al., 1996, *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al., 1989, *Nucleic Acid Res.* 17: 5973-88). PNA monomers are then coupled in a stepwise manner to produce a chimeric molecule with a 5' PNA segment and a 3' DNA segment (Finn P. J. et al., 1996, supra). Alternatively, chimeric molecules can be synthesized with a 5' DNA segment and a 3' PNA segment (Peterser, K. H. et al., 1975, *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. US.* 86:6553-6556; Lemaitre et al., 1987, *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (See, e.g., Krol et al., 1988, *Bio-Techniques* 6:958-976) or intercalating agents. (See, e.g., Zon, 1988, *Pharm. Res.* 5:539-549). To this end, the oligonucleotide may be conjugated to another molecule, (e.g., a peptide, hybridization triggered cross-linking agent, transport agent, or hybridization-triggered cleavage agent).

Antisense polynucleotides may be produced from a heterologous expression cassette in a transfectant cell or transgenic cell. Alternatively, the antisense polynucleotides may comprise soluble oligonucleotides that are administered to the external milieu, either in the culture medium in vitro or in the circulatory system or in interstitial fluid in vivo. Soluble antisense polynucleotides present in the external milieu have been shown to gain access to the cytoplasm and inhibit translation of specific mRNA species.

ii. Intracellular Antibodies

Another type of inhibitory compound that can be used to inhibit the expression and/or activity of KRC protein in a cell is an intracellular antibody specific for KRC discussed herein. The use of intracellular antibodies to inhibit protein function in a cell is known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Letters* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Bio/Technology* 12:396-399; Chen, S-Y. et al. (1994) *Human Gene Therapy* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) J. Biol. Chem. 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of transcription factor activity according to the inhibitory methods of the invention, preferably an intracellular antibody that specifically binds the transcription factor is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g., Biocca, S. et al. (1990) *EMBO J.* 9:101-108; Mhashilkar, A. M. et al. (1995) *EMBO J.* 14:1542-1551). A preferred nuclear localization signal to be used for nuclear targeting of the intracellular antibody chains is the nuclear localization signal of SV40 Large T antigen (see Biocca, S. et al. (1990) *EMBO J.* 9:101-108; Mhashilkar, A. M. et al. (1995) *EMBO J.* 14:1542-1551).

To prepare an intracellular antibody expression vector, antibody light and heavy chain cDNAs encoding antibody chains specific for the target protein of interest, e.g., KRC protein, is isolated, typically from a hybridoma that secretes a monoclonal antibody specific for KRC protein. Preparation of antisera against KRC protein has been described in the art (see e.g., Rao et al, U.S. Pat. No. 5,656,452). Anti-KRC protein antibodies can be prepared by immunizing a suitable subject, (e.g., rabbit, goat, mouse or other mammal) with a KRC protein immunogen. An appropriate immunogenic preparation can contain, for example, recombinantly expressed KRC protein or a chemically synthesized KRC peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a KRC protein immunogen as described above, and the culture supernatants of the resulting hybridoma cells are screened to identify a hybridoma producing a monoclonal antibody that binds specifically to the KRC protein. Any of the many well known protocols used for fusing lymphocytes and immortalized cell lines can be applied for the purpose of generating an anti-KRC protein monoclonal antibody (see, e.g., G. Galfre et al. (1977) *Nature* 266:550-52; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled artisan will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the maf protein are identified by screening the hybridoma culture supernatants for such antibodies, e.g., using a standard ELISA assay.

Alternative to preparing monoclonal antibody-secreting hybridomas, a monoclonal antibody that binds to a KRC can be identified and isolated by screening a recombinant combinatorial immunoglobulin library (e.g., an antibody phage display library) with the protein, or a peptide thereof, to thereby isolate immunoglobulin library members that bind specifically to the protein. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and compounds particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226: 889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature (*1990) 348:552-554.

Once a monoclonal antibody of interest specific for KRC has been identified (e.g., either a hybridoma-derived monoclonal antibody or a recombinant antibody from a combinatorial library, including monoclonal antibodies to KRC that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E.A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g., from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit transcription factor activity in a cell, the expression vector encoding the KRC-specific intracellular antibody is introduced into the cell by standard transfection methods as described hereinbefore.

iii. KRC-Derived Peptidic Compounds

In another embodiment, an inhibitory compound of the invention is a peptidic compound derived from the KRC amino acid sequence. In particular, the inhibitory compound comprises a portion of KRC (or a mimetic thereof) that mediates interaction of KRC with a target molecule such that contact of KRC with this peptidic compound competitively inhibits the interaction of KRC with the target molecule. In an exemplary embodiment, the peptide compound is designed based on the region of KRC that mediates interaction of KRC with, for example, TRAF. As described herein, amino acid residues 204-1055 of the KRC protein mediate the interaction of the KRC proteins with TRAF and peptides spanning the region inhibit the ability of TRAF to bind to and phosphorylate KRC proteins, without affecting the phosphatase activity of TRAF against other substrates. Moreover, when expressed intracellularly, peptides spanning this region inhibit KRC dephosphorylation, nuclear translocation and KRC-mediated gene expression in response to stimulation, thereby inhibiting KRC-dependent functions.

In a preferred embodiment, a KRC inhibitory compound is a peptidic compound, which is prepared based on a TRAF-interacting region of KRC. A peptide can be derived from the TRAF-interacting region of KRC having an amino acid sequence that comprises the amino acid residues 204-1055 of KRC. In another preferred embodiment, a KRC inhibitory compound is a peptidic compound, which is prepared based on a c-Jun-interacting region of KRC. A peptide can be derived from the c-Jun-interacting region of KRC having an amino acid sequence that comprises the amino acid residues 204-1055 of KRC. Alternatively, longer or shorter regions of human KRC can be used such as a peptide.

The peptidic compounds of the invention can be made intracellularly in immune cells by introducing into the immune cells an expression vector encoding the peptide. Such expression vectors can be made by standard techniques, using, for example, oligonucleotides that encode the amino acid sequences of SEQ ID NO:2. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques. Synthesized peptides can then be introduced into cells by a variety of means known in the art for introducing peptides into cells (e.g., liposome and the like).

Other inhibitory agents that can be used to specifically inhibit the activity of an KRC protein are chemical compounds that directly inhibit KRC activity or inhibit the interaction between KRC and target molecules. Such compounds can be identified using screening assays that select for such compounds, as described in detail above.

B. Upregulation of Immune Responses

Stimulation of KRC activity as a means of upregulating immune responses is also useful in therapy. Upregulation of immune responses can be in the form of enhancing an existing immune response or eliciting an initial immune response. For example, enhancing an immune response through enhancing of KRC activity is useful in cases of infections with microbes, e.g., bacteria, viruses, or parasites. For example, in one embodiment, an agent that enhances KRC activity, e.g., a small molecule or a KRC peptide, is therapeutically useful in situations where upregulation of antibody and cell-mediated responses, resulting in more rapid or thorough clearance of a virus, would be beneficial. These conditions include viral skin diseases such as Herpes or shingles, in which case such an agent can be delivered topically to the skin. In addition, systemic viral diseases such as influenza, the common cold, and encephalitis might be alleviated by the administration of such agents systemically. In certain instances, it may be desirable to further administer other agents that upregulate immune responses, for example, agents that transduce signals via costimulatory receptors, in order further augment the immune response.

Alternatively, immune responses can be enhanced in an infected patient by removing immune cells from the patient, contacting immune cells in vitro with an agent (e.g., a small molecule) that enhances KRC activity, and reintroducing the in vitro-stimulated immune cells into the patient. In another embodiment, a method of enhancing immune responses involves isolating infected cells from a patient, e.g., virally infected cells, transfecting them with a nucleic acid molecule encoding a form of KRC that is more active than the wild type KRC, such that the cells express all or a portion of the KRC molecule on their surface, and reintroducing the transfected cells into the patient. The transfected cells may be capable of preventing an inhibitory signal to, and thereby activating, immune cells in vivo.

An agent that enhances KRC activity can be used prophylactically in therapy against various polypeptides, e.g., polypeptides derived from pathogens for vaccination. Immunity against a pathogen, e.g., a virus, can be induced by vaccinating with a viral polypeptide along with an agent that enhances KRC activity. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) *Proc. Natl. Acad. Sci. USA* 94:961). Attenuated microorganisms can be used for delivery to mucosal surfaces (Sizemore et al. (1995) *Science* 270:29).

Stimulation of an immune response to tumor cells can also be achieved by enhancing KRC activity by treating a patient with an agent that for example, enhancing KRC-TRAF interaction. Preferred examples of such agents include, e.g., and compounds identified in the subject screening assays and peptides.

In another embodiment, the immune response can be stimulated by enhancing of KRC activity such that preexisting tolerance is overcome. For example, immune responses against antigens to which a subject cannot mount a significant immune response, e.g., tumor-specific antigens, can be induced by administering an agent that stimulates the activity of KRC activity. Other KRC agonists can be used as adjuvants to boost responses to foreign antigens in the process of active immunization.

In one embodiment, immune cells are obtained from a subject and cultured ex vivo in the presence of an agent that that enhances KRC activity to expand the population of immune cells. In a further embodiment the immune cells are then administered to a subject. immune cells can be stimulated to proliferate in vitro by, for example, providing the immune cells with a primary activation signal and a costimulatory signal, as is known in the art. Various forms of KRC polypeptides or agents that enhance KRC activity can also be used to costimulate proliferation of immune cells. In one embodiment immune cells are cultured ex vivo according to the method described in PCT Application No. WO 94/29436. The agent can be soluble, attached to a cell membrane or attached to a solid surface, such as a bead.

In an additional embodiment, in performing any of the methods described herein, it is within the scope of the invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that enhances KRC activity.

In another embodiment, a method of upregulating immune responses involves transfecting them with a nucleic acid molecule encoding a KRC molecule with a mutation or a peptide that enhances, for example, KRC-TRAF interaction (e.g., a TRAF-C domain), such that the cells express the KRC molecule (e.g., in the cell membrane) or the peptide (e.g., in the cytoplasm), and reintroducing the transfected cells into the patient. The ability of the transfected cells to be activated can thus be increased.

Examples of other immunomodulating reagents include antibodies that provide a costimulatory signal, (e.g., agonists of CD28 or ICOS), stimulating antibodies against immune cell markers, and/or cytokines and the like.

Exemplary Stimulatory Compounds

Since upregulation of KRC activity is associated with an increased immune response, a compound that specifically stimulates KRC activity and/or expression can be used to enhance or upmodulate an immune response. In the stimulatory methods of the invention, a subject is treated with a stimulatory compound that stimulates expression. and/or activity of a KRC molecule. The methods of the invention using KRC stimulatory compounds can be used in the treatment of disorders in which the immune response is enhanced, promoted, stimulated, upregulated or the like.

Examples of stimulatory compounds include active KRC protein, expression vectors encoding KRC and chemical agents that specifically stimulate KRC activity.

A preferred stimulatory compound is a nucleic acid molecule encoding KRC, wherein the nucleic acid molecule is introduced into the subject (e.g., T cells of the subject) in a form suitable for expression of the KRC protein in the cells of the subject. For example, a KRC cDNA (full length or partial KRC cDNA sequence) is cloned into a recombinant expression vector and the vector is transfected into the immune cell using standard molecular biology techniques. The KRC cDNA can be obtained, for example, by amplification using the polymerase chain reaction (PCR) or by screening an appropriate cDNA library. The nucleotide sequences of KRC cDNA is known in the art and can be used for the design of PCR primers that allow for amplification of a cDNA by standard PCR methods or for the design of a hybridization probe that can be used to screen a cDNA library using standard hybridization methods.

Following isolation or amplification of KRC cDNA, the DNA fragment is introduced into a suitable expression vector, as described above. Nucleic acid molecules encoding KRC in the form suitable for expression of the KRC in a host cell, can be prepared as described above using nucleotide sequences known in the art. The nucleotide sequences can be used for the design of PCR primers that allow for amplification of a cDNA by standard PCR methods or for the design of a hybridization probe that can be used to screen a cDNA library using standard hybridization methods.

Another form of a stimulatory compound for stimulating expression of KRC in a cell is a chemical compound that specifically stimulates the expression or activity of endogenous KRC in the cell. Such compounds can be identified using screening assays that select for compounds that stimulate the expression or activity of KRC as described herein.

The method of the invention for modulating KRC activity in a subject can be practiced either in vitro or in vivo (the latter is discussed further in the following subsection). For practicing the method in vitro, cells (e.g., r cells) can be obtained from a subject by standard methods and incubated (i.e., cultured) in vitro with a stimulatory or inhibitory compound of the invention to stimulate or inhibit, respectively, the activity of KRC. Methods for isolating immune cells are known in the art.

Cells treated in vitro with either a stimulatory or inhibitory compound can be administered to a subject to influence the growth and/or differentiation of immune cells in the subject. For example, immune cells can be isolated from a subject, expanded in number in vitro by enhancing KRC activity in the cells using an enhancing agent (thereby promoting the proliferation of the cells), and then the immune cells can be readministered to the same subject, or another subject tissue compatible with the donor of the immune cells. Accordingly, in another embodiment, the modulatory method of the invention comprises culturing immune cells in vitro with a KRC modulator and further comprises administering the immune cells to a subject to thereby modulate T growth and/or differentiation in a subject. Upon culture in vitro, the immune cells can differentiate into mature immune cells and thus the methods encompass administering this mature immune cells to the subject. For administration of cells or T to a subject, it may be preferable to first remove residual compounds in the culture from the cells or T before administering them to the subject. This can be done for example by gradient centrifugation of the cells or by washing of the T tissue. For further discussion of ex vivo genetic modification of cells followed by readministration to a subject, see also U.S. Pat. No. 5,399,346 by W. F. Anderson et al.

In other embodiments, a stimulatory or inhibitory compound is administered to a subject in vivo, such as directly to an articulation site of a subject. For stimulatory or inhibitory agents that comprise nucleic acids (e.g., recombinant expression vectors encoding KRC, antisense RNA, intracellular antibodies or KRC-derived peptides), the compounds can be introduced into cells of a subject using methods known in the art for introducing nucleic acid (e.g., DNA) into cells in vivo. Examples of such methods include:

Direct Injection: Naked DNA can be introduced into cells in vivo by directly injecting the DNA into the cells (see e.g., Acsadi et al. (1991) *Nature* 332:815-818; Wolff et al. (1990) *Science* 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122-2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschinetal. (1984) *J. Virol.* 51:611-619; and Flotte et al. (1993) *J. Biol. Chem.* 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay.

V. Diagnostic Assays

In another aspect, the invention features a method of diagnosing a subject for a disorder associated with aberrant biological activity or KRC (e.g., that would benefit from modulation of, e.g., modulation of TNFα production, modulation of IL-2 production, modulation of JNK signaling pathway, modulation of an NFkB signaling pathway, modulation of AP-1 activity, modulation of Ras and Rac activity, modulation of actin polymerization, modulation of ubiquitination of AP-1, modulation of the degradation of c-Jun, modulation of the degradation of c-Fos, modulation of effector T cell function, modulation of T cell anergy, modulation of apoptosis, and modulation of T cell differentiation.

In one embodiment, the invention comprises identifying the subject as one that would benefit from modulation of an KRC activity, e.g., modulation of the IL-2 production or apoptosis. For example, in one embodiment, expression of KRC or a molecule in a signal transduction pathway involving KRC can be detected in cells of a subject suspected of having a disorder associated with aberrant biological activity of KRC. The expression of KRC or a molecule in a signal transduction pathway involving KRC in cells of said subject could then be compared to a control and a difference in expression of KRC or a molecule in a signal transduction pathway involving KRC in cells of the subject as compared to the control could be used to diagnose the subject as one that would benefit from modulation of an KRC activity.

The "change in expression" or "difference in expression" of KRC or a molecule in a signal transduction pathway involving KRC in cells of the subject can be, for example, a change in the level of expression of KRC or a molecule in a signal transduction pathway involving KRC in cells of the subject as compared to a previous sample taken from the subject or as compared to a control, which can be detected by assaying levels of, e.g., KRC mRNA, for example, by isolating cells from the subject and determining the level of KRC mRNA expression in the cells by standard methods known in the art, including Northern blot analysis, microarray analysis, reverse-transcriptase PCR analysis and in situ hybridizations. For example, a biological specimen can be obtained from the patient and assayed for, e.g., expression or activity of KRC or a molecule in a signal transduction pathway involving KRC. For instance, a PCR assay could be used to measure the level of KRC in a cell of the subject. A level of KRC higher or lower than that seen in a control or higher or lower than that previously observed in the patient indicates that the patient would benefit from modulation of a signal transduction pathway involving KRC. Alternatively, the level of expression of KRC or a molecule in a signal transduction pathway involving KRC in cells of the subject can be detected by assaying levels of, e.g., KRC, for example, by isolating cells from the subject and determining the level of KRC or a molecule in a signal transduction pathway involving KRC protein expression by standard methods known in the art, including Western blot analysis, immunoprecipitations, enzyme linked immunosorbent assays (ELISAs) and immunofluorescence. Antibodies for use in such assays can be made using techniques known in the art and/or as described herein for making intracellular antibodies.

In another embodiment, a change in expression of KRC or a molecule in a signal transduction pathway involving KRC in cells of the subject results from one or more mutations (i.e., alterations from wildtype), e.g., the KRC gene and mRNA leading to one or more mutations (i.e., alterations from wildtype) in the amino acid sequence of the protein. In one embodiment, the mutation(s) leads to a form of the molecule with increased activity (e.g., partial or complete constitutive activity). In another embodiment, the mutation(s) leads to a form of the molecule with decreased activity (e.g., partial or complete inactivity). The mutation(s) may change the level of expression of the molecule for example, increasing or decreasing the level of expression of the molecule in a subject with a disorder. Alternatively, the mutation(s) may change the regulation of the protein, for example, by modulating the interaction of the mutant protein with one or more targets e.g., resulting in a form of KRC that cannot be phosphorylated or cannot interact with a KRC binding partner. Mutations in the nucleotide sequence or amino acid sequences of proteins can be determined using standard techniques for analysis of DNA or protein sequences, for example for DNA or protein sequencing, RFLP analysis, and analysis of single nucleotide or amino acid polymorphisms. For example, in one embodiment, mutations can be detected using highly sensitive PCR approaches using specific primers flanking the nucleic acid sequence of interest. In one embodiment, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *PNAS* 91:360-364). This method can include the steps of collecting a sample of cells from a patient, isolating nucleic acid (e.g., genomic, DNA) from the cells of the sample, contacting the nucleic acid sample with one or more primers which specifically amplify a sequence under conditions such that hybridization and amplification of the sequence (if present) occurs, and detecting the presence or absence of an amplification product, or detecting the size of the amplification product and comparing the length to a control sample.

In one embodiment, the complete nucleotide sequence for KRC or a molecule in a signal transduction pathway involving KRC can be determined. Particular techniques have been developed for determining actual sequences in order to study polymorphism in human genes. See, for example, Proc. Natl. Acad. Sci. U.S.A. 85, 544-548 (1988) and Nature 330, 384-386 (1987); Maxim and Gilbert. 1977. *PNAS* 74:560; Sanger 1977. *PNAS* 74:5463. In addition, any of a variety of automated sequencing procedures can be utilized when performing diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Restriction fragment length polymorphism mappings (RFLPS) are based on changes at a restriction enzyme site. In one embodiment, polymorphisms from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Moreover, the use of sequence specific ribozymes (see, for example, U.S. Pat. No. 5,498,531) can be used to score for the presence of a specific ribozyme cleavage site.

Another technique for detecting specific polymorphisms in particular DNA segment involves hybridizing DNA segments which are being analyzed (target DNA) with a complimentary, labeled oligonucleotide probe. See Nucl. Acids Res. 9, 879-894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Other methods for detecting polymorphisms in nucleic acid sequences include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the polymorphic sequence with potentially polymorphic RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels. See, for example, Cotton et al. (1988) *Proc. Natl. Acad. Sci USA* 85:4397; Saleeba et al. (1992) *Methods Enzymol.* 217:286-295. In a preferred embodiment, the control DNA or RNA can be labeled for detection.

In another embodiment, alterations in electrophoretic mobility can be used to identify polymorphisms. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125-144; and Hayashi (1992) *Genet Anal Tech Appl* 9:73-79). Single-stranded DNA fragments of sample and control nucleic acids can be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of nucleic acid molecule comprising polymorphic sequences in polyacrylamide gels containing a gradient of denaturant is assayed using denaturing gradient gel electrophoresis (DGGE) (Myers et al. (1985) *Nature* 313:495). When DGGE is used as the method of analysis, DNA can be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting polymorphisms include, but are not limited to, selective oligonucleotide hybridization, selective amplification, or selective primer extension. For example, oligonucleotide primers may be prepared in which the polymorphic region is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different polymorphisms when the oligonucleotides are attached to the hybridizing membrane and hybridized with labeled target DNA.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Many other techniques for identifying and detecting polymorphisms are known to those skilled in the art, including those described in "DNA Markers: Protocols, Applications and Overview," G. Caetano-Anolles and P. Gresshoff ed., (Wiley-VCH, New York) 1997, which is incorporated herein by reference as if fully set forth.

In addition, many approaches have also been used to specifically detect SNPs. Such techniques are known in the art and many are described e.g., in DNA Markers: Protocols, Applications, and Overviews. 1997. Caetano-Anolles and Giesshoff, Eds. Wiley-VCH, New York, pp 199-211 and the references contained therein). For example, in one embodiment, a solid phase approach to detecting polymorphisms such as SNPs can be used. For example an oligonucleotide ligation assay (OLA) can be used. This assay is based on the ability of DNA ligase to distinguish single nucleotide differences at positions complementary to the termini of co-terminal probing oligonucleotides (see, e.g., Nickerson et al. 1990. *Proc. Natl. Acad. Sci. USA* 87:8923. A modification of this approach, termed coupled amplification and oligonucleotide ligation (CAL) analysis, has been used for multiplexed genetic typing (see, e.g., Eggerding 1995 *PCR Methods App.* 4:337); Eggerding et al. 1995 Hum. Mutat. 5:153).

In another embodiment, genetic bit analysis (GBA) can be used to detect a SNP (see, e.g., Nikiforov et al. 1994. Nucleic Acids Res. 22:4167; Nikiforov et al. 1994. PCR Methods Appl. 3:285; Nikiforov et al. 1995. Anal Biochem. 227:201). In another embodiment, microchip electrophoresis can be used for high-speed SNP detection (see e.g., Schmalzing et al. 2000. *Nucleic Acids Research*, 28). In another embodiment, matrix-assisted laser desorption/ionization time-of-flight mass (MALDI TOF) mass spectrometry can be used to detect SNPs (see, e.g., Stoerker et al. Nature Biotechnology 18:1213).

In another embodiment, a difference in a biological activity of KRC between a subject and a control can be detected. For example, an activity of KRC or a molecule in a signal transduction pathway involving KRC can be detected in cells of a subject suspected of having a disorder associated with aberrant biological activity of KRC. The activity of KRC or a molecule in a signal transduction pathway involving KRC α in cells of the subject could then be compared to a control and a difference in activity of KRC or a molecule in a signal transduction pathway involving KRC in cells of the subject as compared to the control could be used to diagnose the subject as one that would benefit from modulation of an KRC activity. Activities of KRC or molecules in a signal transduction pathway involving KRC can be detected using methods described herein or known in the art.

In preferred embodiments, the diagnostic assay is conducted on a biological sample from the subject, such as a cell sample or a tissue section (for example, a freeze-dried or fresh frozen section of tissue removed from a subject). In another embodiment, the level of expression of KRC or a molecule in a signal transduction pathway involving KRC in cells of the subject can be detected in vivo, using an appropriate imaging method, such as using a radiolabeled antibody.

In one embodiment, the level of expression of KRC or a molecule in a signal transduction pathway involving KRC in cells of the test subject may be elevated (i.e., increased) relative to the control not associated with the disorder or the subject may express a constitutively active (partially or completely) form of the molecule. This elevated expression level of, e.g., KRCor expression of a constitutively active form of KRC, can be used to diagnose a subject for a disorder associated with increased KRC activity.

In another embodiment, the level of expression of KRC or a molecule in a signal transduction pathway involving KRC in cells of the subject may be reduced (i.e., decreased) relative to the control not associated with the disorder or the subject may express an inactive (partially or completely) mutant form of KRC. This reduced expression level of KRC or expression of an inactive mutant form of sKRC can be used to diagnose a subject for a disorder, such as immunodeficiency disorders characterized by insufficient cytokine production.

In one embodiment, the level of expression of gene whose expression is regulated by KRC can be measured (e.g., IL-2).

In another embodiment, an assay diagnosing a subject as one that would benefit from modulation of KRC expression, post-translational modification, and/or activity (or a molecule in a signal transduction pathway involving KRC is performed prior to treatment of the subject.

The methods described herein may be performed, for example, by utilizing pre-packaged diagnostic kits comprising at least one probe/primer nucleic acid or other reagent (e.g., antibody), which may be conveniently used, e.g., in clinical settings to diagnose patients exhibiting symptoms or family history of a disease or illness involving KRC or a molecule in a signal transduction pathway involving KRC.

VI. Kits of the Invention

Another aspect of the invention pertains to kits for carrying out the screening assays, modulatory methods or diagnostic assays of the invention. For example, a kit for carrying out a screening assay of the invention can include an indicator composition comprising KRC or a molecule in a signal transduction pathway involving KRC, means for measuring a readout (e.g., protein secretion) and instructions for using the kit to identify modulators of biological effects of KRC. In another embodiment, a kit for carrying out a screening assay of the invention can include cells deficient in KRC or a molecule in a signal transduction pathway involving KRC, means for measuring the readout and instructions for using the kit to identify modulators of a biological effect of KRC.

In another embodiment, the invention provides a kit for carrying out a modulatory method of the invention. The kit can include, for example, a modulatory agent of the invention (e.g., KRC inhibitory or stimulatory agent) in a suitable carrier and packaged in a suitable container with instructions for use of the modulator to modulate a biological effect of KRC.

Another aspect of the invention pertains to a kit for diagnosing a disorder associated with a biological activity of KRC in a subject. The kit can include a reagent for determining expression of KRC (e.g., a nucleic acid probe for detecting KRC mRNA or an antibody for detection of KRC protein), a control to which the results of the subject are compared, and instructions for using the kit for diagnostic purposes.

VII. Immunomodulatory Compositions

Agents that modulate KRC activity, expression, processing, post-translational modifications, or activity, expression, processing, post-translational modification of one or more molecules in a signal transduction pathway involving KRC are also appropriate for use in immunomodulatory compositions. Stimulatory or inhibitory agents of the invention can be used to up or down regulate the immune response in a subject. In preferred embodiments, the humoral immune response is regulated.

The modulating agents of the invention can be given alone, or in combination with an antigen to which an enhanced immune response or a reduced immune response is desired.

In one embodiment, agents which are known adjuvants can be administered with the subject modulating agents. At this time, the only adjuvant widely used in humans has been alum (aluminum phosphate or aluminum hydroxide). Saponin and its purified component Quil A, Freund's complete adjuvant and other adjuvants used in research and veterinary applications have potential use in human vaccines. However, new chemically defined preparations such as muramyl dipeptide, monophosphoryl lipid A, phospholipid conjugates such as those described by Goodman-Snitkoff et al. J. Immunol. 147: 410-415 (1991) resorcinols, non-ionic surfactants such as polyoxyethylene oleyl ether and n-hexadecyl polyethylene ether, enzyme inhibitors include pancreatic trypsin inhibitor, diisopropylfluorophosphate (DEP) and trasylol can also be used. In embodiments in which antigen is administered, the antigen can e.g., be encapsulated within a proteoliposome as described by Miller et al., J. Exp. Med. 176:1739-1744 (1992) and incorporated by reference herein, or in lipid vesicles, such as Novasome™ lipid vesicles (Micro Vascular Systems, Inc., Nashua, N.H.), to further enhance immune responses.

In one embodiment, a nucleic acid molecule encoding KRC (e.g., a sense or antisense or siRNA molecule or a molecule in a signal transduction pathway involving KRC or portion thereof is administered as a DNA vaccine. This can be done using a plasmid DNA construct which is similar to those used for delivery of reporter or therapeutic genes. Such a construct preferably comprises a bacterial origin of replication that allows amplification of large quantities of the plasmid DNA; a prokaryotic selectable marker gene; a nucleic acid sequence encoding, e.g., a KRC polypeptide or portion thereof; eukaryotic transcription regulatory elements to direct gene expression in the host cell; and a polyadenylation sequence to ensure appropriate termination of the expressed mRNA (Davis. 1997. Curr. Opin. Biotechnol. 8:635). Vectors used for DNA immunization may optionally comprise a signal sequence (Michel et al. 1995. Proc. Natl. Acad. Sci USA. 92:5307; Donnelly et al. 1996. J. Infect Dis. 173:314). DNA vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. 1996. J. Biotechnol. 44:37)). Alternatively, DNA vaccines can be administered by non-invasive means. For example, pure or lipid-formulated DNA can be delivered to the respiratory system or targeted elsewhere, e.g., Peyers patches by oral delivery of DNA (Schubbert. 1997. Proc. Natl. Acad. Sci. USA 94:961). Attenuated microorganisms can be used for delivery to mucosal surfaces. (Sizemore et al. 1995. Science. 270:29)

In one embodiment, plasmids for DNA vaccination can express KRC (or antagonist of KRC as well as the antigen against which the immune response is desired or can encode modulators of immune responses such as lymphokine genes or costimulatory molecules (Iwasaki et al. 1997. J. Immunol. 158:4591).

VIII. Administration of KRC Modulating Agents

KRC modulating agents of the invention are administered to subjects in a 30 biologically compatible form suitable for pharmaceutical administration in vivo to either enhance or suppress immune responses (e.g., T cell mediated immune responses). By "biologically compatible form suitable for administration in vivo" is meant a form of the protein to be administered in which any toxic effects are outweighed by the therapeutic effects of the modulating agent. The term subject is intended to include living organisms in which an immune response can be elicited, e.g., mammals. Examples of subjects include humans, dogs, cats, mice, rats, and transgenic species thereof, including but not limited to the transgenic KRC mouse described herein. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a KRC modulating agent may vary according to factors such as the disease state, age, sex, and weight of the individual, and the ability of peptide to elicit a desired response in the individual. Dosage regimen may be adjusted to provide the optimum therapeutic response. For example, several divided doses may be administered daily or the dose may be proportionally reduced as indicated by the exigencies of the therapeutic situation.

The therapeutic or pharmaceutical compositions of the present invention can be administered by any suitable route known in the art including for example intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). When it is intended that a KRC modulator be administered to cells in the central nervous system, administration can be with one or more agents capable of promoting penetration of KRC polypeptide across the blood-brain barrier.

The KRC modulator can also be linked or conjugated with agents that provide desirable pharmaceutical or pharmacodynamic properties. For example, KRC can be coupled to any substance known in the art to promote penetration or transport across the blood-brain barrier such as an antibody to the transferrin receptor, and administered by intravenous injection. (See for example, Friden et al., 1993, Science 259: 373-377 which is incorporated by reference). Furthermore, KRC can be stably linked to a polymer such as polyethylene glycol to obtain desirable properties of solubility, stability, half-life and other pharmaceutically advantageous properties. (See for example Davis et al., 1978, Enzyme Eng 4: 169-73; Burnham, 1994, Am J Hosp Pharm 51: 210-218, which are incorporated by reference).

Furthermore, the KRC modulator can be in a composition which aids in delivery into the cytosol of a cell. For example, the agent may be conjugated with a carrier moiety such as a liposome that is capable of delivering the peptide into the cytosol of a cell. Such methods are well known in the art (for example see Amselem et al., 1993, Chem Phys Lipids 64: 219-237, which is incorporated by reference). Alternatively, the KRC modulator can be modified to include specific transit peptides or fused to such transit peptides which are capable of delivering the KRC modulator into a cell. In addition, the agent can be delivered directly into a cell by microinjection.

The compositions are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous. KRC can also be incorporated into a solid or semi-solid biologically compatible matrix which can be implanted into tissues requiring treatment.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

Dose administration can be repeated depending upon the pharmacokinetic parameters of the dosage formulation and the route of administration used. It is also provided that certain formulations containing the KRC modulator are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, olyvinylpyrrolidone, cellulose, gelatin, syrup, methyl cellulose, methyl- and propythydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method for the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of this invention, a KRC modulator may be therapeutically administered by implanting into patients vectors or cells capable of producing a biologically-active form of KRC or a precursor of KRC, i.e. a molecule that can be readily converted to a biological-active form of KRC by the body. In one approach cells that secrete KRC may be encapsulated into semipermeable membranes for implantation into a patient. The cells can be cells that normally express KRC or a precursor thereof or the cells can be transformed to express KRC or a biologically active fragment thereof or a precursor thereof. It is preferred that the cell be of human origin and that the KRC polypeptide be human KRC when the patient is human. However, the formulations and methods herein can be used for veterinary as well as human applications and the term "patient" or "subject" as used herein is intended to include human and veterinary patients.

Monitoring the influence of agents (e.g., drugs or compounds) on the expression or activity of a KRC protein can be applied not only in basic drug screening, but also in clinical trials. For example, the effectiveness of an agent determined by a screening assay as described herein to increase KRC gene expression, protein levels, or upregulate KRC activity, can be monitored in clinical trials of subjects exhibiting decreased KRC gene expression, protein levels, or downregulated KRC activity. Alternatively, the effectiveness of an agent determined by a screening assay to decrease KRC gene expression, protein levels, or downregulate KRC activity, can be monitored in clinical trials of subjects exhibiting increased KRC gene expression, protein levels, or upregulated KRC activity. In such clinical trials, the expression or activity of a KRC gene, and preferably, other genes that have been implicated in a disorder can be used as a "read out" or markers of the phenotype of a particular cell.

For example, and not by way of limitation, genes, including KRC, that are modulated in cells by treatment with an agent (e.g., compound, drug or small molecule) which modulates KRC activity (e.g., identified in a screening assay as described herein) can be identified. Thus, to study the effect of agents on a KRC associated disorder, for example, in a clinical trial, cells can be isolated and RNA prepared and analyzed for the levels of expression of KRC and other genes implicated in the KRC associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of KRC or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a KRC protein, mRNA, or genomic DNA in the pre-administration sample; (iii) obtaining one or more post-administration samples from the subject; (iv) detecting the level of expression or activity of the KRC protein, mRNA, or genomic DNA in the post-administration samples; (v) comparing the level of expression or activity of the KRC protein, mRNA, or genomic DNA in the pre-administration sample with the KRC protein, MRNA, or genomic DNA it the post administration sample or samples; and (vi) altering the administration of the agent to the subject accordingly. For example, increased administration of the agent may be desirable to increase the expression or activity of KRC to higher levels than detected, i.e., to increase the effectiveness of the agent. Alternatively, decreased administration of the agent may be desirable to decrease expression or activity of KRC to lower levels than detected, i.e. to decrease the effectiveness of the agent. According to such an embodiment, KRC expression or activity may be used as an indicator of the effectiveness of an agent, even in the absence of an observable phenotypic response.

In a preferred embodiment, the ability of a KRC modulating agent to modulate inflammation or apoptosis in a epithelial cell of a subject that would benefit from modulation of the expression and/or activity of KRC can be measured by detecting an improvement in the condition of the patient after the administration of the agent. Such improvement can be readily measured by one of ordinary skill in the art using indicators appropriate for the specific condition of the patient. Monitoring the response of the patient by measuring changes in the condition of the patient is preferred in situations were the collection of biopsy materials would pose an increased risk and/or detriment to the patient.

It is likely that the level of KRC may be altered in a variety of conditions and that quantification of KRC levels would provide clinically useful information. Furthermore, because it has been demonstrated herein that increased levels of KRC expressed by a cell can shift the cell death regulatory mechanism of that cell to decrease viability, it is believed that measurement of the level of KRC in a cell or cells such as in a group of cells, tissue or neoplasia, like will provide useful information regarding apoptotic state of that cell or cells. In addition, it can also be desirable to determine the cellular levels of these KRC-interacting polypeptides.

Furthermore, in the treatment of disease conditions, compositions containing KRC can be administered exogenously and it would likely be desirable to achieve certain target levels of KRC polypeptide in sera, in any desired tissue compartment or in the affected tissue. It would, therefore, be advantageous to be able to monitor the levels of KRC polypeptide in a patient or in a biological sample including a tissue biopsy sample obtained form a patient and, in some cases, also monitoring the levels of KRC and, in some circumstances, also monitoring levels of TRAF, c-Jun or another KRC-interacting polypeptide. Accordingly, the present invention also provides methods for detecting the presence of KRC in a sample from a patient.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No.: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

This invention is further illustrated by the following examples which should not be construed as limiting. The contents of all references, patents, and published patent applications cited throughout this application, as well as the figures and the sequence listing, are hereby incorporated by reference.

EXAMPLES

The following materials and methods were used throughout the Examples:

Cell Lines, Plasmids and Stable and Transient Transfection Assays

The human embryonic kidney cell line HEK293, the NIH/3T3 fibroblast cells and the macrophage cell line RAW were obtained from ATCC and maintained in Dulbecco's modified Eagle's medium supplemented with 10% fetal calf serum.

HEK293 cells (4×510 5 per well) were seeded in 6 well plates, and 12 h later cells were transfected with EFECTENE™ (Qiagen) with 25 ng of a 2XNFκB-luciferase (Luc) reporter gene plasmid and 0.5 µg of the indicated TRAF and KRC expression vectors. Total amounts of transfected DNA were kept constant by supplementing with control empty expression vector plasmids as needed. Cell extracts were prepared 24 h after transfection, and reporter gene activity was determined via the luciferase assay system (PROMEGA). PRSV-βGal vector (50 ng) was used to normalize for transfection efficiency by measuring β galactosidase activity using the Galacton-PLUS substrate system (TROPIX, Inc.). Whenever indicated, the cells were treated for 4 hours with TNFα or IL-1 (10 ng/ml). To generate stable transfectants, EFECTENE™ mediated transfection of the RAW cell line was performed and clones were selected and maintained in complete medium supplemented with G418 (2 mg/ml).

Yeast Two Hybrid Screen

Figure 2A:
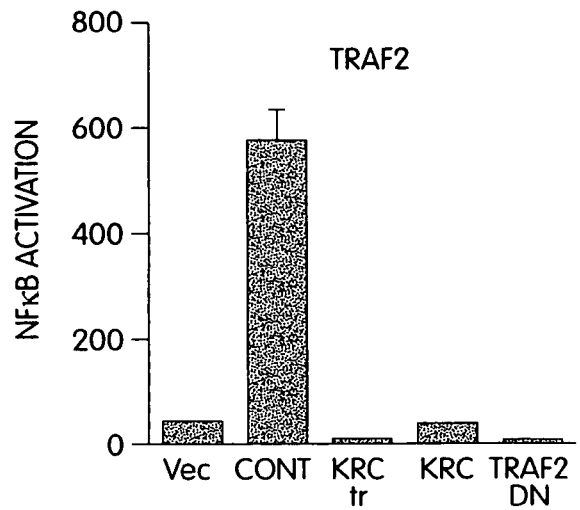
FIGS. 2(A)-2(C) depicts KRC preventing TRAF-dependent NFkB activation. Inhibition of TRAF2 (FIG. 2(A)), TRAF5 (FIG. 2(B)) and TRAF6 (FIG. 2(C)) mediated activation of NFkB by ectopically expressed KRC. 293 T cells ($3\times10^5$) were transfected with 25 ng of NFkB luciferase reporter plasmid, 50 ng of CMVβGal and 1 µg of each indicated plasmid and 24 hours post transfection cells were harvested. Data from at least five experiments normalized for β galactosidase activity are shown. Vec refers to the empty MYC vector without the addition of TRAFs.

The yeast strain EGY48, containing the reporter genes for LEU and β-galactosidase activity under the control of an upstream LexA-binding site was used as a host for the two hybrid screen. The KRC fragment from amino acid 204 to 1055 (KRC tr) (FIG. 2(A)) was fused in frame to the LexA DNA binding domain and a yeast strain expressing the LexA-KRC tr fusion protein was transfected with a mouse Th1 clone cDNA library (Szabo, et al.) fused to the GAL4 transcriptional activation domain. Transformants were plated on agar selection media lacking uracil, tryptophan, leucine and histidine. The resulting colonies were isolated and retested for growth in Leu⁻ plates and for β galactosidase activity. Plasmid DNA was purified from colonies that were Leu⁺ βgal⁺ and used for retransformation of a yeast strain expressing a heterologous bait to determine the specificity of interaction.

Northern Blot Analysis

Total RNA was isolated from transfected RAW macrophage cells using TRIZOL™ reagent (Gibco/BRL) and 15 µg of each sample separated on 0.8% agarose 6% formaldehyde gels, transferred onto GeneScreen™ membrane (NEN) in 20× SSC overnight and covalently bound using a UV Stratalinker™ (Stratagene). Hybridization of blots was carried out at 42° C. as described (Hodge, et al.) using the radiolabeled TNFα, KRC (5850-6210) and HPRT probes prepared with the Random primer kit (Boehringer Mannheim).

Western Blot Analysis

Effectene™ mediated transfections into 293T cells were performed. To prepare cell extracts, cells were washed twice with PBS and lysed for 10 minutes on ice in 1 ml Triton lysis buffer (25 mM HEPES, pH 7.5, 150 mM NaCl, 1% Triton X-100, 10% glycerol, 5 mM EDTA, 2 mM DTT and complete protease inhibitor mixture (Roche Molecular Biochemicals), and the lysates were cleared by centrifugation for 10 min at 14000 rpm. The cell lysates were precleared with 30 µl of protein A/G-Sepharose beads and then incubated for 4 h with 25 µl of anti-MYC antibody directly conjugated to sepharose beads. The immunoprecipitates were then washed 5 times with the lysis buffer, resuspended in SDS sample buffer, and heated at 95° C. for 5 min. Immunoprecipitated proteins were separated by SDS-PAGE, transferred to nitocellulose membrane (Schleicher & Schuell) and western blotting performed by probing with primary antibodies followed by horseradish peroxidase-conjugated goat anti-rabbit IgG and enhanced chemiluminescence according to the manufacturer's instructions (Amersham).

In Vitro Kinase Assay

Anti-HA or anti-FLAG immunoprecipitates were used for immune complex kinase assays that were performed at 30° C. for 30 min with 1 µg of substrate, 10 µCi of $\gamma^{32}$ P ATP, and 10 µM ATP in 30 µl of kinase buffer (20 mM HEPES, pH 7.4, 10 mM MgCl2, 25 mM β-glycerophosphate, 50 µm NA3VO4, and 50 µm DTT). The substrate was GST-c-JUN.

Apoptosis Assay

β-galactosidase cotransfection assays for determination of cell death were performed as described (Hsu, et al.). Transfected NIH 3T3 cells were washed with PBS, fixed in PBS containing 3% paraformaldehyde for 10 min at 4° C., and washed with PBS. Fixed cells were stained overnight with XGal. The number of blue-stained cells was determined microscopically. The average number from one representative experiment of three is shown.

Luciferase Assays

For each transfection, 5×10⁶ Jurkat cells were incubated with either IL2-Luc, NFAT/AP1-Luc or AP1-Luc reporter DNA together with pEF vector or pEF-KRC and CMV-βGAL as normalization control in 0.4 ml of RPMI and transfected by electroporation (260 v, 975 uF). Transfected cells were cultured at 37° C. for 20 h in RPMI 1640 medium (Gibco BRL) supplemented with 10% fetal bovine serum. Transfected cells were stimulated with PMA (50 ng/ml) and ionomycin (2 uM) for 6 hours prior to luciferase (Promega) and β-galactosidase assays (Galacton-PLUS substrate system, TROPIX, Inc).

Reverse Transcription-PCR

Total RNA was isolated from T cells using TRIZOL™ reagent (Gibco/BRL). One (1) µg of total RNA was reverse transcribed using iScript cDNA Synthesis Kit (BioRad). PCR was performed with 2 uM of each primer (listed below) and 2.5 units of Platinum High fidelity enzyme (Invitrogen) according to the manufacturer.

| IL2F | 5'CAAGAATCCAAACTCACCAG3', | (SEQ ID NO:3) |
|---|---|---|
| IL2R | 5'TAGCAACCATACATTCAACAA3' | (SEQ ID NO:4) |
| KRCF | 5'CTCCAATACAGAATTCAAGGGC3', | (SEQ ID NO:5) |
| KRCR | 5'TTTAGGTTGGCCAGTGTGTGTG | (SEQ ID NO:6) |

Jurkat Cell Activation with Raji B Lymphoma Cells and Staphylococcal Enteroxin E (SEE)

Jurkat cells were transfected by electroporation and incubated for 20 h at 37° C. before stimulation for 8 h with the Raji B cell line and Staphylococcal Enteroxin E (SEE) using Raji cells (1:1 with Jurkat cells) and SEE (200 ng/ml).

Pull Down Assays

In vitro translated c-Jun (35$^S$ methionine labeled) and His-KRCtr were incubated for 2 h at 4° C. in binding buffer (PBS/0.25% Nonidet p-40/1 mM PMSF/0.25 mM DTT), incubated for 2 hours with the anti-HIS antibody (Santa Cruz), 30 µl of protein A/G sepharose added and the reaction incubated at 4° C. for an additional 2 h. The immunoprecipitates were then washed five times with the binding buffer, resuspended in SDS sample buffer, and heated at 95° C. for 5 min.

Retroviral Gene Transduction

Activated CD4⁺T cells were transduced by RV, RV-KRC or RV-ZAS2 as described previously (Szabo, S. J., et al. (2000) Cell 100:655-669).

Generation of KRC-Deficient Mice and Subsequent T Cell Stimulation

ES cells were generated in which the entire 5.4 kB exon 2 of KRC was replaced by a neomycin cassette resulting in an allele that produces no KRC protein. KRC+/− ES cells transmitted the disrupted allele to 129/B6 offspring. Heterozygous pups were backcrossed to wild type B6 mice. Mice analyzed were progeny of intercrosses between heterozygous F3 generation backcrossed 129/B6 mice. CD4+ T cells were purified by positive selection from spleen and lymph nodes of 6-8 week old male KRC +/+ and KRC −/− littermates using magnetic beads according to the instructions of the manufacturer (Miltenyi Biotec). Cells were stimulated at $10^6$ cells/mL with plate-bound anti-CD3 (1.0 μg/mL) plus anti-CD28 (0.5 μg/mL). Twenty-four hours later, supernatants were collected and analyzed for IL-2 levels by ELISA. Additionally, cells were stimulated for 72 hours in the presence of 200 U/mL human IL-2, and supernatants were collected and analyzed for IFNγ levels by ELISA.

Example 1

Interaction of KRC with TRAF Family Members in Yeast (A) In this example, a yeast two-hybrid interaction trap was used to select a T cell cDNA library for sequences encoding polypeptides that specifically interacted with a KRC-LexA fusion protein. As bait KRC sequences encoding amino acids 204 to 1055 (KRC tr) were used which include the third zinc finger domain, one of the three acidic domains and the putative NLS sequence, expressed in the pEG202 vector (FIG. 1(A)). One class of interactors encoding a fusion protein with apparently high affinity for the KRC-LexA bait as exhibited by high level of β-galactosidase activity and ability to confer leucine prototrophy was isolated and upon sequencing proved to be the C-terminal segment of TRAF1. The interaction with TRAF1 was specific since no interaction was detected with control plasmids that encode KRC, c-Maf or relA fusion proteins or with the control vector alone (B) The ability of TRAF proteins to interact specifically with KRC in vivo was tested in mammalian cells. KRC sequences 204-1055 were subcloned into a mammalian expression vector which fuses the coding region to an N-terminal epitope tag from a myc peptide, and the expression of the protein confirmed by direct western blot analysis with anti-MYC antibody (FIG. 1(B), right panel). This tagged construct was then cotransfected with TRAF-FLAG-tagged expression plasmids into 293T cells and lysates prepared for immunoprecipitation with an anti-MYC antibody. A STAT4-FLAG-tagged expression construct was used as negative control.

Figure 1B:
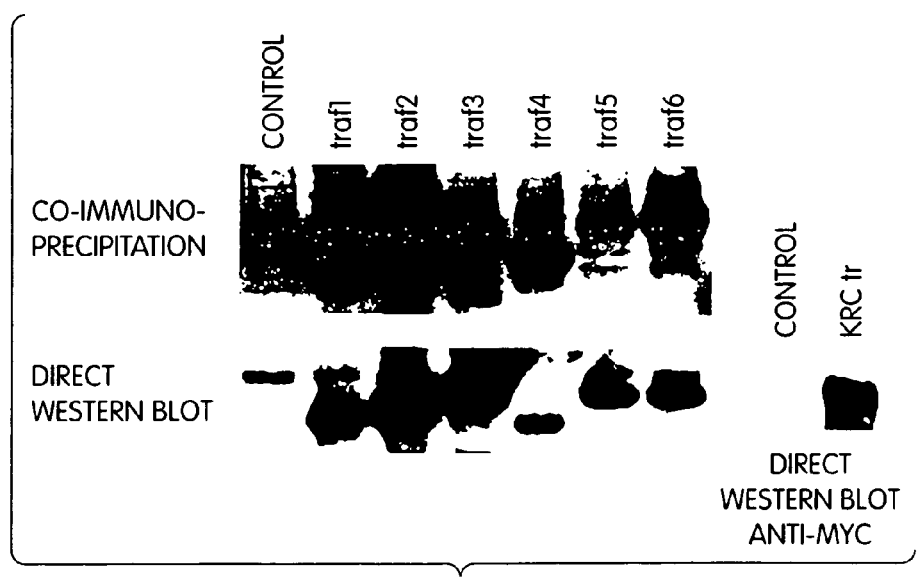

Western blot analysis of these samples using an anti-FLAG-specific monoclonal antibody (mAb) demonstrated that the anti-MYC antibody coimmunoprecipitated all six FLAG-tagged TRAFs, but not the STAT4 control protein (FIG. 1(B), left panel). Finally, the deletion of the ring finger of TRAF2 (TRAF2 DN) did not alter its interaction with KRC (FIG. 1(D)), consistent with our isolation of TRAF1, which lacks the RING finger, in the yeast two hybrid interaction trap screen. These results demonstrate that KRC does interact with all TRAF family members and that this interaction is likely occurring through the TRAF C domain.

Figure 1C:
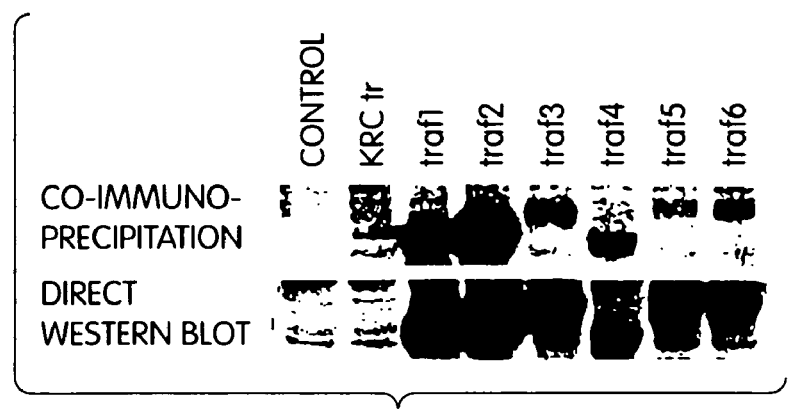
Figure 1D:
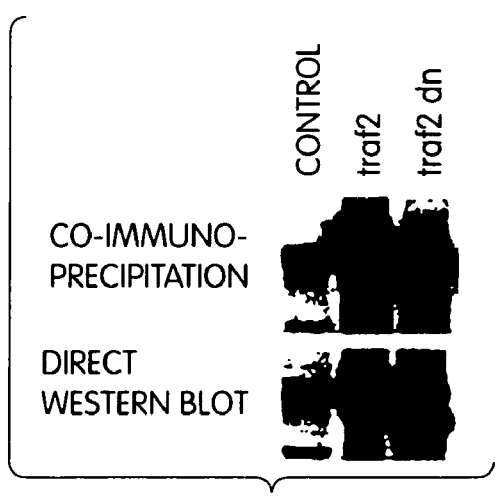

(C) Coimmunoprecipitation assays in the presence of more stringent, higher salt conditions were performed. As shown in FIG. 1(C), when 300 mM rather than 137 mM NaCl was used, TRAF5 was not able to coimmunoprecipitate with KRC, and the amount of TRAFs 3, 4 and 6 that could be immunoprecipitated was reduced. The TRAF-C domain of TRAF1 and TRAF2 share 70% identity but share less than 43% identity with TRAF5 and TRAF( D) To further explore if KRC interacted with a higher affinity with TRAF1 and TRAF2 and with lower affinity with the other TRAF members, we tested the association of endogenous rather than overexpressed TRAFs with ectopically expressed KRC. 293T cells (which lack TRAF1) were transfected with plasmids encoding MYC-tagged KRC or empty vector and 24 hours after transfection cells were lysed. Lysates from 293T cells were incubated with anti-MYC antibody to precipitate KRC.

Figure 1E:
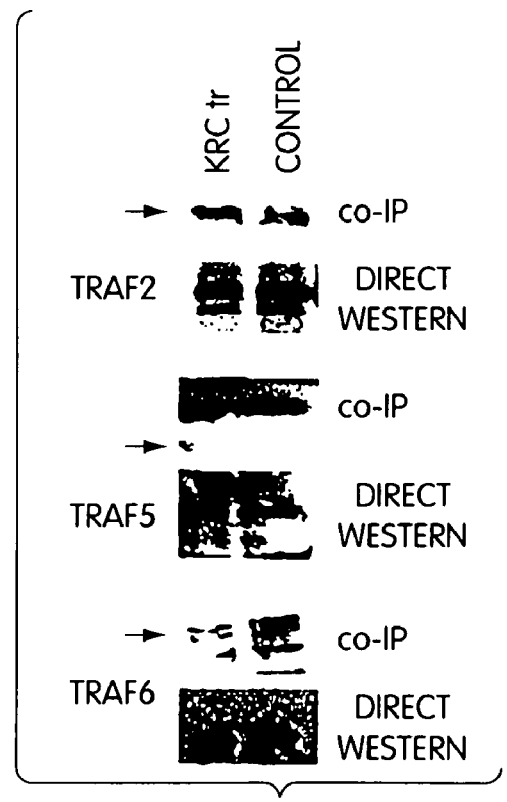

Subsequent Western blotting with anti-TRAF2, anti-TRAF5 or anti-TRAF6 mAbs showed that only endogenous TRAF2 was able to interact with over-expressed KRC (FIG. 1(E)). The bands observed in the TRAFs 5 and 6 coimmunoprecipitants are non-specific Furthermore, treatment of 293T cells with TNF or IL-1 to induce TRAF activity did not affect the strength of the interaction between TRAF2 and ectopically expressed KRC).

Taken together, these data demonstrate that KRC interacts with TRAF family members, that this interaction occurs through the TRAF-C domain, and that KRC interacts with higher affinity with TRAF2 than with TRAF5 and TRAF6. This result is consistent with the higher sequence conservation between the TRAF domain of TRAF1 and TRAF2 than between the other TRAF family members.

Example 2

KRC Prevents TRAF Dependent NFκB Activation

Figure 2B:
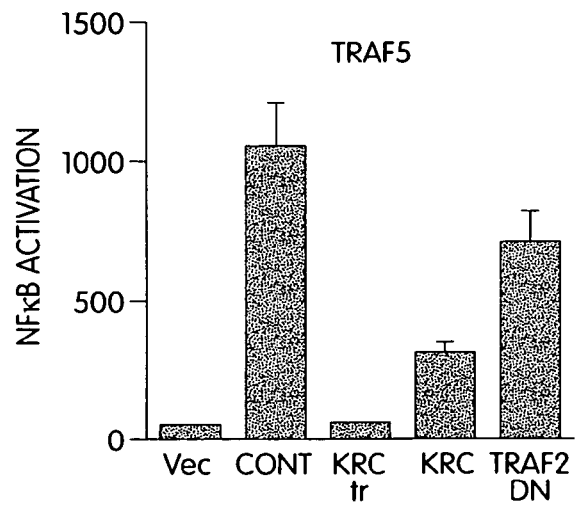
Figure 2C:
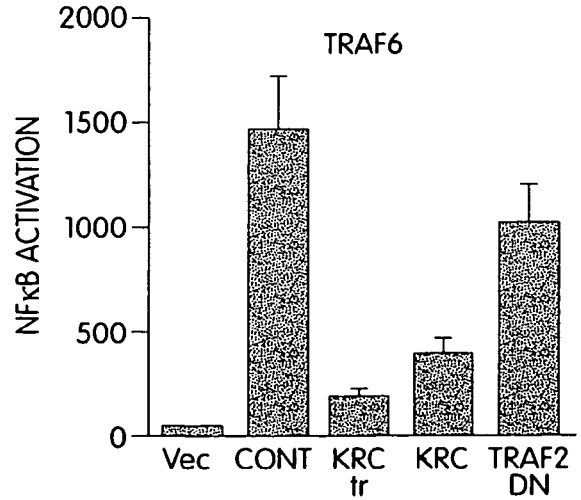

In this example, the effect of KRC overexpression on TRAF2, TRAF5 and TRAF6-induced NFκB dependent gene expression using transfection assays in 293T human embryonic kidney cells was tested. The results show that overexpression of both the full-length KRC and the KRC 204-1055 (KRC truncated, tr) in the absence of exogenous TRAFs blocked NFkB-dependent transactivation in a manner comparable in strength to the inhibition observed with a dominant negative form of TRAF2 (FIG. 2(A)). The results also show that both the KRC tr and the full length KRC blocked TRAF2-induced NFκB activation (FIG. 2(B)) while NFκB activation induced by TRAF5 and TRAF6 were substantially but not completely affected (FIGS. 2(C) and 2(D)).

Example 3

Figure 3A:
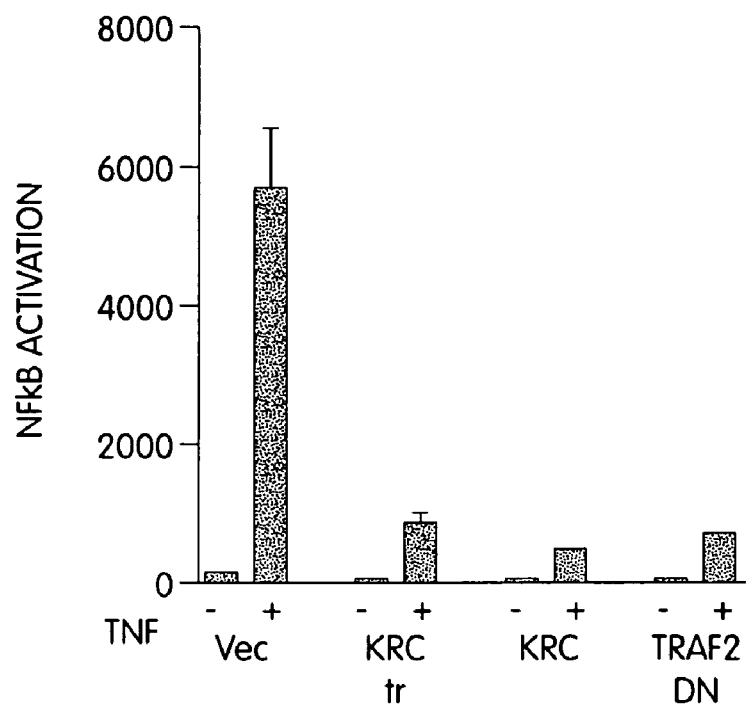
FIGS. 3A-3C shows that KRC and KRC tr inhibit while antisense and dominant negative KRC increase TNFα-driven NFκB transactivation. 293 T cells ($3\times10^5$) were transfected with 25 ng of NFκB luciferase reporter plasmid, 50 ng of CMVβGal and 1 µg of each indicated plasmid and 24 hours post transfection cells were stimulated for 4 hours with 10 ng/ml of TNFα. (A) KRC and KRC tr (B) dominant negative and antisense KRC (C) antisense KRC in the presence of exogenous TRAF2. Data from at least five experiments normalized for β galactosidase activity are shown.
Figure 3B:
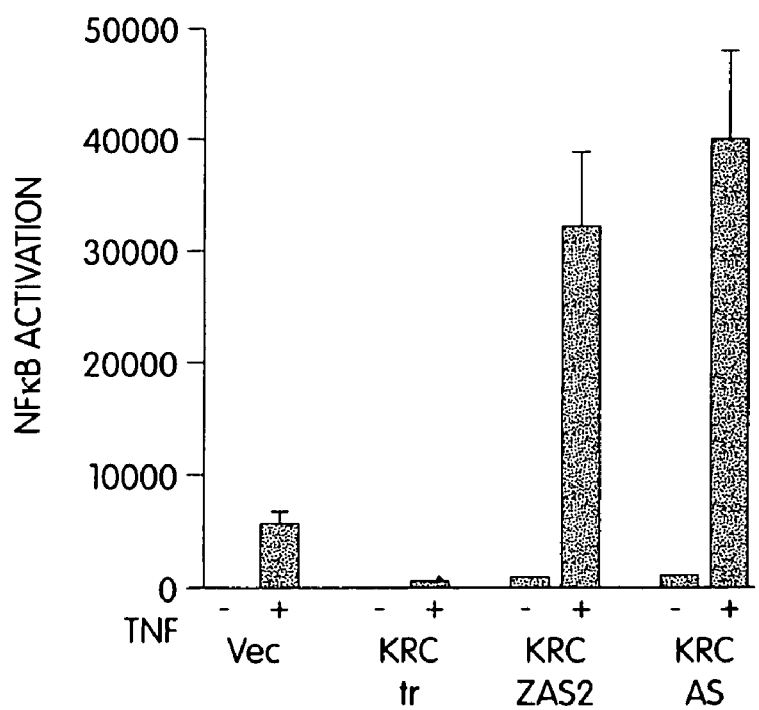
Figure 3C:
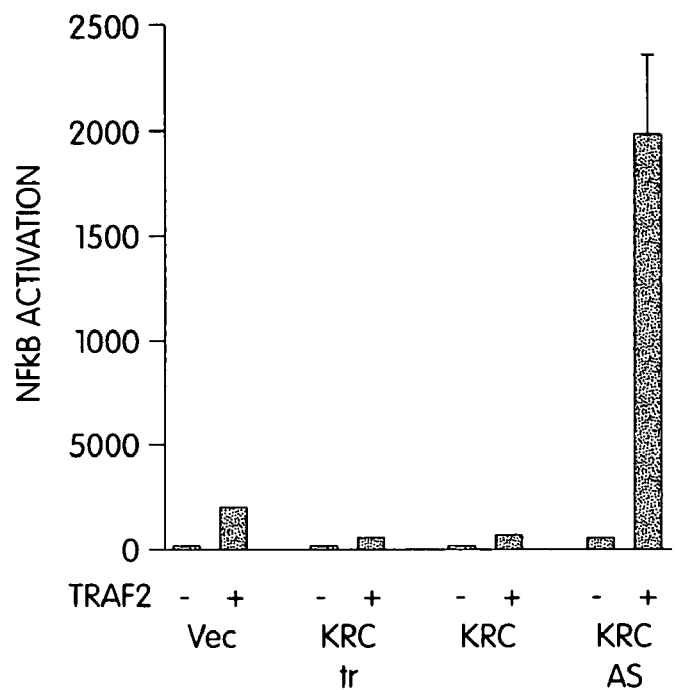

Antisense and Dominant Negative KRC Increase Cytokine Driven NFκB Transactivation while Sense KRC is Inhibitory (A) In this example, whether KRC overexpression affects TNFα-induced NFκB transactivation in 293 cells was tested. FIG. 3 shows that overexpression of KRC or KRC tr in 293 cells strongly inhibited TNFα-induced NFκB activation to a level comparable with the TRAF2 DN effect in the presence of TNFα (FIG. 3(A)). These data are consistent with the demonstrated effect of TRAF2 on NFκB-dependent gene activation in certain cell types, e.g., B cells, as shown in TRAF2-deficient mice (Yeh, et al.).

(B) To manipulate the endogenous KRC, an antisense KRC construct (H10AS) and a dominant negative construct expressing only the ZAS2 domain of KRC (ZAS2) was used (FIG. 1(A)). Both the antisense and the ZAS2 expressing constructs greatly enhanced transactivation of the NFκB reporter upon induction with TNFα (FIG. 3(B)). The same results were obtained with the antisense KRC (FIG. 3(C)) and dominant negative KRC when NFκB-dependent transactivation was driven by exogenous TRAF2 overexpression. These results demonstrate that KRC under normal conditions behaves as a negative regulator of TRAF2-mediated NFκB activation.

Example 4

IKKβ Overexpression Overcomes KRC Inhibition of NFκB-Dependent Transactivation

Figure 4:
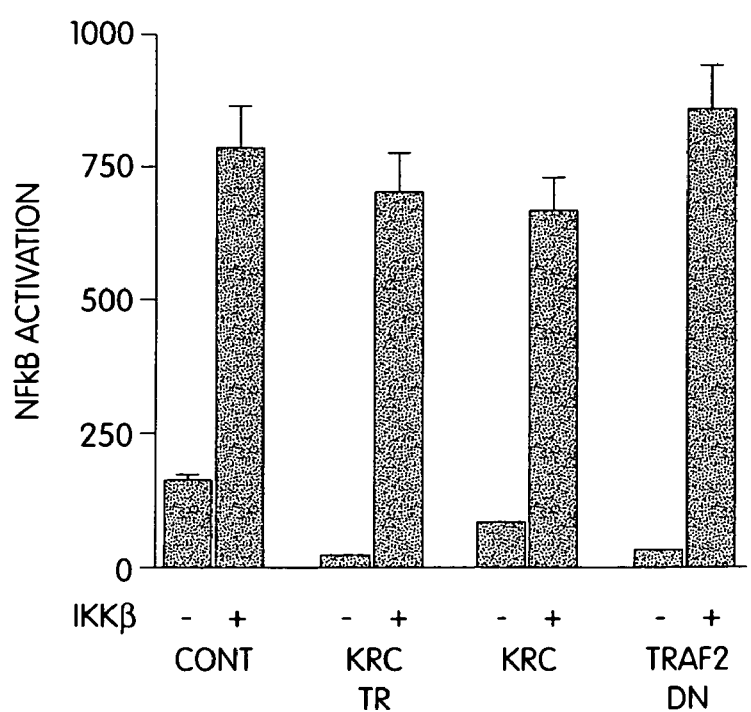
FIG. 4 shows that IKKβ (IκB kinase) overexpression overcomes KRC inhibition of NFκB-dependent transactivation. 293 T cells ($3 \times 10^5$) were transfected with 25 ng of NFκB luciferase reporter plasmid, with 50 ng of CMV βGal, 200 ng of IKKβ expression vector when indicated and 1 μg of each indicated plasmid and cells harvested 24 hours post transfection. Data from two experiments normalized for β galactosidase activity are shown.

In this example, whether KRC affected NFκB-driven gene activation by interfering with upstream events was tested. Full-length KRC or KRC tr, and as a control, the TRAF2 DN mutant, were overexpressed in 293 cells in the absence or presence of ectopic IKKβ (IκB kinase) and the effect on NFκB-mediated transactivation determined. The activation of IKKβ is a key step in the nuclear translocation of the transcription factor NF-κB. IKK is a complex composed of three subunits: IKKα, IKKβ, and IKKγ (also called NEMO). In response to the proinflammatory cytokine tumor necrosis factor (TNF), IKK is activated after being recruited to the TNF receptor 1 (TNF-R1) complex via TNF receptor-associated factor 2 (TRAF2). FIG. 4 demonstrates that overexpression of IKKβ overcomes the inhibitory effect of both KRC and KRC tr in a manner comparable to its effect on TRAF2 DN. Since IKK activation is downstream of TRAF activation, these results demonstrate that the effect of KRC on NFκB-driven gene expression is due to its ability to interact with TRAFs rather than to competition with NFκB for binding to DNA.

Example 5

KRC Increases TNFα-Induced Apoptosis

Figure 5:
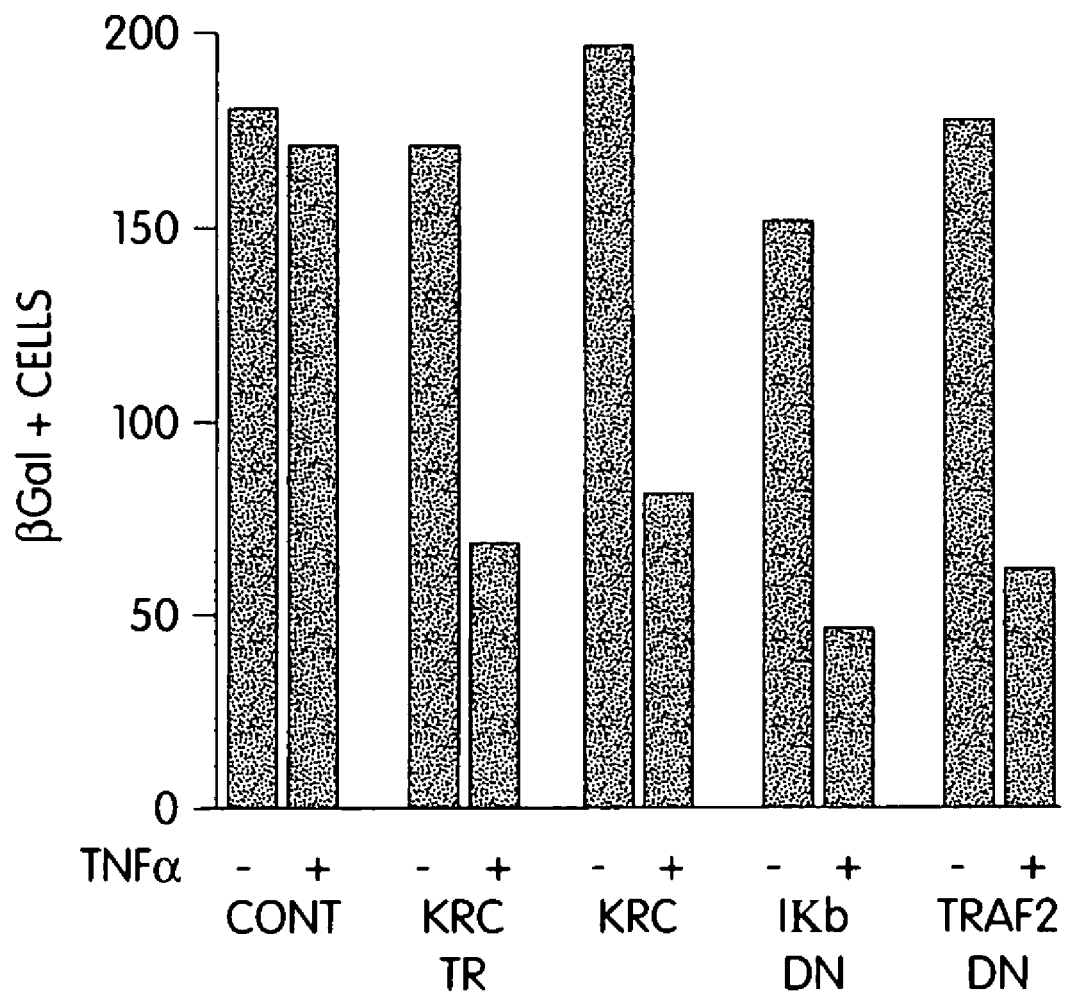
FIG. 5 shows that KRC increases TNFα-induced apoptosis. 3T3 cells were cotransfected with CMV lacZ vector (300 ng per plate) and either empty expression vector or the expression vectors indicated (2 μg of each). Half of the transfected cultured cells were treated with TNFα (20 ng/ml) at 12 hours after the transfection and the other half left untreated. All the cells were fixed and stained at 36 hours after the transfection. The number of blue cells in each transfection was determined by counting six different fields. A representative experiment of three performed is presented.

In this example, whether KRC is involved in the apoptotic process was tested. KRC was overexpressed in 3T3 cells apoptosis was measured by counting β-galactosidase positive (live) cells (FIG. 5). As previously described for HeLa cells, these results demonstrate that in 3T3 cells apoptosis can be induced when either IκB DN or TRAF2 DN are overexpressed in the presence of TNFα, but cannot be induced by TNFα alone (Hsu, et al.; Hsu, et al.; Liu, et al.). KRC overexpression resulted in an increase in TNF mediated cytotoxicity equivalent to that observed with overexpression of IκB or TRAF2 DN. The same effect was observed with the KRC tr construct indicating that KRC likely sensitizes cells to TNFα-induced death by inhibiting NFκB induction, most probably through its effect on blocking TRAF2 function. Collectively, these results demonstrate that upon TNF receptor activation, the NFκB, TRAF1, TRAF2, c-IAP-1 and c-IAP-2 pathways operate as a positive feedback system to amplify the survival signal to protect cells from TNF-induced injury. The interaction of KRC with TRAF2, and possibly with TRAF1 in other cell types, acts to inhibit TRAF activity thereby balance between pro-apoptotic and anti-apoptotic stimuli.

Example 6

KRC Prevents TRAF2 and TNFα-Dependent JNK Activation

Figure 6A:
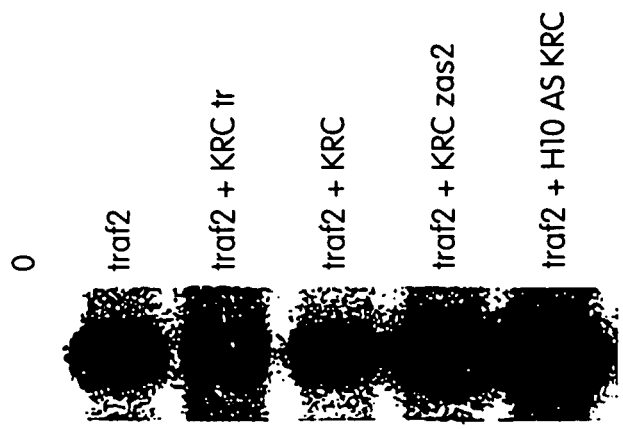
FIGS. 6A-C show that KRC prevents TRAF2 and TNFα-dependent JNK activation. Inhibition of TRAF2 (A) and TNFα (B, C) mediated JNK/SAPK activation by ectopic expression of KRC. (A) 293 T cells were transfected with 400 ng of TRAF2 and 2 μg of the indicated expression vector. Twenty-four hours after the transfection, the cells were harvested and lysed, and the endogenous JNK was precipitated with 5 μg of GST-cJUN (1-79) for 4 hours. JNK activity was determined by using GST-cJUN (1-79) as a substrate. (B,C) 293 T cells were cotransfected with vectors encoding HA-tagged JNK2 (500ng) and the indicated expression vector (2 μg). Twenty-four hours after the transfection cells were stimulated for 10 min with 10 ng/ml of TNFα and cells harvested at varying time points. JNK activity was assayed with GST-cJUN (1-79) as substrate.

In this example, whether KRC could block TRAF2 dependent JNK activation was tested. The KRC 204-1055 tr construct, full length KRC, ZAS2 expressing construct and the antisense KRC were cotransfected into 293 cells together with TRAF2, and JNK activity measured 24 hours after transfection. Both the KRC tr and the full length KRC blocked TRAF2-dependent JNK activation (FIG. 6(A)). Full length KRC blocked JNK activation only partially, likely due to the approximately 10 fold lower expression of this construct as compared to KRC tr. The results also show a dramatic increase of TRAF2 dependent JNK activation with expression of both the antisense KRC as well with the dominant negative ZAS2 expressing construct.

Figure 6B:
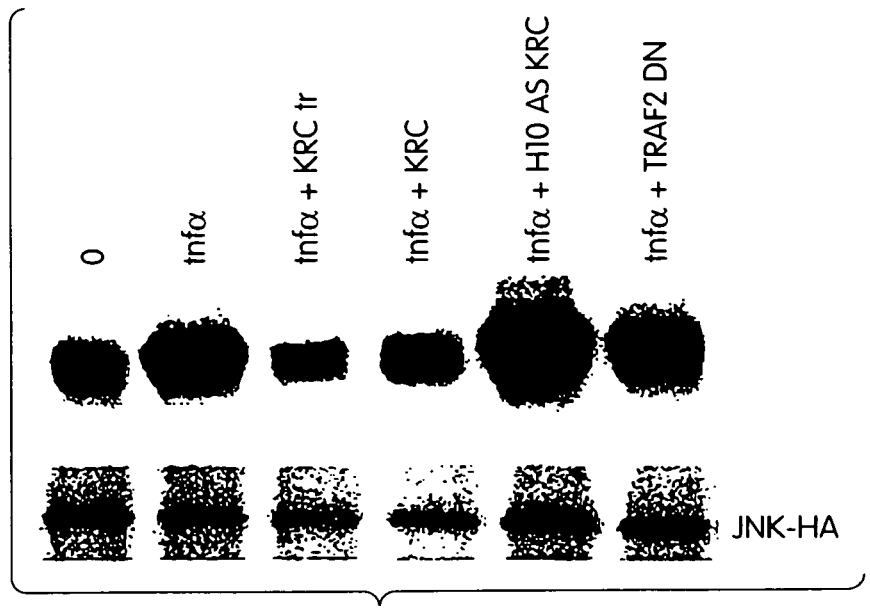
Figure 6C:
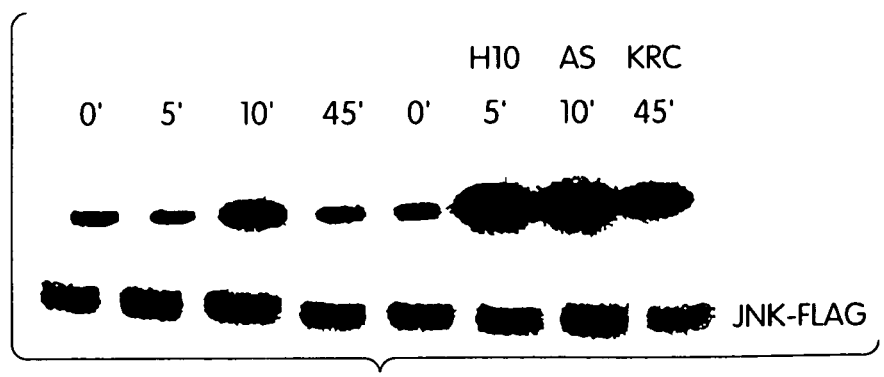

The same results were obtained when JNK activation was induced by treatment with TNFα (FIG. 6(B)). A careful time course of JNK activation was performed, mediated by TNFα in the presence of antisense KRC, which revealed sustained JNK activation as compared to control vector alone (FIG. 6(C)). These results demonstrate that KRC negatively modulates JNK activation by inhibiting TRAF2 function. The immediate target of TRAF2 in TNF-induced JNK/SAPK activation may be the MAP3 kinase ASK1 or members of the GCK family of kinases.

Example 7

KRC is a Negative Regulator of Endogenous TNFα Expression

Figure 7A:
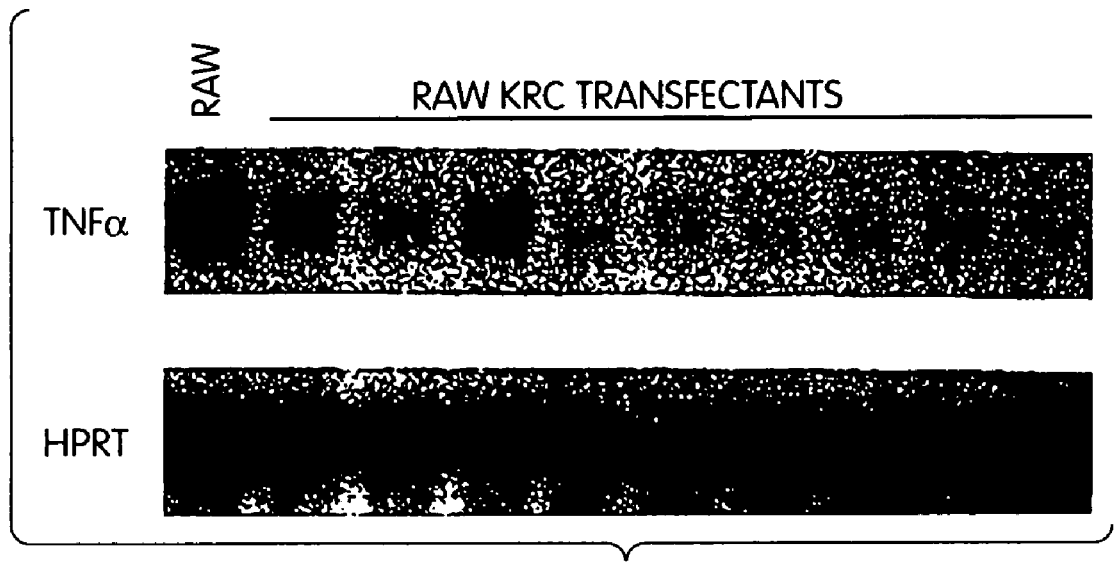
FIGS. 7A-B show that KRC is a negative regulator of endogenous TNFα expression. Northern blotting analysis was performed using total RNA made from RAW cell lines transfected with an empty vector as a control and from a panel of 9 independent RAW clones stably transfected with full-length KRC (upper) and 3 RAW clones stably transfected with dominant negative KRC (lower). The blot was probed with a TNFα cDNA and with HPRT as loading control.
Figure 7B:
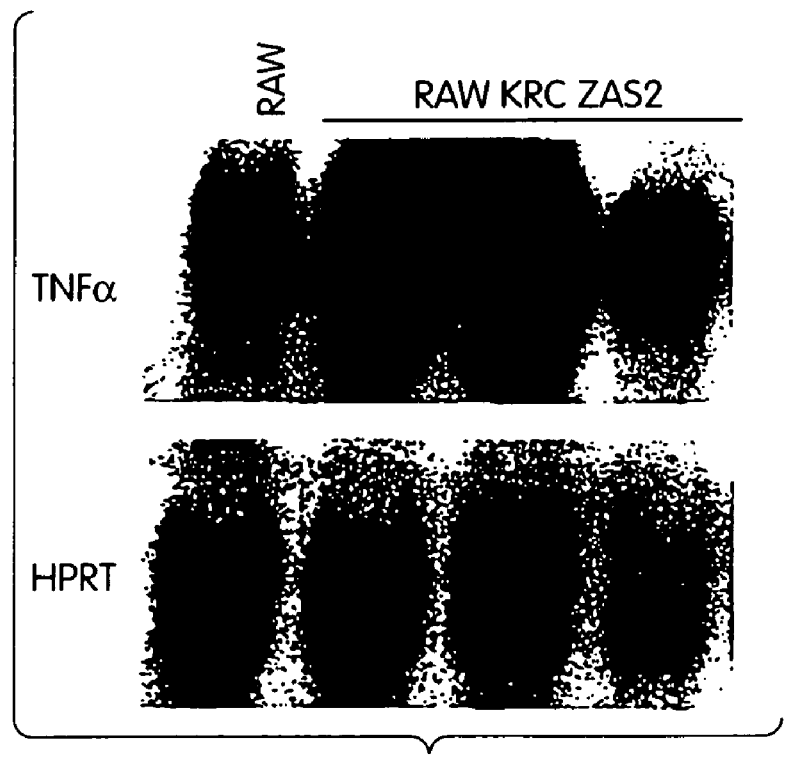

In this example, whether KRC can modulate the expression of endogenous TNFα was tested. Overexpressed KRC or dominant negative KRC was transfected in the RAW macrophage cell line and levels of TNFα in a panel of transfectant clones were analyzed. RAW transfectants stably overexpressing KRC displayed a substantial decrease of baseline TNFα mRNA transcripts when compared to control vector transfected RAW cells while RAW transfectants expressing the dominant negative version had substantial increase in TNFα expression (FIG. 7). These results demonstrate that KRC acts to inhibit the transcription of the TNFα proinflammatory cytokine and that this may occur both through its inhibition of NFκB and JNK signaling pathways.

Example 8

KRC Translocates from Cytosol to Nucleus upon Cell Attachment

Figure 8:
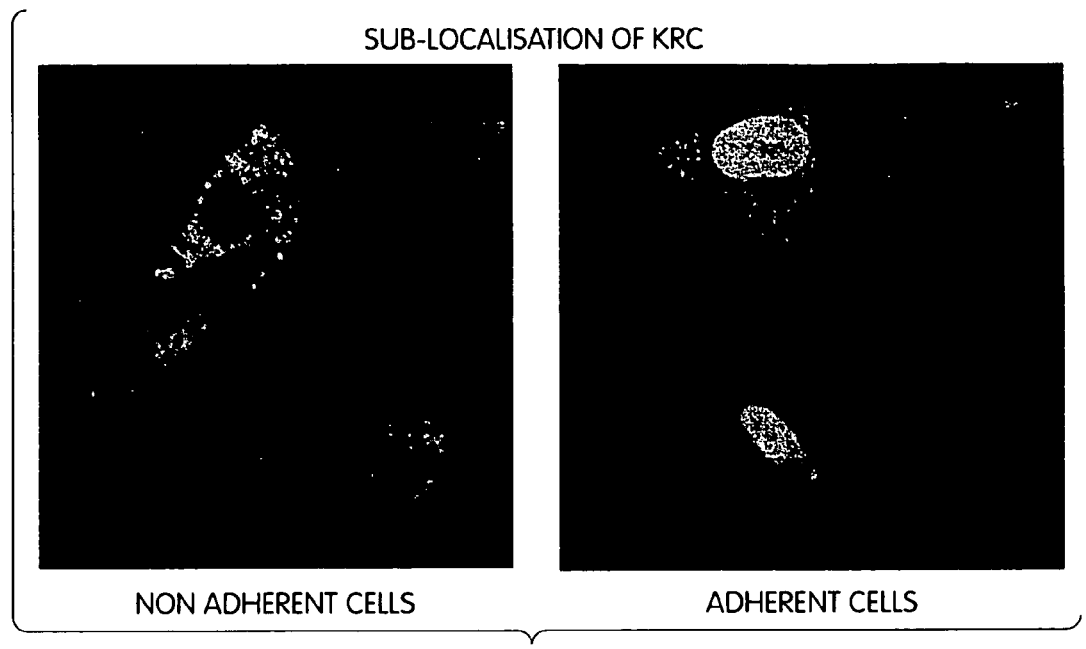
FIG. 8 shows that KRC is present in both cytosol and nucleus. GFP-tagged KRC was stably transfected into NIH 3T3 cells, and cells examined by fluorescence microscopy immediately after trypsinization (left panel) or after adherence to glass slides (right panel).

In this example, how KRC (originally decried as a nuclear protein) physiologically interacts with the predominantly cytosolic TRAF2 to affect gene activation was tested. A full-length KRC was fused to GFP and its cellular localization upon transfection into 3T3 cells was examined. In 3T3 cells in suspension, KRC was mainly localized to the cytosol while in 3T3 cells that had adhered to the glass slide, KRC was primarily present in the nucleus (FIG. 8). These results clearly demonstrate that KRC can reside in the cytosol where it can interact with TRAF2. It should be noted that TRAF2 has recently been described to translocate from cytosol to nucleus as well (Min, et al, 1998). Thus KRC and TRAF2 may well interact in both subcellular compartments.

Example 9

KRC is TH1 Specific

Figure 9:
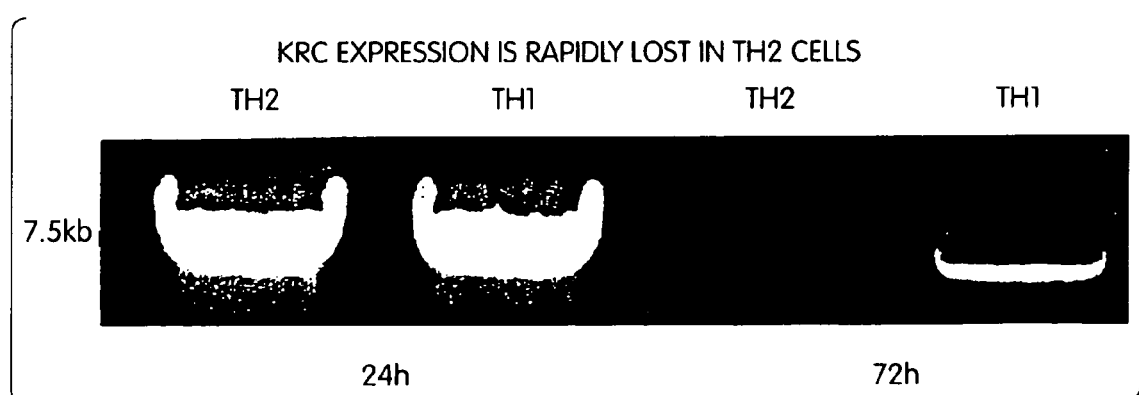
FIG. 9 shows that KRC is Th1-specific. RT-PCR analysis of KRC expression in primary T cells was performed. KRC expression was measured at 24 hours and 72 hours. The results demonstrate that KRC expression is rapidly lost in Th2 cells at 72 hours whereas KRC expression in Th1 cells is maintained at 72 hours.
Figure 10A:
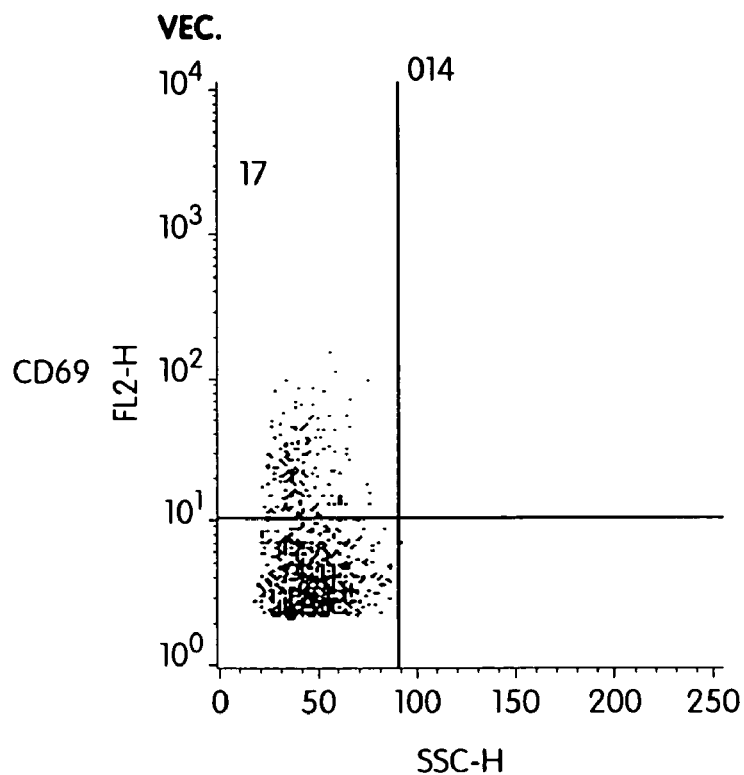
FIGS. 10A-D shows that KRC activates T cells. KRC was transfected into Jurkat T cells and CD69 expression was measured by FACS analysis. The results show that KRC overexpression increases CD69 expression in Jurkat T cells.
Figure 10B:
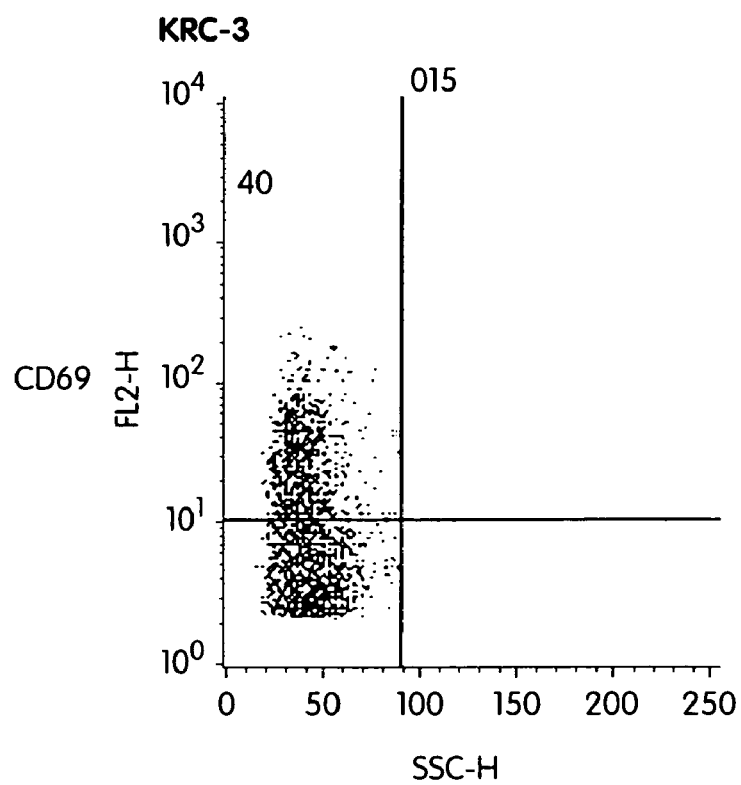
Figure 10C:
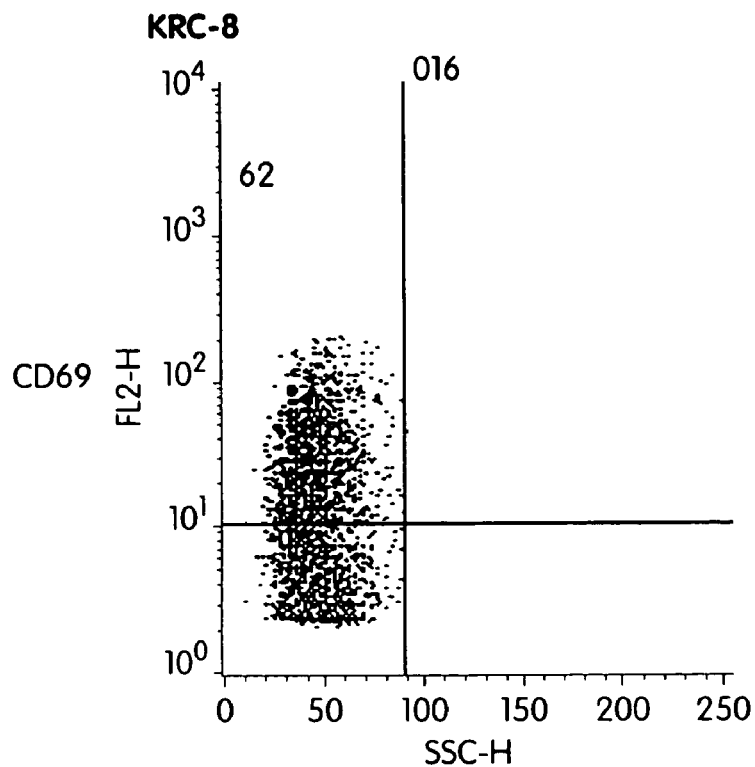
Figure 10D:
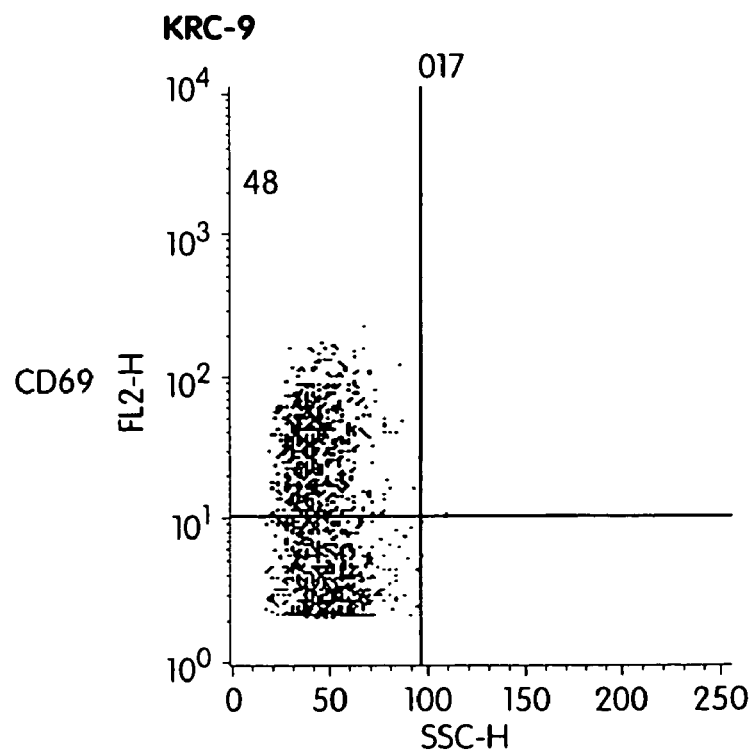

In this example, KRC expression in primary T cells was measured. RT-PCR analysis of KRC expression in primary T cells was performed. KRC expression was measured at 24 hours and 72 hours. The results demonstrate that KRC expression is rapidly lost in Th2 cells at 72 hours whereas KRC expression in Th1 cells is maintained at 72 hours (FIG. 9). These results demonstrate that KRC is Th1 specific.

Example 10

KRC Activates T Cells

In this example, KRC was transfected into Jurkat T cells and CD69 expression was measured by FACS analysis. The results show that KRC overexpression increases expression of CD69 (a T cell activation marker) in Jurkat T cells (FIG. 10).

Example 11

KRC Increases IL-2 Gene Transcription in the Presence of PMA/Ionomycin

Figure 11A:
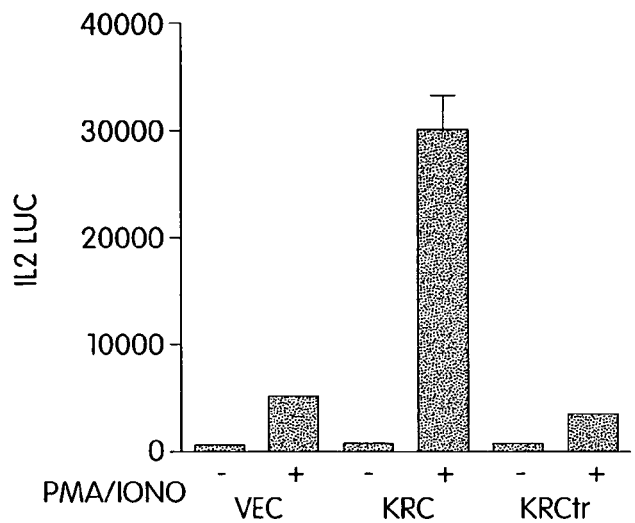
FIGS. 11(A)-11(C) show that KRC increases IL-2 gene transcription in the presence of PMA/Ionomycin and does so primarily through activating AP-1 with no contribution from NFAT.
Figure 11B:
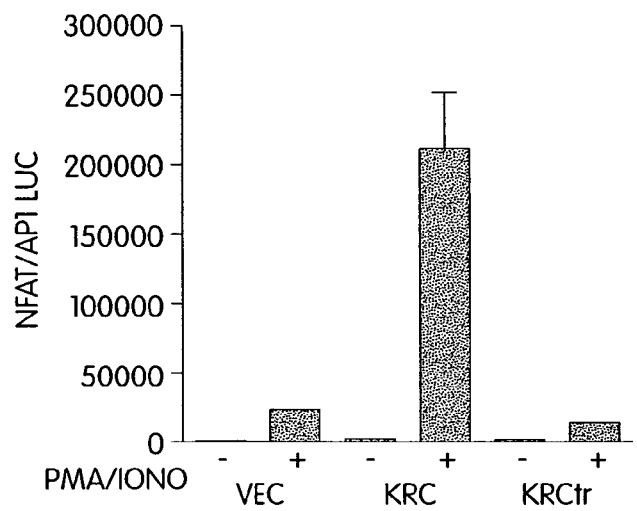
Figure 11C:
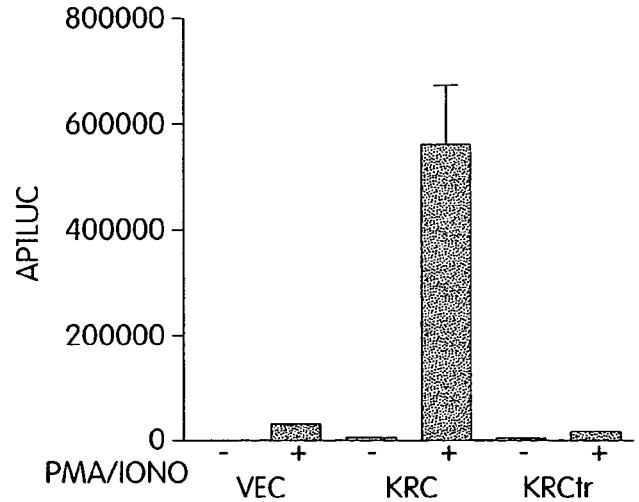

This example shows that KRC increases IL-2 gene transcription in the presence of PMA/Ionomycin. This increase in IL-2 transcription occurs primarily through activating AP-1 with no contribution from NFAT. FIG. 11(A) shows IL-2 promoter transactivation by KRC in Jurkat T cells activated by PMA/Ionomycin. FIG. 11(B) shows transactivation of a composite NFAT-AP1 reporter by KRC. FIG. 11(C) shows transactivation of an AP-1 reporter by KRC.

Example 12

Figure 12A:
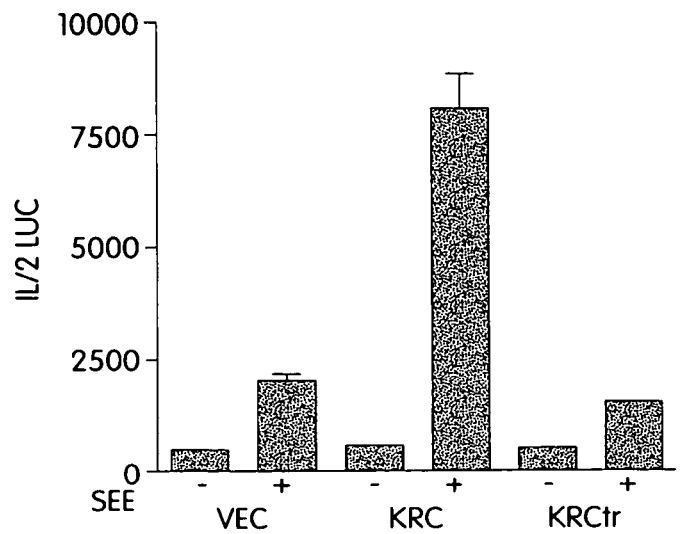
FIGS. 12(A)-12(C) show that KRC increases IL-2 gene transcription in the presence of B cell antigen presenting cells and superantigen SEE and does so primarily through activating AP-1 with no contribution from NFAT.
Figure 12B:
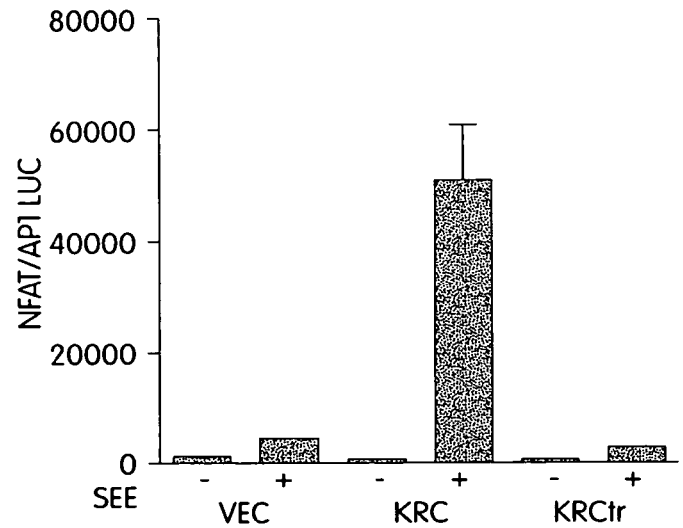
Figure 12C:
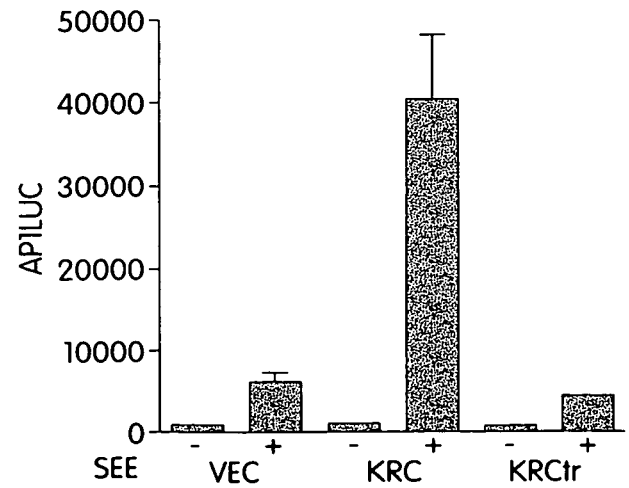

KRC Increases IL-2 Gene Transcription in the Presence of B Cell Antigen Presenting Cells In this example, the results demonstrate that KRC increases IL-2 gene transcription in the presence of B cell antigen presenting cells and superantigen SEE and does so primarily through activating AP-1 with no contribution from NFAT. FIG. 12(A) shows IL-2 promoter transactivation by KRC in Jurkat T cells activated by the Raji B cell APC line and the superantigen SEE. FIG. 12(B) shows transactivation of a composite NFAT-AP1 reporter by KRC. FIG. 12(C) shows transactivation of an AP-1 reporter by KRC.

Example 13

Figure 13A:
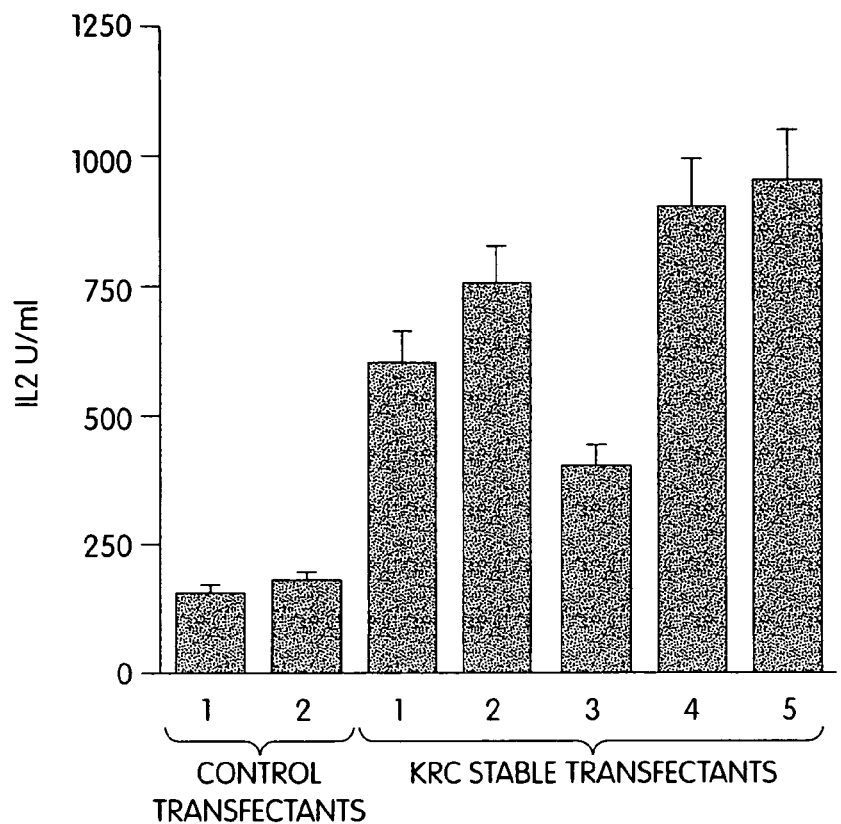
FIGS. 13(A)-13(B) show that KRC IL-2 production. IL-2 production was measured by ELISA.

KRC Overexpression Increases Endogenous IL-2 Production while KRC Loss Decreases Endogenous IL-2 Production In this example, increased IL-2 production in Jurkat T cells stably expressing KRC was measured by ELISA. IL-2 promoter activation requires antigen receptor engagement plus an accessory signal usually supplied by an antigen presenting cell (Jain, J., et al. (1995) Curr. Biol. 7:333-342). Agents that bypass these receptors, such as PMA and ionomycin, can mimic T cell activation in the human T cell lymphoma Jurkat. To assess the function of KRC in T cells, Jurkat cells, which express barely detectable levels of endogenous KRC protein by Western blot analysis, were stably transfected with a plasmid encoding full-length KRC (pEF-KRC) or with vector only control (pEF). G418 drug-resistant Jurkat clones were expanded and analyzed for IL-2 secretion following activation. Clones stably expressing KRC showed clear increases in KRC protein levels, as detected by Western blotting All clones expressing pEF-KRC produced substantially greater amounts of IL-2 upon PMA and ionomycin treatment than activated Jurkat clones transfected with the control vector (FIG. 13(A)). KRC overexpression alone was not sufficient to induce IL-2 secretion, as no IL-2 was detected in the culture supernatants of unstimulated KRC-overexpressing clones These results suggested that KRC is able to boost IL-2 secretion in concert with signals emanating from the TCR.

Figure 13B:
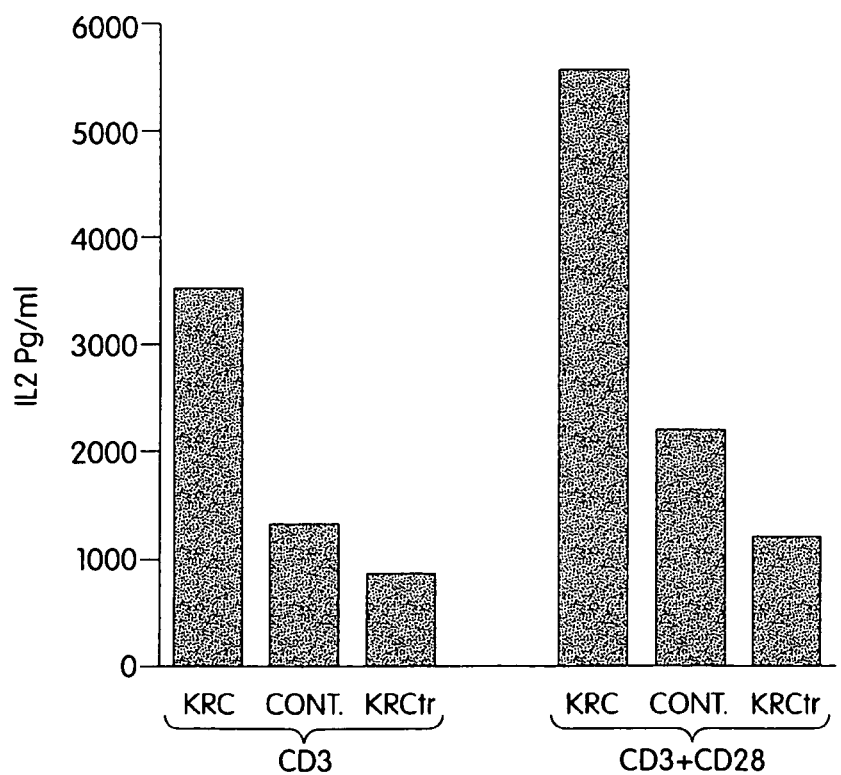

Although the Jurkat model has proved valuable to dissect pathways of T cell signaling, certain observations made in Jurkat cells are irreproducible in primary T cells (Dumitru, C. D. et al. (2000) Cell 103:1071-1083; Weiss, L., et al. (2000) J. Exp. Med. 191: 139-145). Therefore, the effects of KRC overexpression were studied in primary CD4+T cells as well as in the Jurkat line using a retroviral delivery system to express KRC in primary CD4+T cells. Bicistronic retroviral vectors encoding full-length KRC and control GFP were generated. The KRC ZAS2 domain was previously shown to act as a dominant negative in the context of KRC mediated inhibition of TNF-induced NF-κB activation (Oukka, M., et al. (2002) Mol. Cell 9:121-131). Purified CD4+T cells were infected with these retroviruses 36 hours after primary activation with both anti-CD3 and anti-CD28, and sorted by flow cytometry for GFP expression 24 hours after infection. The ability of each population to produce IL-2 following subsequent activation by anti CD3 or anti CD3 plus CD28 was measured at 24 hours post-stimulation. As shown in FIG. 13(B), CD4 cells transduced with full-length KRC produced higher amounts (approximately 3 to 4 fold increase) of IL-2 than CD4 cells infected with the GFP control retrovirus. Furthermore, CD4 cells transduced with the dominant negative KRC ZAS2 domain construct produced significantly less IL-2 than both the full-length KRC and GFP control transduced cells. These data are consistent with the notion that the ZAS2 domain interferes with endogenous KRC activity in T cells to prevent optimal expression of IL-2.

Example 14

KRC Transactivation of AP-1 Depends on RAS, RAF and PKC-Theta

Figure 14A:
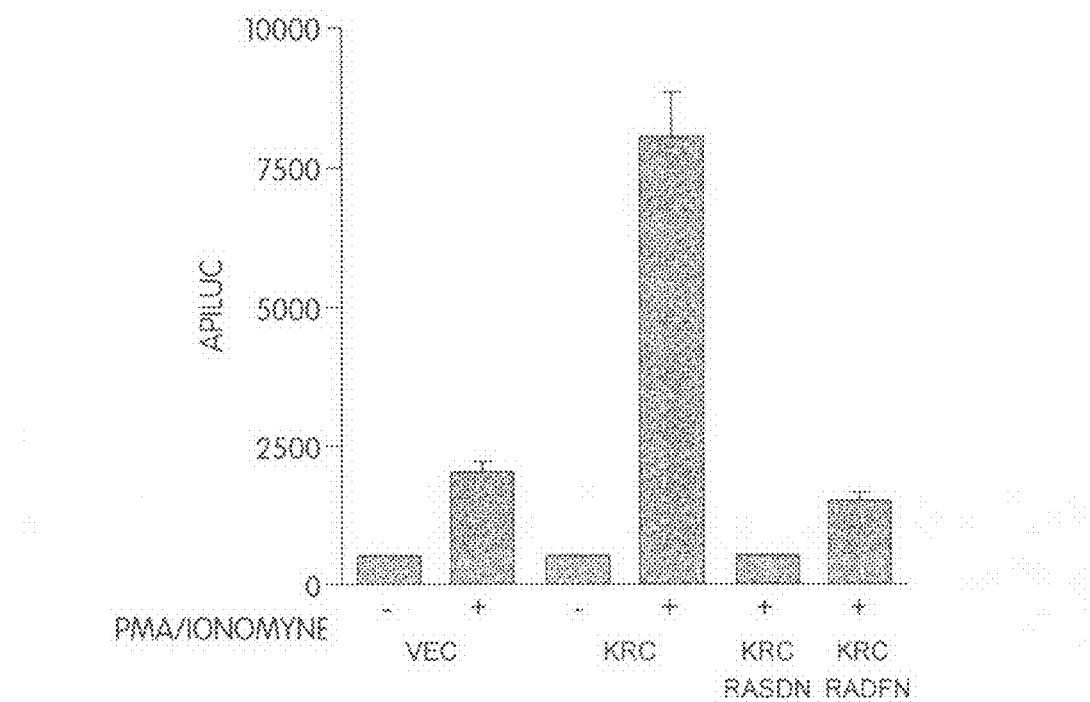
FIGS. 14(A)-14(B) show that KRC transactivation of AP-1 response element depends on Ras, Raf and PKC-theta signaling molecules.
Figure 14B:
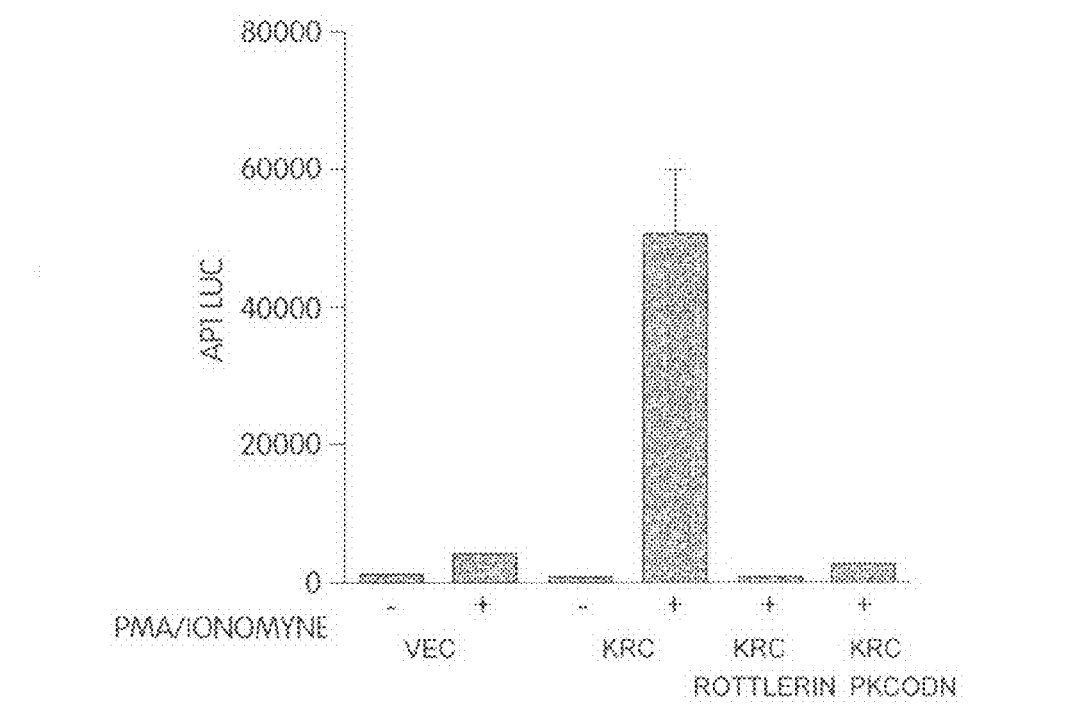

In this example, the results demonstrate that KRC transactivation of AP-1 response element depends on Ras, Raf and PKC-theta signaling molecules. FIG. 14(A) shows KRC transactivation of the AP-1 reporter is blocked by dominant negative Ras and Raf. FIG. 14(B) shows KRC transactivation of the AP-1 reporter is blocked by dominant negative PKC-theta and by the specific PKC-theta inhibitor Rottlerin.

Example 15

KRC Controls IL-2 Expression

Figure 15:
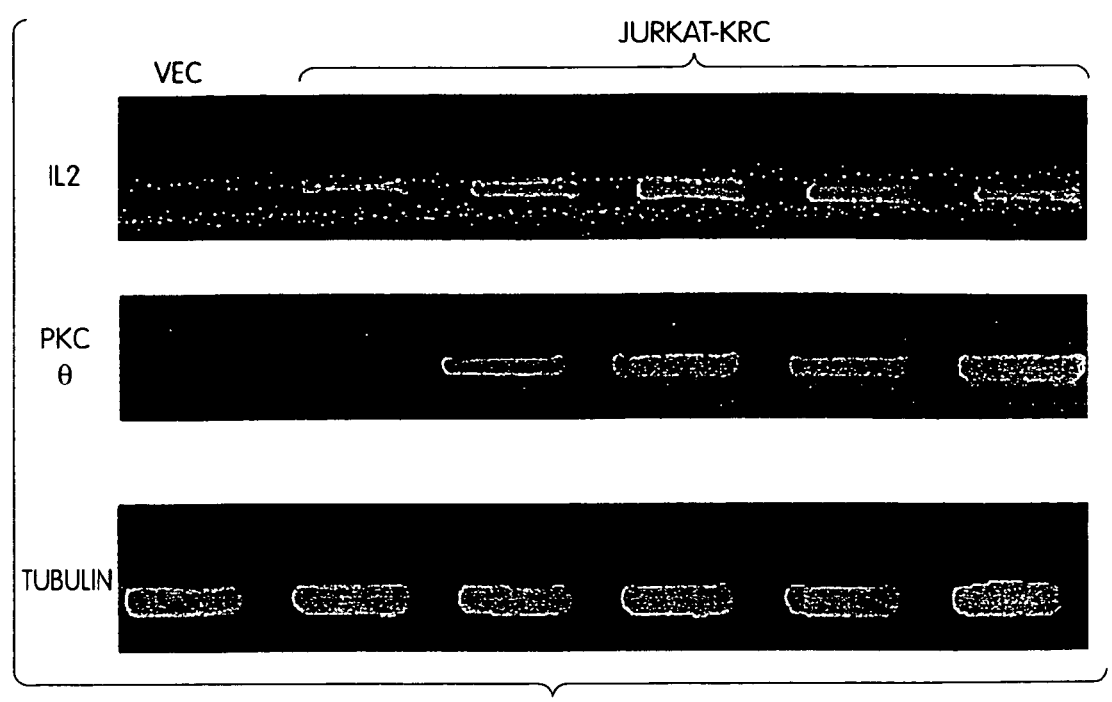
FIG. 15 shows that KRC controls IL-2 expression. RT-PCR of KRC transfected Jurkat clones was performed. The results show increased IL-2 expression.

In this example, the results demonstrate that KRC controls IL-2 expression. RT-PCR of KRC transfected Jurkat clones was performed. The results show increased IL-2 expression upon KRC transfection (FIG. 15).

Example 16

KRC Increases Actin Polymerization

Figure 16:
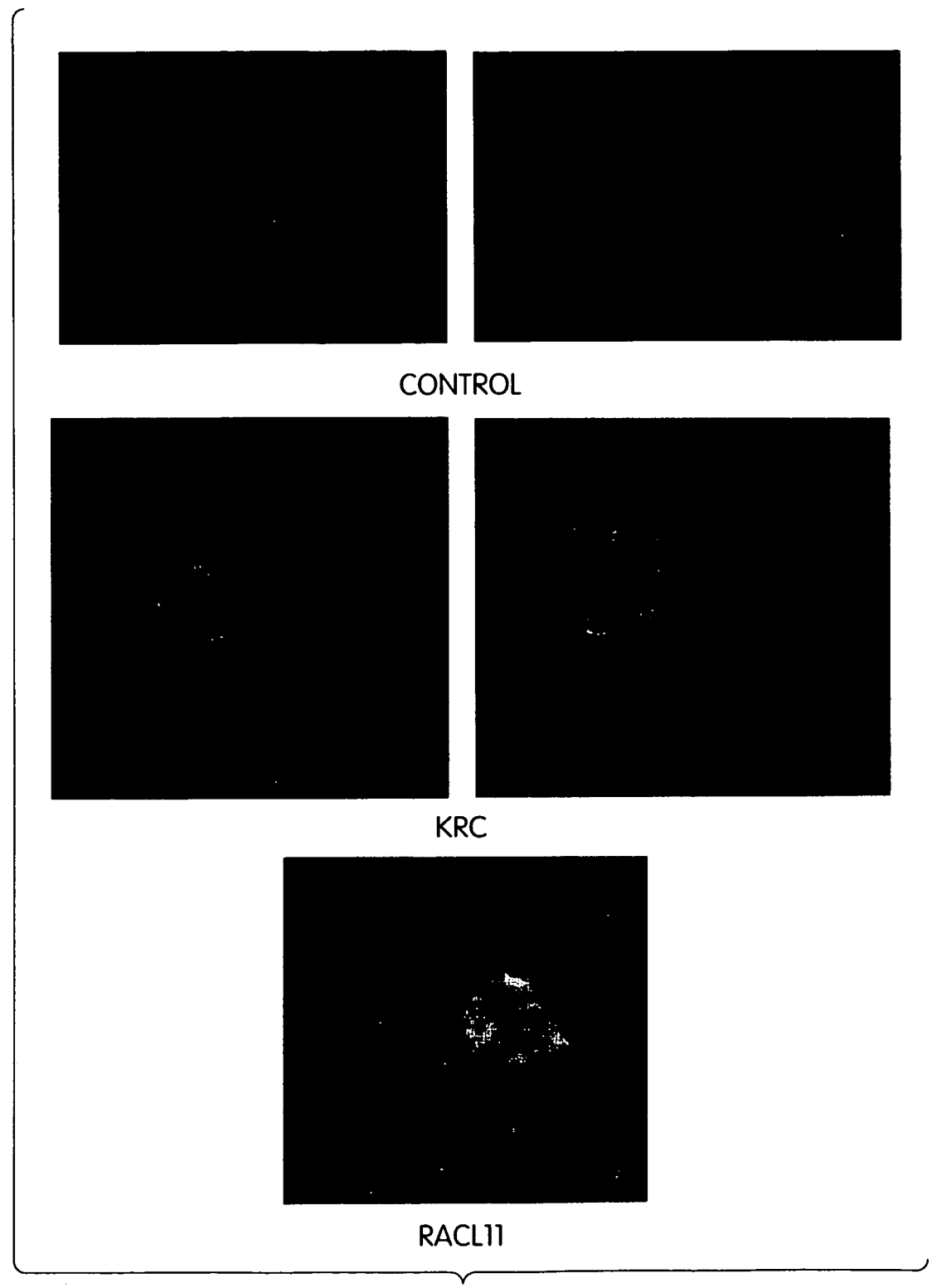
FIG. 16 shows that KRC increases actin polymerization. Immunofluorescence of F-actin upon KRC overexpression in Jurkat T cells was performed. The results show the reorganization of F-actin filaments in KRC transfected Jurkat T cells.

In this example, the results demonstrate that KRC increases actin polymerization. Immunofluorescence of F-actin upon KRC overexpression in Jurkat T cells was performed. The results show the reorganization of F-actin filaments in KRC transfected Jurkat T cells (FIG. 16).

Example 17

KRC Expression Increases in CD4+ Cells Upon Activation

Figure 17:
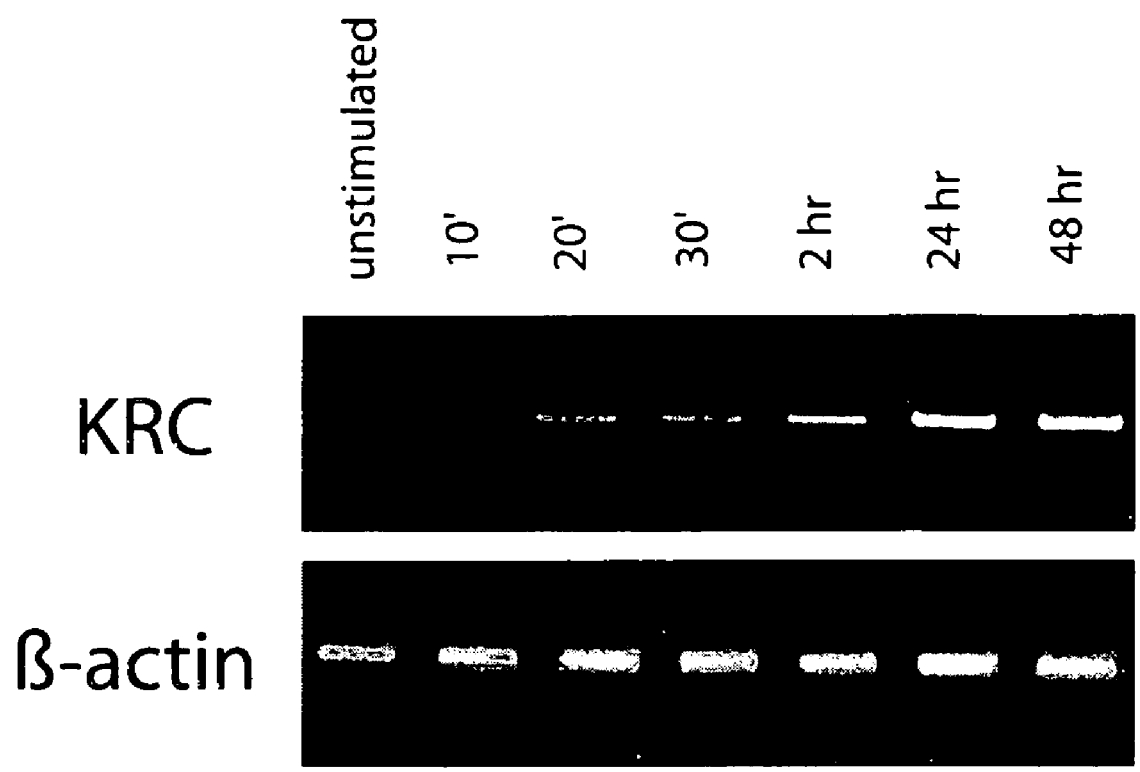
FIG. 17 shows that KRC expression increases in CD4 cells upon activation. Primary C57/B6 CD4+ T cells were stimulated with anti-CD3 (2.0 μg/mL)/anti-CD28 (1.0 μg/mL) antibodies for the indicated times. RNA was prepared and KRC expression was determined by RT-PCR, with β-actin as an internal control.

In this example, the results demonstrate that KRC expression increases in CD4+ cells upon activation with anti-CD3 ((2.0 μg/mL)/anti-CD28 (1.0 μg/mL) antibodies. RT-PCR analysis demonstrates that KRC expression was induced with very rapid kinetics (within 20 minutes) in CD4+ T cells upon activation and increased levels of KRC transcripts were observed throughout the duration of primary CD3/CD28 stimulation, up to 48 hours (FIG. 17).

Example 18

Figure 18A:
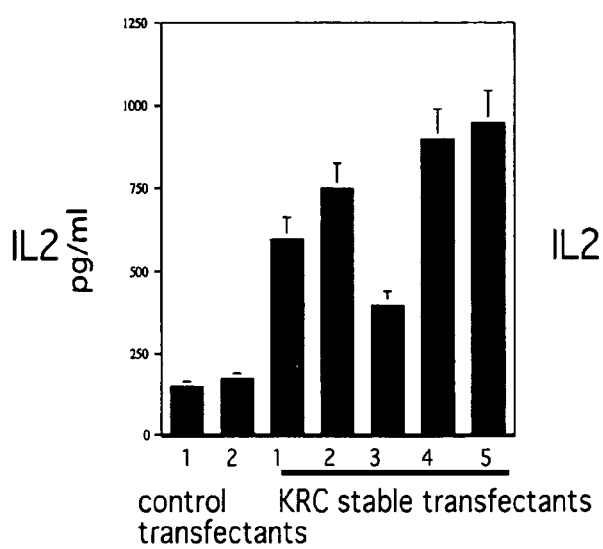
FIGS. 18A-D show that KRC overexpression increases while KRC loss decreases endogenous IL-2 production. In panel A Jurkat T cells were stably transfected with vector (pEF) or KRC expression plasmids. Stable clones were stimulated for 18 hours with PMA (50 ng/mL) plus ionomycin (2 μM) and IL-2 production was measured by ELISA. In panel B Primary CD4+ T cells were activated for 36 hours and subsequently transduced with control (RV), KRC, or KRC dominant negative (ZAS2) bicistronic GFP-expressing retroviruses. GFP-positive cells were sorted and stimulated for 24 hours with anti-CD3 or anti-CD3/anti-CD28 antibodies and IL-2 production was measured by ELISA. In panel C CD4 T cells from KRC +/+ or –/– mice were stimulated with anti-CD3 (1.0 μg/mL)/CD28 (0.5 μg/mL) antibodies for 24 hours and IL-2 production was measured by ELISA. In panel D CD4 T cells from KRC +/+ or –/– mice were stimulated with anti-CD3/CD28 antibodies for 72 hours in the presence of 200 U/mL human IL-2. IFNγ production was measured by ELISA.

KRC Overexpression Increases while KRC Loss Decreases Endogenous IL-2 Production in both Transformed and Primary T Cells IL-2 promoter activation requires antigen receptor engagement plus an accessory signal usually supplied by an antigen presenting cell (Jain, J., C. Loh, and A. Rao. 1995. 7:333-342.). Agents that bypass these receptors, such as PMA and ionomycin, can mimic T cell activation in the human T cell lymphoma Jurkat. To assess the function of KRC in T cells, Jurkat cells, which express barely detectable levels of endogenous KRC protein by Western blot analysis, were stably transfected with a plasmid encoding full-length KRC (pEF-KRC) or with vector only control (pEF). G418 drug-resistant Jurkat clones were expanded and analyzed for IL-2 secretion following activation. Clones stably expressing KRC showed clear increases in KRC protein levels, as detected by Western blotting. All clones expressing pEF-KRC produced substantially greater amounts of IL-2 upon PMA and ionomycin treatment than activated Jurkat clones transfected with the control vector (FIG. 18A). KRC overexpression alone was not sufficient to induce IL-2 secretion, as no IL-2 was detected in the culture supernatants of unstimulated KRC-overexpressing clones. These results suggested that KRC is able to boost IL-2 secretion in concert with signals emanating from the TCR.

Figure 18B:
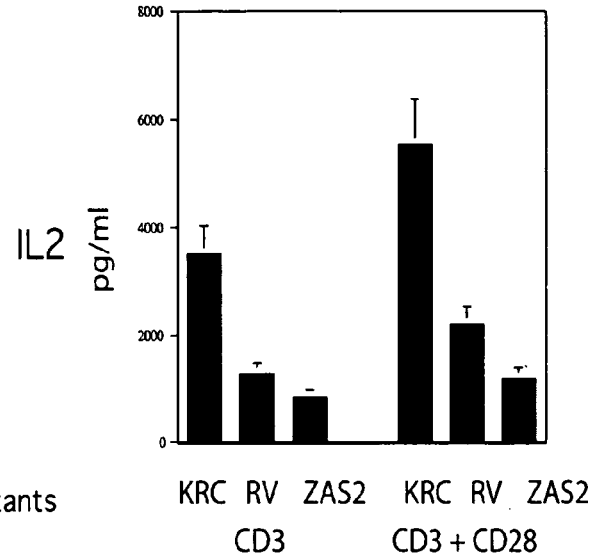

Although the Jurkat model has proved valuable to dissect pathways of T cell signaling, certain observations made in Jurkat cells are irreproducible in primary T cells Although the Jurkat model has proved valuable to dissect pathways of T cell activation and signaling, some observations made in Jurkat cells have not been reproduced in primary T cells (Dumitru, C. D., J. D. Ceci, C. Tsatsanis, D. Kontoyiannis, K. Stamatakis, J.-H. Lin, C. Patriotis, N. A. Jenkins, N. G. Copeland, G. Kollias, and P. N. Tsichlis. 2000. TNF-α induction by LPS is regulated posttranscriptionally via a Tpl2/ERK-dependent pathway. *Cell* 103:1071-1083, Weiss, L. et al. 2000. *J Exp Med* 191: 139-145). Therefore, the effects of KRC overexpression in primary CD4 T cells as well as in the Jurkat line were studied using a retroviral delivery system was used to express KRC in primary CD4 T cells. Bicistronic retroviral vectors encoding full-length KRC were generated, the KRC ZAS2 domain which we have previously shown acts as a dominant negative in the context of KRC mediated inhibition of TNF-induced NF-κB activation (Oukka, .NET al. 2002. *Mol. Cell* 9:121-131), and control GFP. Purified CD4 T cells were infected with these retroviruses 36 hours after primary activation with both anti-CD3 and anti-CD28, and sorted by flow cytometry for GFP expression 24 hours after infection. The ability of each population to produce IL-2 following subsequent activation by anti CD3 or anti CD3 plus CD28 was measured at 24 hours post-stimulation. As shown in FIG. 18B, CD4 cells transduced with full-length KRC produced higher amounts (approximately 3 to 4 fold increase) of IL-2 than CD4 cells infected with the GFP control retrovirus. Furthermore, CD4 cells transduced with the dominant negative KRC ZAS2 domain construct produced significantly less IL-2 than both the full-length KRC and GFP control transduced cells. These data are consistent with the notion that the ZAS2 domain interferes with endogenous KRC activity in T cells to prevent optimal expression of IL-2.

Figure 18C:
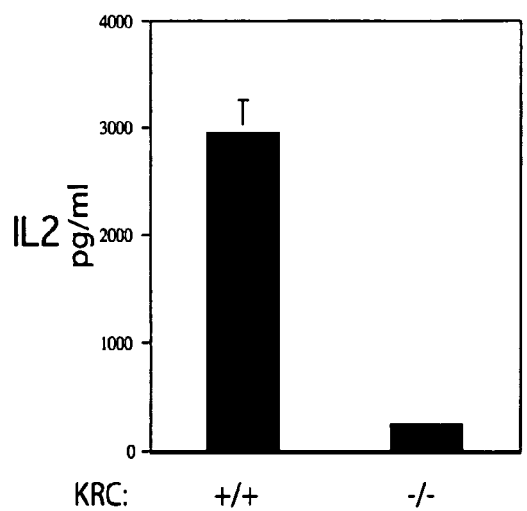
Figure 18D:
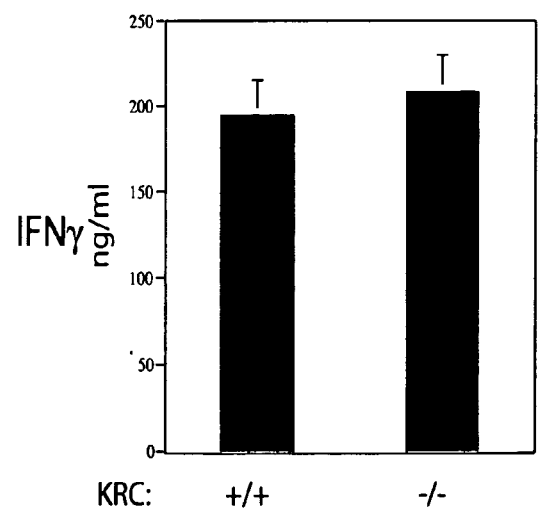

To further analyze the role of KRC in regulating endogenous IL-2 expression, CD4 cells purified from KRC-deficient mice were analyzed. Briefly, lymphoid development in these mice appears normal, with normal numbers of CD4+ T cells isolated from spleen and lymph nodes. Additionally, resting CD4 cells recovered appeared phenotypically normal based on expression of maturation markers such as CD4, CD62L, CD25, CD69 and TCRβ. As shown in FIG. 18C, KRC −/− CD4 cells activated in vitro for 24 hours by CD3/CD28 stimulation produced 10-fold less IL-2 production was detected than in CD4 cells from wild type littermates. However, IFNγ production by these cells following 72 hours of primary stimulation in the presence of excess exogenous IL-2 was normal (FIG. 18D), suggesting that the deficiency of KRC in these cells does not globally inhibit activation-induced cytokine production. Thus, KRC is a positive regulator of IL-2 production both in Jurkat cells and, more importantly, in primary CD4 T cells.

Example 18

KRC Overexpression Increases the Transcription of the IL-2 Gene Through an AP-1-Site-Dependent Mechanism In this example, the results demonstrate that KRC overexpression increases the transcription of the IL-2 gene through an AP-1-site-dependent mechanism.

Figure 19A:
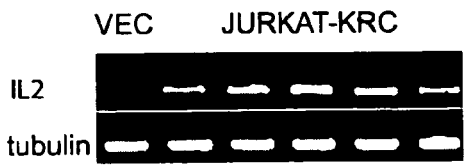
FIGS. 19(A)-19(C) show that KRC overexpression increases the transcription of the IL-2 gene.
Figure 19B:
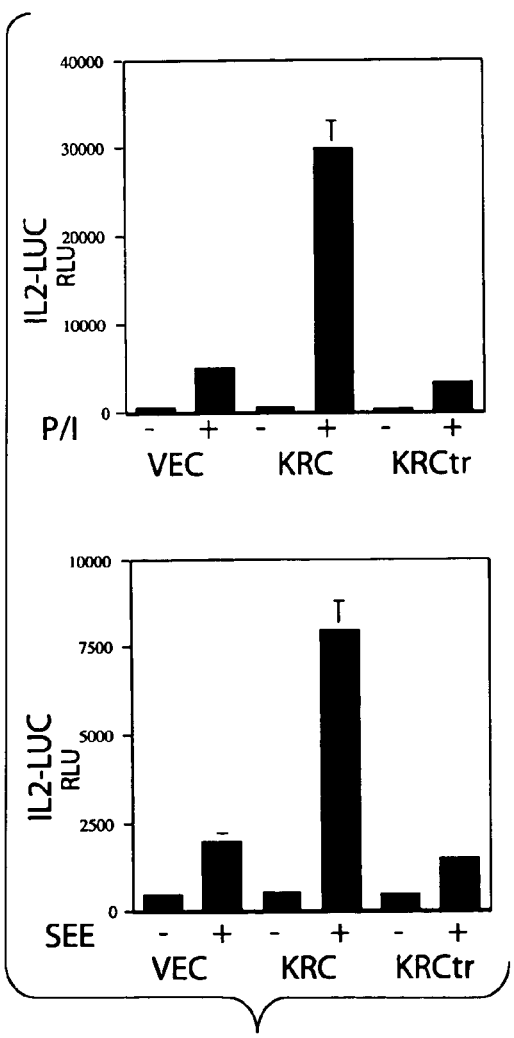

The production of IL-2 by T cells is regulated at multiple levels including transcription, mRNA stability and rate of protein secretion (Lindsten, T., et al. (1989) *Science* 244:339; Jain, J., et al. (1992) *Nature* 356:801-804). In order to define at which stage(s) KRC acts, levels of IL-2 mRNA transcripts were measured by semi-quantitative RT PCR in Jurkat T cells stably transfected with full-length KRC. As seen in FIG. 19(A), Jurkat clones over-expressing KRC displayed higher levels of IL-2 transcripts when activated than Jurkat clones transfected with vector control. Next the ability of KRC to directly transactivate a 1.5 kb IL-2 promoter-luciferase reporter in Jurkat cells was tested. Provision of KRC resulted in an approximately 10 fold induction of luciferase activity in Jurkat cells treated with PMA plus ionomycin (FIG. 19(B), upper panel). Just as KRC overexpression alone did not lead to spontaneous production of endogenous IL-2, no transactivation by KRC was observed in the absence of PMA/ionomycin in these luciferase reporter assays. In order to provide a more physiologic signal to activate Jurkat cells, a model system in which Raji B lymphoma cells act as antigen presenting cells to present staphylococcal enteroxin E (SEE) to Jurkat was utilized. As shown in FIG. 19(B), lower panel, provision of KRC substantially increased (approximately 10 fold) IL-2 promoter activity in this system. Interestingly, KRC had no effect on IL-2 promoter activity in the absence of Jurkat activation either by PMA/ionomycin or by antigen/APC. These data further suggest that KRC expression alone is not sufficient to induce IL-2 mRNA expression; instead, KRC's ability to enhance IL-2 production relies on endogenous factors found only in activated T cells.

Figure 19C:
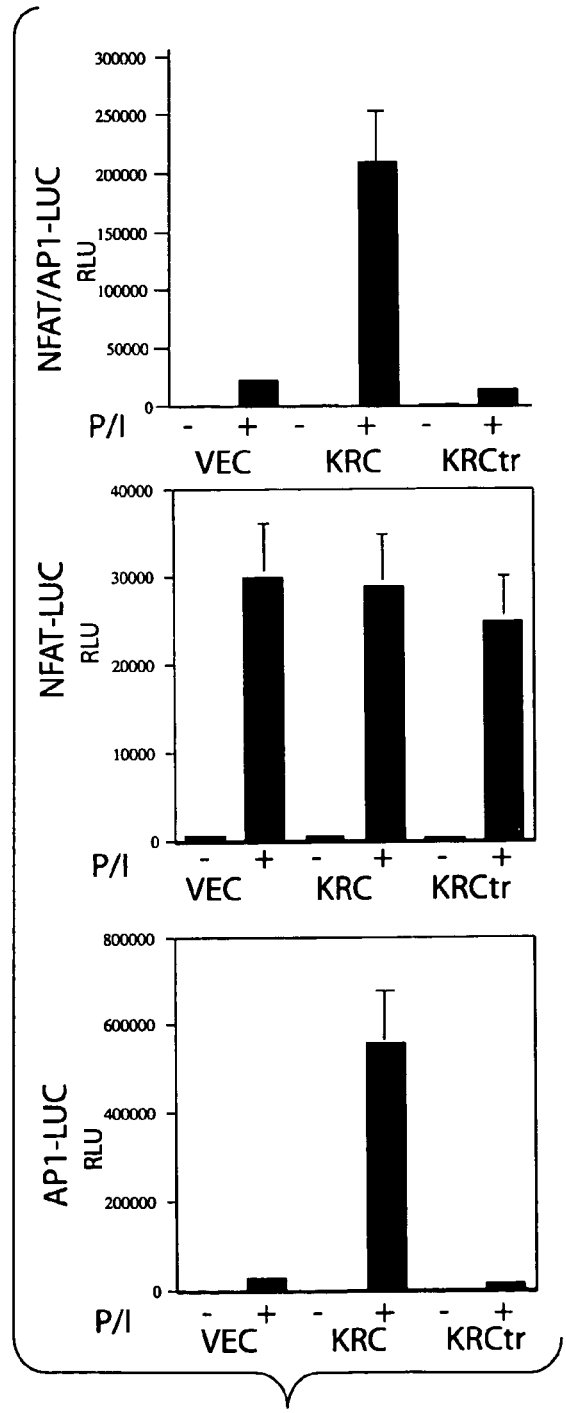

KRC was originally cloned as a transcription factor, however, its effect on gene activation could clearly be ascribed to its function as an adapter protein. Nevertheless, KRC has been shown to bind both NFκB and RSS target sites in vitro and an NFκB site is present in the IL-2 promoter that has been shown to bind the NFκB family member c-Rel (Himes, S. R., et al. (1996) *Immunity* 5:479-489). To test whether KRC overexpression leads to enhanced function of a specific site in the IL-2 promoter and to identify the site, Jurkat cells were cotransfected with KRC and various deletion constructs of the IL-2 promoter. In initial experiments, KRC transactivated a luciferase reporter driven by only 200 bp of the IL-2 proximal promoter. The most prominent regulatory sequences in this region are cis elements that bind members of the NFAT, NFκB, and AP-1 transcription factor families (Jain, J., C., et al. (1995) *Curr. Biol.* 7:333-342; Ullman, K. S., et al. (1993) *Genes & Development* 7:188-196; Rooney, J. W., et al. (1995) *Immunity* 2:473-483; Durand, D. B., et al. (1987) *J. Exp. Med.* 165:395-407), although the NFAT and NFκB cis elements have been shown to overlap. Therefore, whether KRC could transactivate a multimerized linked NFAT/AP-1 target site, or individual multimerized NFAT or AP-1 target sites was tested. KRC enhanced PMA/ionomycin-induced transactivation of a multimerized linked NFAT/AP-1 element and the isolated, multimerized AP-1 element but not the NFAT element (FIG. 19(C)). In contrast to AP-1, the PMA/ionomycin induced activity of NFAT was not further increased by coexpression of KRC. KRC therefore acts at the transcriptional level to increase expression of IL-2 through an AP-1-site-dependent mechanism. Preliminary results show that KRC overexpression enhances, and KRC deficiency decreases, stimulation-induced upregulation of CD69 another AP-1 target gene in T cells (Castellanos, M. C., et al. (1997) *J. Immunol.* 159: 5463-5473).

Example 19

KRC does Not Modulate MAPK Activity

Figure 20A:
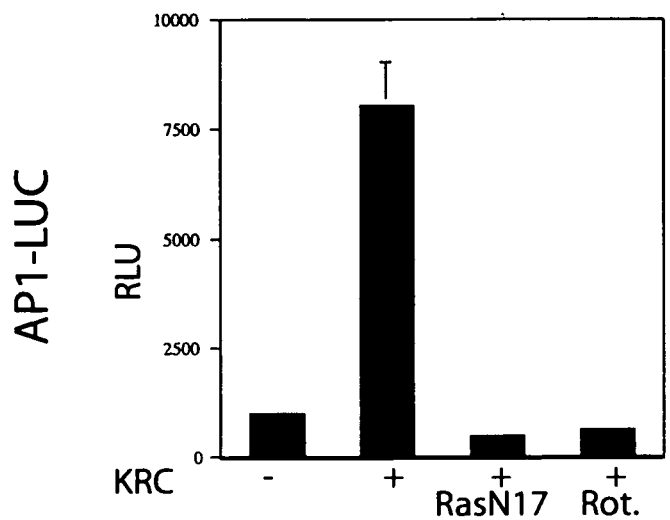
FIGS. 20(A)-20(C) show that KRC does not modulate MAPK activity.

In this example, the results demonstrate that KRC does not modulate MAPK activity. It was unlikely that KRC, a zinc finger protein, transactivated the IL-2 promoter through direct binding to the AP-1 element, especially given the observation that KRC was able to enhance AP-1 activity only when Jurkat cells were simultaneously stimulated through the TCR pathway by PMA or antigen/APC. Indeed in EMSA assays using extracts prepared from unstimulated Jurkat cells overexpressing KRC, no binding to a radiolabeled AP-1 site oligonucleotide was detected. Thus, KRC and AP-1 do not bind the same site within the IL-2 promoter to synergistically increase promoter activity. Additionally, we observed that KRC does not increase AP-1 activity by increasing the expression of c-Jun/c-Fos mRNA An alternative explanation was that KRC acts upstream to enhance posttranslational modifications of AP-1 that increase its activity. For example, N-terminal phosphorylation of c-Jun or C-terminal phosphorylation of c-Fos have been shown to enhance AP-1 activation downstream of the Ras pathway (Dumitru, C. D., et al. (2000) *Cell* 103:1071-1083; Binetruy, B., et al. (1991) *Nature* 351:122-127; Deng, T., and M. Karin (1994) *Nature* 371:171-175). Overexpression of a dominant negative Ras blocks TCR-induced AP-1 activity (Rayter, S. I., et al. (1992) *Embo J.* 11:4549-4556). More recently, it has been shown that mice deficient in PKC theta show defective TCR induced AP-1 activation, suggesting a role for this kinase in Ras/MAPK/AP-1 activation (Sun, Z., et al. (2000) *Nature* 404; Isakov, N., and A. Altman (2002) *Annu. Rev. Immunol.* 20:761-794). Both rottlerin, a PKC theta inhibitor, and overexpression of dominant negative Ras (RasN17) abolished the ability of KRC to enhance AP-1 transactivation following PMA/ionomycin stimulation (FIG. 20(A)). These data are consistent with the placement of KRC downstream of the Ras pathway or with a requirement for two distinct, but interconnected signals for IL-2 promoter transactivation. The latter explanation is more likely since KRC can increase AP-1 activation by Ras but cannot activate AP-1 on its own. Thus, KRC activation of AP-1 requires Ras, and KRC can substantially augment AP-1 activation by the Ras pathway.

Figure 20B:
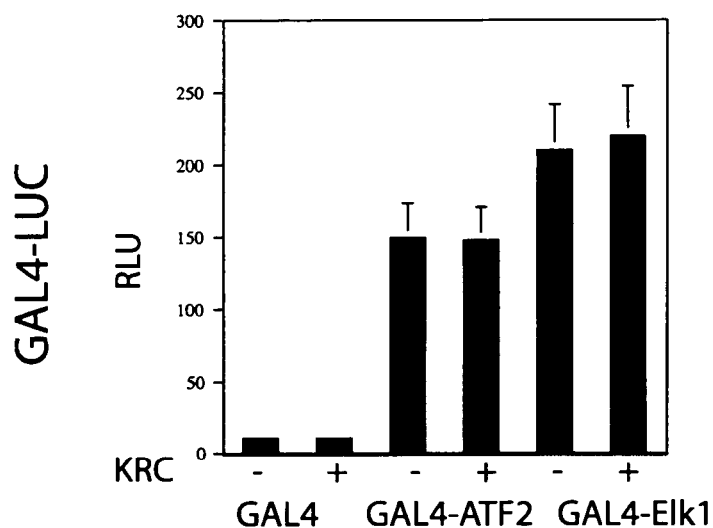
Figure 20C:
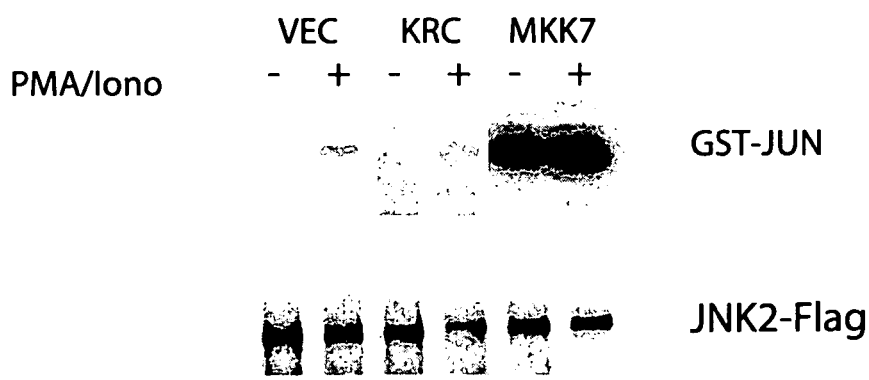

KRC may enhance AP-1 function indirectly through the modulation of MAPK activity, kinases downstream of Ras that are known to potently stimulate AP-1 function (Binetruy, B., et al. (1991) *Nature* 351:122-127; Deng, T., and M. Karin (1994) *Nature* 371:171-175; Murphy, L., et al. (2002) *Nat. Cell Biol.* 4: 556-564). In T cells, stimulation via the TCR or with PMA/ionomycin induces the activation of three MAPKs: ERK, p38 and JNK. The activation of these MAPKS is required for AP-1 transcriptional activity. JNK, in particular, has been shown to increase AP-1 transcriptional activity by phosphorylating c-Jun (Arias, J., et al. (1994) *Nature* 370: 226-229). In initial experiments it was determined that KRC overexpression did not alter levels of transcripts encoding a series of MAP3, MAP2 and MAP kinases as assessed by RNase protection assays (Pharmingen). To test whether KRC had any effect on MAPK activity, a sensitive assay, the PathDetect reporting system, was utilized to evaluate the effect of KRC on ERK-mediated ELK-1 transactivation and p38-mediated ATF2 transactivation. Jurkat cells were co-transfected with a pGAL4-UAS-LUC reporter and I5 expression plasmids encoding GAL4-Elk1 and GAL4-ATF2 fusion proteins, respectively. KRC was unable to modulate either MAPK or p38 activity in this assay (FIG. 20(B)). Co-expression of KRC with HA-ERK1, myc-ERK2, Flag-P38 and Flag-JNK2 was performed and the activity of each kinase was measured using an immunoprecipitation-kinase assay with specific substrates, GST-Elk1, GST-ATF2 and GST-Jun for each MAPK. KRC had no detectable effect on any of the MAPKs in this assay (results for JNK shown, FIG. 20(C)). Therefore, KRC does not increase AP-1 activity through increasing TCR mediated MAPK activity, although it was observed that KRC downregulates TRAF2-mediated JNK activation following TNFα stimulation in macrophage cell lines (Oukka, M., et al. (2002) *Mol. Cell* 9:121-131). Since PMA/ionomycin is a very poor inducer of JNK activation in T cells, the possibility that KRC might also downregulate JNK in T cells under different circumstances cannot be ruled out (e.g., CD28 stimulation). However, the ability of KRC to inhibit low levels of JNK activity following prolonged CD3/CD28 stimulation of naïve Thp cells is unlikely to account for its ability to dramatically enhance AP-1 function and IL-2 production.

Example 20

KRC Physically Interacts with c-Jun and Acts as a Transcriptional Coactivator

In this example, the results demonstrate that KRC physically interacts with c-Jun and acts as a transcriptional coactivator. It has been demonstrated that KRC interacts with the adapter protein TRAF2 to inhibit both NFκB and JNK/SAPK mediated responses including apoptosis and TNFα cytokine gene expression (Oukka, M., et al. 2002. *Mol. Cell* 9:121-131). To investigate whether KRC might therefore physically associate with c-Jun, expression vectors encoding c-Jun and a truncated myc-tagged version of KRC encoding amino acids 204 to 1055 (KRC tr), which includes the third zinc finger domain, one of the three acidic domains and the putative NLS sequence were overexpressed in the 293T kidney epithelial cell line. Coimmunoprecipitation using a monoclonal anti-myc antibody revealed that KRC physically associated with c-Jun (FIG. 21(A)). Further, it demonstrated that the region of KRC shown to associate with TRAF2 (aa 204-1055) also interacted with c-Jun. Similar results were obtained in coimmunopreciptations of overexpressed full-length KRC with c-Jun, although the absolute amounts of c-Jun obtained were less, presumably because the full-length KRC protein is poorly expressed due to its large size (FIG. 21(B)). Further mapping of c-Jun to delineate its interaction site with KRC revealed that KRC interacts with c-Jun amino acids 1-224 fused to the DNA binding domain of GAL4, which includes the transactivation domain Further, this association is direct and does not require posttranslational modifications as shown by the interaction of in vitro translated KRC and c-Jun proteins (FIG. 21(B), right panel). Finally, it was important to demonstrate that this association occurred under physiologic conditions. Untransfected Jurkat or EL4 T cell lines were stimulated with PMA/ionomycin for 45 minutes, and AP-1 complexes were purified by immunoprecipitating c-Jun. FIG. 21(C) shows that endogenous KRC is readily detected in these complexes obtained from stimulated cells.

To further investigate the mechanism via which KRC serves as an AP-1 coactivator, AP-1 was activated by overexpressing c-Jun or c-Jun and c-Fos in 293T cells with an AP-1 luciferase reporter. In this system, overexpression of KRC enhances both c-Jun and c-Jun plus c-Fos AP-1 activity (approximately 5 fold, FIG. 21(C)). However, the presence of endogenous AP-1 proteins might complicate interpretation of these results. Therefore the Gal4 DNA binding domain was fused to the c-Jun or c-Fos transactivation domains and cotransfected these chimeric cDNAs with KRC and a Gal4 binding site-luciferase reporter construct into 293T cells. The chimeric GAL4-c-Jun, but not GAL4-c-Fos, protein potently transactivated the reporter construct in the presence of KRC demonstrating that KRC indeed acts as a transcriptional coactivator (FIG. 21(D)). In sum then, KRC specifically associates with c-Jun under physiologic conditions and this association augments AP-1 transcriptional activity.

Example 21

KRC Physically Associates with c-Jun but not c-Fos

In this example, the results demonstrate that KRC physically interacts with c-Jun but not c-Fos. Expression vectors encoding c-Jun, c-Fos and a truncated myc-tagged version of KRC encoding amino acids 204 to 1055 (KRC tr) which includes the third zinc finger domain, one of the three acidic domains and the putative NLS sequence were overexpressed in the 293T kidney epithelial cell line. Coimmunoprecipitation using a monoclonal anti-myc antibody revealed that KRC physically associated with the c-Jun/c-Fos AP-1 complex. Further, it demonstrated that the region of KRC, aa 204-1055 shown to associate with TRAF2 also interacted with AP-1. KRC appeared to interact with both members of the AP-1 complex. However, 293T cells express endogenous c-Jun. To test definitively whether KRC interacted with both members of AP-1, in vitro translated c-Fos, c-Jun and KRCtr were coimmunoprecipitated using antibodies to c-Jun, c-Fos and KRC. In this assay KRCtr interacted with c-Jun but riot c-Fos. Further, the interaction between KRCtr and c-Jun required only the c-Jun N-terminal portion AA 1-79, termed the delta domain. It was possible that posttranslational modification of c-Fos was required for its interaction with KRC. Alternatively, KRC might interact with c-Fos only when it was associated with c-Jun. Indeed, when c-Jun was present in the lysates, c-Fos coimmunoprecipitated with KRCtr. These experiments revealed that KRC physically associated with c-Jun, but not c-Fos, the high affinity association of c-Fos with endogenous c-Jun presumably leading to the coimmunoprecipitation of c-Fos with KRC observed above. Consistent with this result was the failure to detect association of KRC with c-Fos in a yeast two hybrid assay.

Example 22

Figure 22A:
FIGS. 22(A)-22(D) show that KRC regulates the stability of the c-Jun/c-Fos AP-1 transcription factor by controlling its degradation.
Figure 22B:
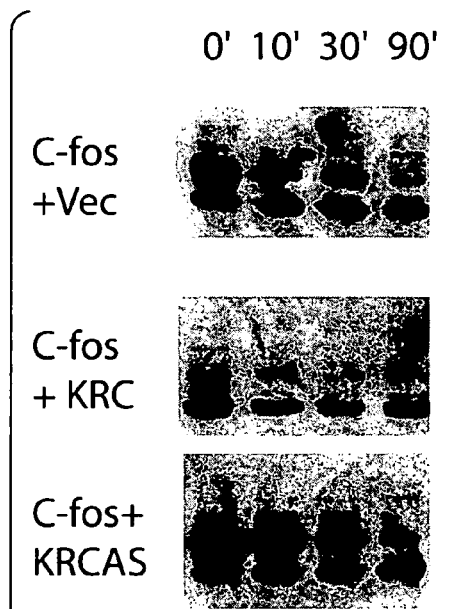
Figure 22C:
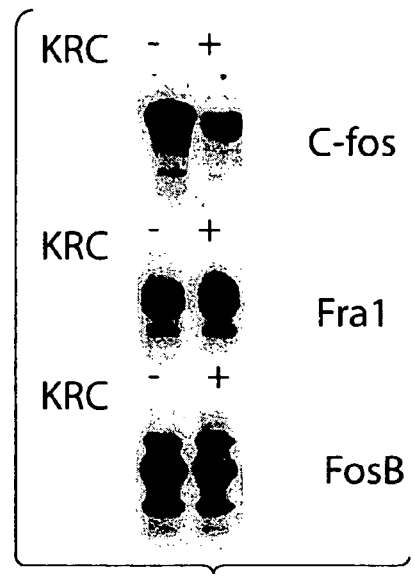
Figure 22D:
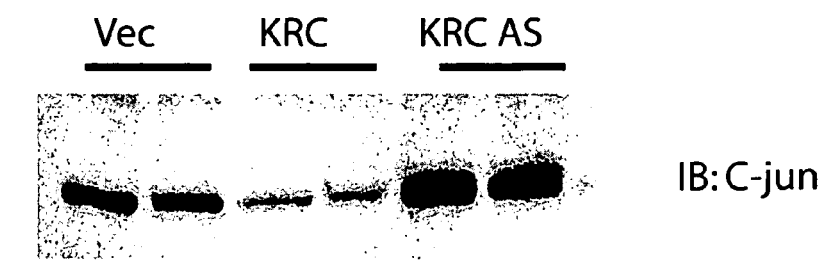

KRC Regulates the Stability of the c-Jun/c-Fos AP-1 Transcription Factor through Controlling its Degradation In this example, the results demonstrate that KRC regulates the stability of the c-Jun/c-Fos AP-1 transcription factor by controlling its degradation. The above experiments mapped the interaction site of KRC with c-Jun to aa 204-1055 of KRC. The interaction of full-length KRC with c-Jun was tested. However, attempts to demonstrate that full-length KRC interacted with AP-1 in overexpression experiments resulted in coimmunoprecipitation of very small amounts of c-Jun and no detectable c-Fos protein when compared to truncated KRC. These results raised the possibility that association of full-length KRC protein with AP-1 might lead to its degradation. Time course experiments were performed in which overexpressed sense KRC or an antisense KRC previously shown to block production of endogenous KRC protein were coimmunoprecipitated with overexpressed c-Jun and c-Fos. Overexpression of full-length KRC, in the presence of low dose cycloheximide to block endogeneous protein synthesis led to the rapid degradation of c-Jun (FIG. 22(B)). Conversely, overexpression of antisense KRC, by inhibiting the expression of endogenous KRC, decreased the rate of c-Jun degradation (FIG. 22(B)). The same set of experiments were performed using c-Fos, a very short-lived cellular protein. As with c-Jun, the stability of the c-Fos protein in the presence of cycloheximide was compromised in the presence of KRC and dramatically stabilized in the presence of the KRC dominant negative expressing only the ZAS2 domain or in the presence of the antisense KRC (FIG. 22(A)). Remarkably, degradation of c-Fos was almost completely abolished in the presence of antisense KRC, suggesting that KRC may be the major protein that controls c-Fos degradation in vivo. The ability of KRC to promote the degradation of other fos family members Fra1, Fra2 and Fos B was also tested (FIG. 23(D)). Only c-Fos protein stability was deceased in the presence of KRC demonstrating the specificity of KRC for the c-Jun/c-Fos AP-1 pair. Viral Fos, an oncogene in acutely transforming retroviruses, contains a frameshift mutation that replaces the last 48 amino acids of c-Fos with an unrelated 49 amino acid-long C terminal tail that renders v-Fos a more stable protein compared to c-Fos. The increased stability accounts in part for the superior transformation ability of v-Fos. The protein stability of V-fos was not affected by altering levels of KRC by sense or antisense overexpression.

Example 23

KRC Regulates the Stability of the c-Jun and c-Fos Based on their Function as Transcriptional Activators In this example, the results demonstrate that the effect of KRC in regulating the stability of c-Jun and c-Fos proteins is reflected in their ability to function as transcriptional activators. To examine the functional consequences of AP-1 degradation by KRC, cotransfection experiments in 293T cells with sense or antisense KRC together with a luciferase-tagged AP-1 reporter construct were performed. Overexpression of sense KRC resulted in decreased stimulation of AP-1 activity while conversely, expression of antisense or DN KRC led to an increase in AP-1 activity. To determine whether KRC alters both the level of activation per cell and the number of cells in which activation or repression occurs we used an AP-1 target site construct fused to GFP. Cotransfection of the AP-1-

GFP construct together with KRC or antisense KRC into 293 cells revealed that KRC reduced both the number of cells in which GFP was expressed as well as the intensity of GFP expression per cell. Conversely, cotransfection of antisense KRC increased AP-1 transactivation as evidenced by an increased number of GFP+ cells as well as an increase in the intensity of fluorescence per cell in. Thus, the effect of KRC in regulating the stability of the c-Jun and c-Fos proteins is reflected in their ability to function as transcriptional activators.

Example 24

KRC is Required for Ubiquination of both c-Jun and c-Fos

In this example, the results demonstrate that KRC is required for ubiquitination of both c-Jun and c-Fos. Much attention has recently been focused on the role of covalent modification in controlling gene transcription in eukaryotes. Lysine modification by ubiquitination, sumoylation and acetylation of transcription factors contributes to their function in modulating gene expression. Previous studies have established that AP-1 proteins are rapidly degraded by the ubiquitin/proteasome pathway. In this pathway, ubiquitin (UB) a 76 amino acid polypeptide is activated by the formation of a thiol ester linkage by the ubiquitin activating enzyme (E1) and is then transferred to the active site cysteine of a ubiquitin carrier protein (E2). Formation of an isopeptide bond between the C terminus of UB and lysines on a substrate is catalyzed by a UB ligase (E3), which binds the substrate and catalyzes the transfer of the UB from a specific E2 to the substrate. The formation of a chain of UB molecules on the substrate then targets it for degradation by the 26 S proteasome. It has been shown that KRC interacts with AP-1 to regulate its degradation raising the possibility that KRC might be the elusive AP-1 E3 UB ligase responsible for its ubiquitination in vivo.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of identifying compounds useful in modulating a biological activity of a mammalian Kappa Recognition Component (KRC) polypeptide comprising:
   a) providing an indicator composition comprising a KRC polypeptide encoded by a nucleic acid molecule which hybridizes to the complement of a nucleic acid molecule set forth in SEQ ID NO: 1 over the full length of the isolated nucleic acid molecule in 6× SSC at 45° C. followed by one or more washes in 0.2× SSC, 0.1% SDS at 65° C., wherein said polypeptide comprises a TNF Receptor Associated Factor (TRAF) interacting domain comprising amino acid residues 204-1055 of SEQ ID NO:2 and two zinc finger-acidic domain structure (ZAS) DNA binding domains, and wherein said polypeptide modulates immune cell proliferation, TNF-α induced apoptosis, and signaling via an NFKB or JNK signaling pathway;
   b) providing a TRAF or c-Jun polypeptide;
   c) contacting the indicator composition with each member of a library of test compounds;
   d) measuring the ability of the KRC polypeptide to interact with the c-Jun or TRAF polypeptide;
   e) determining the ability of the test compound to modulate the interaction of the KRC polypeptide with the c-Jun polypeptide or of the KRC polypeptide with the TRAF polypeptide; and
   f) selecting from the library of test compounds a compound of interest that modulates the ability of the KRC polypeptide to interact with the c-Jun or TRAF polypeptide as compared to an appropriate control, to thereby identify a compound that modulates a biological activity of mammalian KRC polypeptide.

2. A method of identifying compounds useful in modulating a biological activity of a mammalian Kappa Recognition Component (KRC) polypeptide comprising:
   a) providing an indicator composition comprising a KRC polypeptide encoded by a nucleic acid molecule which hybridizes to the complement of a nucleic acid molecule set forth in SEQ ID NO: 1 over the full length of the isolated nucleic acid molecule in 6× SSC at 45° C. followed by one or more washes in 0.2× SSC, 0.1% SDS at 65° C., wherein said polypeptide comprises a TNF Receptor Associated Factor (TRAF) interacting domain comprising amino acid residues 204-1055 of SEQ ID NO:2 and two zinc finger-acidic domain structure (ZAS) DNA binding domains, and wherein said polypeptide modulates immune cell proliferation, TNF-α induced apoptosis, and signaling via an NFKB or INK signaling pathway;
   b) providing a TRAF or c-Jun polypeptide;
   c) contacting the indicator composition with each member of a library of test compounds;
   d) measuring the ability of the KRC polypeptide to interact with the c-Jun or TRAF polypeptide;
   e) determining the ability of the test compound to modulate the interaction of the KRC polypeptide with the c-Jun polypeptide or of the KRC polypeptide with the TRAF polypeptide; and
   f) selecting from the library of test compounds a compound of interest that modulates the ability of the KRC polypeptide to interact with the c-Jun or TRAF polypeptide as compared to a control lacking KRC, to thereby identify a compound that modulates a biological activity of mammalian KRC polypeptide.

3. A method of identifying compounds useful in modulating a biological activity of a mammalian Kappa Recognition Component (KRC) polypeptide comprising:
   a) providing an indicator composition comprising a nucleic acid molecule encoding a KRC polypeptide, wherein the KRC polypeptide is encoded by the nucleic acid molecule comprising the nucleotide sequence of SEQ ID NO:1;
   b) providing a TRAF or c-Jun polypeptide;
   c) contacting the indicator composition with each member of a library of test compounds;

d) measuring the ability of the KRC polypeptide to interact with the c-Jun or TRAF polypeptide;
e) determining the ability of the test compound to modulate the interaction of the KRC polypeptide with the c-Jun polypeptide or of the KRC polypeptide with the TRAF polypeptide; and
f) selecting from the library of test compounds a compound of interest that modulates the ability of the KRC polypeptide to interact with the c-Jun or TRAF polypeptide as compared to an appropriate control, to thereby identify a compound that modulates a biological activity of mammalian KRC polypeptide.

4. A method of identifying compounds useful in modulating a biological activity of a mammalian Kappa Recognition Component (KRC) polypeptide comprising:
a) providing an indicator composition comprising a nucleic acid molecule encoding a KRC polypeptide, wherein the KRC polypeptide is encoded by the nucleic acid molecule comprising the nucleotide sequence of SEQ ID NO:1;
b) providing a TRAF or c-Jun polypeptide;
c) contacting the indicator composition with each member of a library of test compounds;
d) measuring the ability of the KRC polypeptide to interact with the c-Jun or TRAF polypeptide;
e) determining the ability of the test compound to modulate the interaction of the KRC polypeptide with the c-Jun polypeptide or of the KRC polypeptide with the TRAF polypeptide; and
f) selecting from the library of test compounds a compound of interest that modulates the ability of the KRC polypeptide to interact with the c-Jun or TRAF polypeptide as compared to a control lacking KRC, to thereby identify a compound that modulates a biological activity of mammalian KRC polypeptide.

5. A method of identifying compounds useful in modulating a biological activity of a mammalian Kappa Recognition Component (KRC) polypeptide comprising:
a) providing an indicator composition comprising a nucleic acid molecule encoding a KRC polypeptide, wherein the amino acid sequence of the KRC polypeptide comprises SEQ ID NO:2;
b) providing a TRAF or c-Jun polypeptide;
c) contacting the indicator composition with each member of a library of test compounds;
d) measuring the ability of the KRC polypeptide to interact with the c-Jun or TRAF polypeptide;
e) determining the ability of the test compound to modulate the interaction of the KRC polypeptide with the c-Jun polypeptide or of the KRC polypeptide with the TRAF polypeptide; and
f) selecting from the library of test compounds a compound of interest that modulates the ability of the KRC polypeptide to interact with the c-Jun or TRAF polypeptide as compared to an appropriate control, to thereby identify a compound that modulates a biological activity of mammalian KRC polypeptide.

6. A method of identifying compounds useful in modulating a biological activity of a mammalian Kappa Recognition Component (KRC) polypeptide comprising:
a) providing an indicator composition comprising a nucleic acid molecule encoding a KRC polypeptide, wherein the amino acid sequence of the KRC polypeptide comprises SEQ ID NO:2;
b) providing a TRAF or c-Jun polypeptide;
c) contacting the indicator composition with each member of a library of test compounds;
d) measuring the ability of the KRC polypeptide to interact with the c-Jun or TRAF polypeptide;
e) determining the ability of the test compound to modulate the interaction of the KRC polypeptide with the c-Jun polypeptide or of the KRC polypeptide with the TRAF polypeptide; and
f) selecting from the library of test compounds a compound of interest that modulates the ability of the KRC polypeptide to interact with the c-Jun or TRAF polypeptide as compared to a control lacking KRC, to thereby identify a compound that modulates a biological activity of mammalian KRC polypeptide.

7. The method of any one claims 1, 2, 3, 4, 5, and 6, wherein the indicator composition is a cell cultured in vitro that expresses the KRC polypeptide and the TRAF or c-Jun polypeptide.

8. The method of claim 7, further comprising determining the effect of the test compound identified as modulating the ability of the KRC polypeptide to interact with the c-Jun or TRAF polypeptide on a biological activity selected from the group consisting of: cytokine production, T cell proliferation, apoptosis, AP-1 activity, actin polymerization, ubiquitination of AP-1, degradation of c-Jun, degradation of c-Fos, and induction of T cell anergy.

9. The method of claim 8, wherein TNFα cytokine production is determined.

10. The method of claim 8, wherein IL-2 cytokine production is determined.

11. The method of claim 7, wherein determining the ability of the test compound to modulate the interaction of the polypeptides comprises determining the ability of the test compound to modulate the coimmunoprecipitation of the polypeptides.

12. The method of claim 7, wherein said indicator composition further comprises a c-Fos polypeptide.

13. The method of claim 12, wherein the ability of the polypeptides to interact is determined by measuring ubiquitination of AP-1.

14. The method of claim 7, further comprising determining the effect of the test compound identified as modulating the ability of the KRC polypeptide to interact with the c-Jun or TRAF polypeptide on NFkB-dependent transactivation or JNK phosphorylation.

15. The method of claim 7, further comprising determining the effect of the test compound identified as modulating the ability of the KRC polypeptide to interact with the c-Jun or TRAF polypeptide on AP-1 ubiquitination or degradation of c-Fos and/or c-Jun.

16. The method of any one claims 1, 2, 3, 4, 5, and 6, wherein the indicator composition is a cell free composition.

17. The method of any one claims 1, 2, 3, 4, 5, and 6, wherein the ability of the KRC polypeptide and the TRAF or c-Jun polypeptide to interact is determined by measuring the formation of a complex between the polypeptides.

18. The method of claim 17, wherein the formation of a complex between the polypeptides is inhibited.

19. The method of claim 17, wherein the formation of a complex between the polypeptides is stimulated.

20. The method of any one claims 1, 2, 3, 4, 5, and 6, wherein the indicator composition is a cell cultured in vitro that expresses the KRC polypeptide.

21. The method of any one claims 1, 2, 3, 4, 5, and 6, wherein:
the indicator composition is a cell cultured in vitro comprising a c-Jun polypeptide, and a reporter gene responsive to the KRC polypeptide; and the effect of the test compound on the interaction of the polypeptides is determined by evaluating the expression of the reporter gene in the presence and absence of the test compound.

22. The method of claim 21, wherein the cell has been engineered to express the KRC polypeptide by introducing into the cell an expression vector encoding the KRC polypeptide.

23. The method of any one claims 1, 2, 3, 4, 5, and 6, wherein the polypeptide that interacts with the KRC polypeptide is c-Jun.

24. The method of any one claims 1, 2, 3, 4, 5, and 6, wherein the polypeptide that interacts with the KRC polypeptide is TRAF.

25. The method of any one claims 1, 2, 3, 4, 5, and 6, wherein the TRAF polypeptide is selected from the group consisting of: TRAF2, TRAF5, and TRAF6.

26. The method of any one claims 1, 2, 3, 4, 5, and 6, wherein the TRAF polypeptide is TRAF2.

27. The method of any one of claims 1, 2, 3, and 4, wherein the amino acid sequence of the KRC polypeptide comprises SEQ ID NO:2.

28. The method of any one of claims 1, 2, 5, and 6, wherein the KRC polypeptide is encoded by a nucleic acid molecule comprising the nucleotide sequence of SEQ ID NO: 1.

* * * * *

UNITED STATES PATENT AND TRADEMARK OFFICE
CERTIFICATE OF CORRECTION

PATENT NO. : 7,615,380 B2
APPLICATION NO. : 10/701401
DATED : November 10, 2009
INVENTOR(S) : Glimcher et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 254 days Delete the phrase "by 254 days" and insert -- by 746 days --

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,615,380 B2  Page 1 of 1
APPLICATION NO. : 10/701401
DATED : November 10, 2009
INVENTOR(S) : Laurie H. Glimcher et al.

It is certified that error appears in the above-identified patent and that said Letters Patent is hereby corrected as shown below:

At Column 1 line 15, under the government funding heading, please delete the existing paragraph and replace with the following:

"This invention was made with Government support under the National Institutes of Health awards AR46983 and AI29673. The Government has certain rights in the invention."

Signed and Sealed this

Thirty-first Day of August, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 8546
<212> TYPE: DNA
<213> ORGANISM: Homo sapiens
<220> FEATURE:
<221> NAME/KEY: CDS
<222> LOCATION: (889)...(8106)

<400> SEQUENCE: 1
acacctgcgc gccggaataa ttcatgaaga aggggctgga tccgtgggtc agagaacaca      60
ggaccagttt gccatcccaa ggccgaaggc ctccctccaa cacagttctc caagctctag     120
aaatctctga cacatcttga ccatgagacc acggctggtt tttggcagga ttcgaggcac     180
aaacccagca gcctcaacct agttcatgga ggagcctcgc ggggtcctgg ccaagcaagc     240
ccgcccctct ggtgggaaga gcggcgccta ggtggagggt ggctgccgta ggagtggaca     300
tgaatgctgg cttcagaga gaacagcgtt tcagttttgg tcatcggaag tggtgccttc      360
agcacagaag aagagcgtga tttctcctcc aaggccgttg atctccaacc cagaactaaa     420
ggggagaaga gccaccccca gcatccagcg tggcatctct tgtgccagga ccagggatga     480
ctgggccatg gacacagatg tctccaacct tcaaccgttt gcatagcaca cgggggactc     540
gtgggggcca cctgccactg ccagctgaaa taatacaatg gcaatactga catccttcat     600
gacgttttcc cgacagacat tcaggcagaa agtgctggtg cgttttctgt ctgcaaagta     660
gagggccatc gctcaccaat agaatagcgt gggccctgat gacctgctcc gagtccactc     720
acagccagtg acacttgcaa aaaactccca aagccgtctt gggtttggct cccacagctc     780
ttgaccaatg tggccaaagc tggacacctc cttgggacac tgggattatt cataaatgca     840
gcccgccctg actctccctg aatagcatct gaagtctttg tgaaggtc atg gat cct     897
                                                    Met Asp Pro
                                                      1 gaa caa agt gtc aag ggc acc aag aag gct gag gga agt ccc cgg aag     945
Glu Gln Ser Val Lys Gly Thr Lys Lys Ala Glu Gly Ser Pro Arg Lys
  5                  10                  15
```

-continued

```
cgg ctg acc aaa gga gag gcc att cag acc agt gtt tct tcc agc gtc      993
Arg Leu Thr Lys Gly Glu Ala Ile Gln Thr Ser Val Ser Ser Ser Val
 20              25                  30                  35 cca tac cca ggc agc ggc aca gct ccg acc caa gag agc ccc gcc caa     1041
Pro Tyr Pro Gly Ser Gly Thr Ala Pro Thr Gln Glu Ser Pro Ala Gln
                 40                  45                  50 gag ctc tta gcc ccg cag ccc ttc ccg ggc ccc tca tca gtt ctt agg     1089
Glu Leu Leu Ala Pro Gln Pro Phe Pro Gly Pro Ser Ser Val Leu Arg
             55                  60                  65 gaa ggc tct cag gag aaa acg ggc cag cag cag aag ccc ccc aaa agg     1137
Glu Gly Ser Gln Glu Lys Thr Gly Gln Gln Gln Lys Pro Pro Lys Arg
         70                  75                  80 ccc ccc atc gaa gca tcc gtc cac atc tca cac gtt ccg cag cac cct     1185
Pro Pro Ile Glu Ala Ser Val His Ile Ser His Val Pro Gln His Pro
     85                  90                  95 ctg aca cca gca ttc atg tcg cct ggc aaa cct gag cat ctc ctg gag     1233
Leu Thr Pro Ala Phe Met Ser Pro Gly Lys Pro Glu His Leu Leu Glu
100                 105                 110                 115 ggg tcc aca tgg caa ctg gtt agc ccc atg aga ctc gga ccc tct ggc     1281
Gly Ser Thr Trp Gln Leu Val Ser Pro Met Arg Leu Gly Pro Ser Gly
                 120                 125                 130 tcc ttg ctg gcc cct ggg ctc cat cct cag agc cag ctc ctt cct tcc     1329
Ser Leu Leu Ala Pro Gly Leu His Pro Gln Ser Gln Leu Leu Pro Ser
             135                 140                 145 cac gct tcc atc att ccc ccc gag gac ctt cct gga gtc ccc aaa gtc     1377
His Ala Ser Ile Ile Pro Pro Glu Asp Leu Pro Gly Val Pro Lys Val
         150                 155                 160 ttc gtg cct cgt cct tcc cag gtc tcc ttg aag ccc aca gaa gag gca     1425
Phe Val Pro Arg Pro Ser Gln Val Ser Leu Lys Pro Thr Glu Glu Ala
165                 170                 175 cac aag aag gag agg aag ccc cag aag cca ggc aag tac atc tgc cag     1473
His Lys Lys Glu Arg Lys Pro Gln Lys Pro Gly Lys Tyr Ile Cys Gln
180                 185                 190                 195 tac tgc agc cgg ccc tgt gcc aag ccc agc gtg ctc cag aag cac att     1521
Tyr Cys Ser Arg Pro Cys Ala Lys Pro Ser Val Leu Gln Lys His Ile
                 200                 205                 210 cgc tca cac aca ggt gag agg ccc tac ccc tgc ggc ccc tgt ggc ttc     1569
Arg Ser His Thr Gly Glu Arg Pro Tyr Pro Cys Gly Pro Cys Gly Phe
             215                 220                 225 tcc ttc aag acc aag agt aat ctc tac aag cac agg aag tcc cat gcc     1617
Ser Phe Lys Thr Lys Ser Asn Leu Tyr Lys His Arg Lys Ser His Ala
         230                 235                 240 cac cgc atc aaa gca ggc ctg gcc tca ggc atg ggt ggc gag atg tac     1665
His Arg Ile Lys Ala Gly Leu Ala Ser Gly Met Gly Gly Glu Met Tyr
245                 250                 255 cca cat ggg ctg gag atg gag cgg atc cct ggg gaa gag ttt gag gag     1713
Pro His Gly Leu Glu Met Glu Arg Ile Pro Gly Glu Glu Phe Glu Glu
260                 265                 270                 275 ccc act gag gga gaa agc aca gat tct gaa gag gag act agt gcc acc     1761
Pro Thr Glu Gly Glu Ser Thr Asp Ser Glu Glu Glu Thr Ser Ala Thr
                 280                 285                 290 tct ggt cac cct gca gag ctc tcc cca aga ccc aag cag ccc ctt ctc     1809
Ser Gly His Pro Ala Glu Leu Ser Pro Arg Pro Lys Gln Pro Leu Leu
             295                 300                 305 tcc agc ggg cta tac agc tct ggg agc cac agt tcc agc cac gaa cgc     1857
Ser Ser Gly Leu Tyr Ser Ser Gly Ser His Ser Ser Ser His Glu Arg
         310                 315                 320 tgt tcc ctg tcc cag tcc agc aca gcc cag tca ctc gaa gac ccc cct     1905
Cys Ser Leu Ser Gln Ser Ser Thr Ala Gln Ser Leu Glu Asp Pro Pro
```

-continued

```
                325                 330                 335
cca ttt gtg gaa ccc tca tct gag cac ccc ctg agc cat aaa cct gaa    1953
Pro Phe Val Glu Pro Ser Ser Glu His Pro Leu Ser His Lys Pro Glu
340                 345                 350                 355 gac acc cac acg att aag cag aag ctg gcc ctc cgc tta agc gag agg    2001
Asp Thr His Thr Ile Lys Gln Lys Leu Ala Leu Arg Leu Ser Glu Arg
                360                 365                 370 aag aag gtg atc gat gag cag gcg ttt ctg agc cca ggc agc aaa ggg    2049
Lys Lys Val Ile Asp Glu Gln Ala Phe Leu Ser Pro Gly Ser Lys Gly
            375                 380                 385 agt act gag tct ggg tat ttc tct cgc tcc gag agt gca gag cag cag    2097
Ser Thr Glu Ser Gly Tyr Phe Ser Arg Ser Glu Ser Ala Glu Gln Gln
        390                 395                 400 gtc agc ccc cca aac acc aac gcc aag tcc tac gct gag atc atc ttt    2145
Val Ser Pro Pro Asn Thr Asn Ala Lys Ser Tyr Ala Glu Ile Ile Phe
    405                 410                 415 ggc aag tgt ggg cga ata gga cag cgg acc gcc atg ctg aca gcc acc    2193
Gly Lys Cys Gly Arg Ile Gly Gln Arg Thr Ala Met Leu Thr Ala Thr
420                 425                 430                 435 tcc acc cag ccc ctc ctg ccc ctc tcc acc gaa gac aag ccc agc ctg    2241
Ser Thr Gln Pro Leu Leu Pro Leu Ser Thr Glu Asp Lys Pro Ser Leu
                440                 445                 450 gtg cct ttg tct gta ccc cgg acg cag gtg atc gag cac atc acg aag    2289
Val Pro Leu Ser Val Pro Arg Thr Gln Val Ile Glu His Ile Thr Lys
            455                 460                 465 ctc atc acc atc aac gag gcc gtg gtg gac acc agt gag atc gac agc    2337
Leu Ile Thr Ile Asn Glu Ala Val Val Asp Thr Ser Glu Ile Asp Ser
        470                 475                 480 gtg aag cca agg cgg agc tca ctg tcc agg cgc agc agc atg gag tcc    2385
Val Lys Pro Arg Arg Ser Ser Leu Ser Arg Arg Ser Ser Met Glu Ser
    485                 490                 495 cca aaa tcc agc ctc tac cgg gag ccc ctg tca tcc cac agt gag aaa    2433
Pro Lys Ser Ser Leu Tyr Arg Glu Pro Leu Ser Ser His Ser Glu Lys
500                 505                 510                 515 acc aag cct gaa caa tca ctg ctg agc ctc cag cac ccg ccc agt acc    2481
Thr Lys Pro Glu Gln Ser Leu Leu Ser Leu Gln His Pro Pro Ser Thr
                520                 525                 530 gcc ccc cct gtg cct ctc ctg aga agc cac tca atg cct tct gcc gcc    2529
Ala Pro Pro Val Pro Leu Leu Arg Ser His Ser Met Pro Ser Ala Ala
            535                 540                 545 tgc act atc agc acc ccc cac cac ccc ttc cga ggt agc tac tcc ttc    2577
Cys Thr Ile Ser Thr Pro His His Pro Phe Arg Gly Ser Tyr Ser Phe
        550                 555                 560 gat gac cat atc acc gac tcc gaa gcc ctg agc cgc agc agt cac gtg    2625
Asp Asp His Ile Thr Asp Ser Glu Ala Leu Ser Arg Ser Ser His Val
    565                 570                 575 ttt acc tcc cac ccc cgg atg ctg aag ccg cag ccg gca atc gaa tta    2673
Phe Thr Ser His Pro Arg Met Leu Lys Pro Gln Pro Ala Ile Glu Leu
580                 585                 590                 595 cct ttg gga ggg gaa tac agt tct gag gag cct ggc cca agc agc aaa    2721
Pro Leu Gly Gly Glu Tyr Ser Ser Glu Glu Pro Gly Pro Ser Ser Lys
                600                 605                 610 gac aca gcc tcc aag ccc tcg gac gaa gtg gaa ccc aag gaa agc gag    2769
Asp Thr Ala Ser Lys Pro Ser Asp Glu Val Glu Pro Lys Glu Ser Glu
            615                 620                 625 ctt acc aaa aag acc aag aag ggt ttg aaa aca aaa ggg gtg atc tac    2817
Leu Thr Lys Lys Thr Lys Lys Gly Leu Lys Thr Lys Gly Val Ile Tyr
        630                 635                 640 gaa tgt aac ata tgt ggt gct cgg tac aag aaa agg gat aac tac gaa    2865
```

```
                Glu Cys Asn Ile Cys Gly Ala Arg Tyr Lys Lys Arg Asp Asn Tyr Glu
                    645                 650                 655 gcc cac aaa aaa tac tac tgc tca gag ctt cag atc gca aag ccc atc                    2913
Ala His Lys Lys Tyr Tyr Cys Ser Glu Leu Gln Ile Ala Lys Pro Ile
660                 665                 670                 675 tct gca ggc acc cac aca tct cca gaa gct gaa aag agt cag att gag                    2961
Ser Ala Gly Thr His Thr Ser Pro Glu Ala Glu Lys Ser Gln Ile Glu
                680                 685                 690 cat gag ccg tgg tcc caa atg atg cat tac aaa ctg gga acc acc ctg                    3009
His Glu Pro Trp Ser Gln Met Met His Tyr Lys Leu Gly Thr Thr Leu
            695                 700                 705 gaa ctc act cca ctg agg aag agg agg aaa gag aag agc ctt ggg gac                    3057
Glu Leu Thr Pro Leu Arg Lys Arg Arg Lys Glu Lys Ser Leu Gly Asp
        710                 715                 720 gag gaa gag cca cct gcc ttt gag tcc aca aaa agt cag ttt ggc agc                    3105
Glu Glu Glu Pro Pro Ala Phe Glu Ser Thr Lys Ser Gln Phe Gly Ser
    725                 730                 735 ccc ggg cca tct gat gct gct cgg aac ctt ccc ctg gag tcc acc aag                    3153
Pro Gly Pro Ser Asp Ala Ala Arg Asn Leu Pro Leu Glu Ser Thr Lys
740                 745                 750                 755 tca cca gca gaa cca agt aaa tca gtg ccc tcc ttg gag gga ccc acg                    3201
Ser Pro Ala Glu Pro Ser Lys Ser Val Pro Ser Leu Glu Gly Pro Thr
                760                 765                 770 ggc ttc cag cca agg act ccc aag cca ggg tcc ggt tca gaa tca ggg                    3249
Gly Phe Gln Pro Arg Thr Pro Lys Pro Gly Ser Gly Ser Glu Ser Gly
            775                 780                 785 aag gag agg aga aca acg tcc aaa gaa att tct gtc atc cag cac acc                    3297
Lys Glu Arg Arg Thr Thr Ser Lys Glu Ile Ser Val Ile Gln His Thr
        790                 795                 800 agc tcc ttt gag aaa tct gat tct ctc gag cag ccg agt ggc ttg gaa                    3345
Ser Ser Phe Glu Lys Ser Asp Ser Leu Glu Gln Pro Ser Gly Leu Glu
    805                 810                 815 ggg gaa gac aaa cct ctg gcc cag ttc cca tca ccc cca cct gcc cca                    3393
Gly Glu Asp Lys Pro Leu Ala Gln Phe Pro Ser Pro Pro Pro Ala Pro
820                 825                 830                 835 cac gga cgc tct gct cac tcc ctg cag cct aag ttg gtc cgc cag ccc                    3441
His Gly Arg Ser Ala His Ser Leu Gln Pro Lys Leu Val Arg Gln Pro
                840                 845                 850 aac att cag gtt cct gag atc cta gta act gag gag cct gac cgg ccg                    3489
Asn Ile Gln Val Pro Glu Ile Leu Val Thr Glu Glu Pro Asp Arg Pro
            855                 860                 865 gac aca gag cca gag ccg ccc cct aag gaa cct gag aag act gag gag                    3537
Asp Thr Glu Pro Glu Pro Pro Pro Lys Glu Pro Glu Lys Thr Glu Glu
        870                 875                 880 ttc caa tgg ccc cag cgc agc cag aca ctt gcc cag ctc cca gct gag                    3585
Phe Gln Trp Pro Gln Arg Ser Gln Thr Leu Ala Gln Leu Pro Ala Glu
    885                 890                 895 aag gct cca ccc aaa aag aag agg ttg cgc ctg gca gag atg gcc caa                    3633
Lys Ala Pro Pro Lys Lys Lys Arg Leu Arg Leu Ala Glu Met Ala Gln
900                 905                 910                 915 tca tca ggg gag tcc agc ttc gag tcc tct gtg cct ctg tct cgc agc                    3681
Ser Ser Gly Glu Ser Ser Phe Glu Ser Ser Val Pro Leu Ser Arg Ser
                920                 925                 930 ccg agc cag gaa agc aat gtc tct ttg agt ggg tcc agc cgc tca gcc                    3729
Pro Ser Gln Glu Ser Asn Val Ser Leu Ser Gly Ser Ser Arg Ser Ala
            935                 940                 945 tcg ttt gag agg gat gac cat ggg aaa gcc gag gcc ccc gat ccc tca                    3777
Ser Phe Glu Arg Asp Asp His Gly Lys Ala Glu Ala Pro Asp Pro Ser
        950                 955                 960
```

```
tct gac atg cgc ccc aaa ccc ctg ggc acc cac atg ttg act gtc ccc    3825
Ser Asp Met Arg Pro Lys Pro Leu Gly Thr His Met Leu Thr Val Pro
965             970                 975 agc cac cac cca cat gcc cga gag atg cgg agg tca gcc tca gag cag    3873
Ser His His Pro His Ala Arg Glu Met Arg Arg Ser Ala Ser Glu Gln
    980             985                 990                 995 agc ccc aac gtt tcc cat tct gcc cac atg acc gag aca cgc agc aaa    3921
Ser Pro Asn Val Ser His Ser Ala His Met Thr Glu Thr Arg Ser Lys
                1000                1005                1010 tcc ttt gac tat ggc agc ttg tcc ttg aca ggc cct tct gct cca gcc    3969
Ser Phe Asp Tyr Gly Ser Leu Ser Leu Thr Gly Pro Ser Ala Pro Ala
            1015                1020                1025 cca gtg gct cca cca gcc ggg gag gcc ccg cca gag aga aga aaa tgc    4017
Pro Val Ala Pro Pro Ala Gly Glu Ala Pro Pro Glu Arg Arg Lys Cys
        1030                1035                1040 ttc ttg gtg aga agc ccc tct ctg agc agg cct cca gaa tct gag ttg    4065
Phe Leu Val Arg Ser Pro Ser Leu Ser Arg Pro Pro Glu Ser Glu Leu
    1045                1050                1055 gag gtt gcc ccc aag gga aga cag gag agc gaa gaa cca cag ccc tca    4113
Glu Val Ala Pro Lys Gly Arg Gln Glu Ser Glu Glu Pro Gln Pro Ser
1060                1065                1070                1075 tcc agt aaa ccc tct gcc aaa agc tca ttg tcc cag att tcc tct gcg    4161
Ser Ser Lys Pro Ser Ala Lys Ser Ser Leu Ser Gln Ile Ser Ser Ala
                1080                1085                1090 gcc acc tca cat ggt gga ccc ccg gga ggc aag ggc cca ggg cag gac    4209
Ala Thr Ser His Gly Gly Pro Pro Gly Gly Lys Gly Pro Gly Gln Asp
            1095                1100                1105 agg ccc gca ttg ggg ccc act gtg ccc tac aca gaa gca ctg caa gtg    4257
Arg Pro Ala Leu Gly Pro Thr Val Pro Tyr Thr Glu Ala Leu Gln Val
        1110                1115                1120 ttc cac cac ccc gtt gcc cag aca ccc ctg cat gag aag cca tac ctg    4305
Phe His His Pro Val Ala Gln Thr Pro Leu His Glu Lys Pro Tyr Leu
    1125                1130                1135 ccc cca cca gtc tcc ctt ttc tcc ttc cag cat ctc gtg cag cat gag    4353
Pro Pro Pro Val Ser Leu Phe Ser Phe Gln His Leu Val Gln His Glu
1140                1145                1150                1155 cca gga cag tct cca gaa ttc ttc tcc acc cag gcc atg tcc agc ctc    4401
Pro Gly Gln Ser Pro Glu Phe Phe Ser Thr Gln Ala Met Ser Ser Leu
                1160                1165                1170 ctg tcc tca cca tac tcc atg ccc cca ctt cct ccc tcc tta ttt caa    4449
Leu Ser Ser Pro Tyr Ser Met Pro Pro Leu Pro Pro Ser Leu Phe Gln
            1175                1180                1185 gcc cca ccg ctt cct ctc cag cct act gtt ctg cac cca ggc caa ctc    4497
Ala Pro Pro Leu Pro Leu Gln Pro Thr Val Leu His Pro Gly Gln Leu
        1190                1195                1200 cat ctc ccc cag ctc atg cct cac cca gcc aac atc ccc ttc agg caa    4545
His Leu Pro Gln Leu Met Pro His Pro Ala Asn Ile Pro Phe Arg Gln
    1205                1210                1215 ccc cct tcc ttc ctc ccc atg cca tac ccg acc tcc tca gca ctg tct    4593
Pro Pro Ser Phe Leu Pro Met Pro Tyr Pro Thr Ser Ser Ala Leu Ser
1220                1225                1230                1235 tct ggg ttt ttc ctg cct ctg caa tcc cag ttt gca ctt cag ctc cct    4641
Ser Gly Phe Phe Leu Pro Leu Gln Ser Gln Phe Ala Leu Gln Leu Pro
                1240                1245                1250 ggt gat gtg gaa agc cat ctg ccc cag atc aaa acc agc ctg gcc cca    4689
Gly Asp Val Glu Ser His Leu Pro Gln Ile Lys Thr Ser Leu Ala Pro
            1255                1260                1265 ctg gca aca gga agt gct ggc ctc tcc ccc agc caa gag tac agc agt    4737
Leu Ala Thr Gly Ser Ala Gly Leu Ser Pro Ser Gln Glu Tyr Ser Ser
        1270                1275                1280
```

```
gac atc cgg cta ccc cct gtg gct ccc cca gcc agc tcc tca gca cct      4785
Asp Ile Arg Leu Pro Pro Val Ala Pro Pro Ala Ser Ser Ser Ala Pro
    1285                1290                1295 aca tca gct cct cca ctg gcc ctg cct gcc tgt cca gac acc atg gtg      4833
Thr Ser Ala Pro Pro Leu Ala Leu Pro Ala Cys Pro Asp Thr Met Val
1300                1305                1310                1315 tcc ctg gtt gtg cct gtc cgt gtt cag acc aat atg ccg tcc tat ggg      4881
Ser Leu Val Val Pro Val Arg Val Gln Thr Asn Met Pro Ser Tyr Gly
                1320                1325                1330 agc gca atg tac acc acc ctt tcc cag atc ttg gtc acc cag tcc caa      4929
Ser Ala Met Tyr Thr Thr Leu Ser Gln Ile Leu Val Thr Gln Ser Gln
            1335                1340                1345 ggc agc tca gca act gtg gca ctt ccc aag ttt gag gaa ccc cca tca      4977
Gly Ser Ser Ala Thr Val Ala Leu Pro Lys Phe Glu Glu Pro Pro Ser
        1350                1355                1360 aag ggg acg act gta tgt ggt gca gat gtg cat gag gtt ggg ccc ggc      5025
Lys Gly Thr Thr Val Cys Gly Ala Asp Val His Glu Val Gly Pro Gly
    1365                1370                1375 cct tct ggg tta agt gaa gag caa agc aga gct ttc cca act cca tac      5073
Pro Ser Gly Leu Ser Glu Glu Gln Ser Arg Ala Phe Pro Thr Pro Tyr
1380                1385                1390                1395 ctg aga gtg cct gtg aca tta cct gaa aga aaa ggc act tcc ctg tca      5121
Leu Arg Val Pro Val Thr Leu Pro Glu Arg Lys Gly Thr Ser Leu Ser
                1400                1405                1410 tca gag agt atc ttg agc ctg gag ggg agt tca tca aca gca ggg gga      5169
Ser Glu Ser Ile Leu Ser Leu Glu Gly Ser Ser Ser Thr Ala Gly Gly
            1415                1420                1425 agc aaa cgt gtc ctt tca cca gct ggc agc ctt gaa ctt acc atg gaa      5217
Ser Lys Arg Val Leu Ser Pro Ala Gly Ser Leu Glu Leu Thr Met Glu
        1430                1435                1440 acc cag cag caa aaa aga gtg aag gag gag gag gct tcc aag gca gat      5265
Thr Gln Gln Gln Lys Arg Val Lys Glu Glu Glu Ala Ser Lys Ala Asp
    1445                1450                1455 gaa aaa ctt gag ctg gta aaa cca tgc agt gtg gtc ctt acc agc acc      5313
Glu Lys Leu Glu Leu Val Lys Pro Cys Ser Val Val Leu Thr Ser Thr
1460                1465                1470                1475 gag gat ggg aag agg cca gag aaa tcc cac tta ggc aac cag ggc caa      5361
Glu Asp Gly Lys Arg Pro Glu Lys Ser His Leu Gly Asn Gln Gly Gln
                1480                1485                1490 ggc agg agg gag cta gaa atg ctg tcc agc ctg tcc tca gat cca tct      5409
Gly Arg Arg Glu Leu Glu Met Leu Ser Ser Leu Ser Ser Asp Pro Ser
            1495                1500                1505 gac aca aag gaa att cct ccc ctc cct cac cct gca ttg tcc cat ggg      5457
Asp Thr Lys Glu Ile Pro Pro Leu Pro His Pro Ala Leu Ser His Gly
        1510                1515                1520 caa gcc cca ggc tca gaa gct ttg aag gaa tat ccc cag cca tct ggc      5505
Gln Ala Pro Gly Ser Glu Ala Leu Lys Glu Tyr Pro Gln Pro Ser Gly
    1525                1530                1535 aaa cct cac cga aga ggg ttg acc cca ctg agc gtg aag aaa gaa gat      5553
Lys Pro His Arg Arg Gly Leu Thr Pro Leu Ser Val Lys Lys Glu Asp
1540                1545                1550                1555 tcc aag gaa caa cct gat ctc ccc tcc ttg gca cct ccg agc tct ctg      5601
Ser Lys Glu Gln Pro Asp Leu Pro Ser Leu Ala Pro Pro Ser Ser Leu
                1560                1565                1570 cct ctg tca gaa acg tcc tcc aga cca gcc aag tca caa gaa ggt acg      5649
Pro Leu Ser Glu Thr Ser Ser Arg Pro Ala Lys Ser Gln Glu Gly Thr
            1575                1580                1585 gac tca aag aag gta ctg cag ttc ccc agc ctc cac aca acc act aat      5697
Asp Ser Lys Lys Val Leu Gln Phe Pro Ser Leu His Thr Thr Thr Asn
```

-continued

```
             1590                1595                1600
gtc agt tgg tgc tat tta aac tac att aag cca aat cac atc cag cat      5745
Val Ser Trp Cys Tyr Leu Asn Tyr Ile Lys Pro Asn His Ile Gln His
    1605                1610                1615 gca gat agg agg tcc tct gtt tac gct ggt tgg tgc ata agt ttg tac      5793
Ala Asp Arg Arg Ser Ser Val Tyr Ala Gly Trp Cys Ile Ser Leu Tyr
1620                1625                1630                1635 aac ccc aac ctt ccg ggg gtt tcc act aaa gct gct ttg tcc ctc ctg      5841
Asn Pro Asn Leu Pro Gly Val Ser Thr Lys Ala Ala Leu Ser Leu Leu
                1640                1645                1650 agg tct aag cag aaa gtg agc aaa gag aca tac acc atg gcc aca gct      5889
Arg Ser Lys Gln Lys Val Ser Lys Glu Thr Tyr Thr Met Ala Thr Ala
        1655                1660                1665 ccg cat cct gag gca gga agg ctt gtg cca tcc agc tcc cgc aag ccc      5937
Pro His Pro Glu Ala Gly Arg Leu Val Pro Ser Ser Ser Arg Lys Pro
    1670                1675                1680 cgc atg aca gag gtt cac ctc cct tca ctg gtt tcc ccg gaa ggc cag      5985
Arg Met Thr Glu Val His Leu Pro Ser Leu Val Ser Pro Glu Gly Gln
1685                1690                1695 aaa gat cta gct aga gtg gag aag gaa gaa gag agg aga ggg gag ccg      6033
Lys Asp Leu Ala Arg Val Glu Lys Glu Glu Glu Arg Arg Gly Glu Pro
1700                1705                1710                1715 gag gag gat gct cct gcc tcc cag aga ggg gag ccg gcg agg atc aaa      6081
Glu Glu Asp Ala Pro Ala Ser Gln Arg Gly Glu Pro Ala Arg Ile Lys
                1720                1725                1730 atc ttc gaa gga ggg tac aaa tca aac gaa gag tat gta tat gtg cga      6129
Ile Phe Glu Gly Gly Tyr Lys Ser Asn Glu Glu Tyr Val Tyr Val Arg
        1735                1740                1745 ggc cgc ggc cga ggg aaa tat gtt tgt gag gag tgt gga att cgc tgc      6177
Gly Arg Gly Arg Gly Lys Tyr Val Cys Glu Glu Cys Gly Ile Arg Cys
    1750                1755                1760 aag aag ccc agc atg ctg aag aaa cac atc cgc acc cac act gac gtc      6225
Lys Lys Pro Ser Met Leu Lys Lys His Ile Arg Thr His Thr Asp Val
1765                1770                1775 cgg ccc tat gtg tgc aag cac tgt cac ttt gct ttt aaa acc aaa ggg      6273
Arg Pro Tyr Val Cys Lys His Cys His Phe Ala Phe Lys Thr Lys Gly
1780                1785                1790                1795 aat ctg act aag cac atg aag tcg aag gcc cac agc aaa aag tgc caa      6321
Asn Leu Thr Lys His Met Lys Ser Lys Ala His Ser Lys Lys Cys Gln
                1800                1805                1810 gag aca ggg gtg ctg gag gag ctg gaa gcc gaa gaa gga acc agt gac      6369
Glu Thr Gly Val Leu Glu Glu Leu Glu Ala Glu Glu Gly Thr Ser Asp
        1815                1820                1825 gac ctg ttc cag gac tcg gaa gga cga gag ggt tca gag gct gtg gag      6417
Asp Leu Phe Gln Asp Ser Glu Gly Arg Glu Gly Ser Glu Ala Val Glu
    1830                1835                1840 gag cac cag ttt tcg gac ctg gag gac tcg gac tca gac tca gac ctg      6465
Glu His Gln Phe Ser Asp Leu Glu Asp Ser Asp Ser Asp Ser Asp Leu
1845                1850                1855 gac gaa gac gag gat gag gat gag gag gag agc cag gat gag ctg tcc      6513
Asp Glu Asp Glu Asp Glu Asp Glu Glu Glu Ser Gln Asp Glu Leu Ser
1860                1865                1870                1875 aga cca tcc tca gag gcg ccc ccg cct ggc cca cca cat gca ctg cgg      6561
Arg Pro Ser Ser Glu Ala Pro Pro Pro Gly Pro Pro His Ala Leu Arg
                1880                1885                1890 gca gac tcc tca ccc atc ctg ggc cct cag ccc cca gat gcc ccc gcc      6609
Ala Asp Ser Ser Pro Ile Leu Gly Pro Gln Pro Pro Asp Ala Pro Ala
        1895                1900                1905 tct ggc acg gag gcc aca cga ggc agc tcg gtc tcg gaa gct gag cgc      6657
```

-continued

```
Ser Gly Thr Glu Ala Thr Arg Gly Ser Ser Val Ser Glu Ala Glu Arg
        1910                1915                1920 ctg aca gcc agc agc tgc tcc atg tcc agc cag agc atg ccg ggc ctc         6705
Leu Thr Ala Ser Ser Cys Ser Met Ser Ser Gln Ser Met Pro Gly Leu
    1925                1930                1935 ccc tgg ctg gga ccg gcc cct ctg ggc tct gtg gag aaa gac aca ggc         6753
Pro Trp Leu Gly Pro Ala Pro Leu Gly Ser Val Glu Lys Asp Thr Gly
1940                1945                1950                1955 tca gcc ttg agc tac aag cct gtc cca aga aga ccg tgg tcc cca             6801
Ser Ala Leu Ser Tyr Lys Pro Val Ser Pro Arg Arg Pro Trp Ser Pro
                1960                1965                1970 agc aaa gaa gca ggc agc cgt cca cca cta gcc cgc aaa cac tcg cta         6849
Ser Lys Glu Ala Gly Ser Arg Pro Pro Leu Ala Arg Lys His Ser Leu
        1975                1980                1985 acc aaa aac gac tca tct ccc cag cga tgc tcc ccg gcc cga gaa cca         6897
Thr Lys Asn Asp Ser Ser Pro Gln Arg Cys Ser Pro Ala Arg Glu Pro
    1990                1995                2000 cag gcc tca gcc cca agc cca cct ggc ctg cac gtg gac cca gga agg         6945
Gln Ala Ser Ala Pro Ser Pro Pro Gly Leu His Val Asp Pro Gly Arg
    2005                2010                2015 ggc atg ggc cct ctc cct tgt ggg tct cca aga ctt cag ctg tct cct         6993
Gly Met Gly Pro Leu Pro Cys Gly Ser Pro Arg Leu Gln Leu Ser Pro
2020                2025                2030                2035 ctc acc ctc tgc ccc ctg gga aga gaa ctg gcc cct cga gca cat gtg         7041
Leu Thr Leu Cys Pro Leu Gly Arg Glu Leu Ala Pro Arg Ala His Val
                2040                2045                2050 ctc tcc aaa ctc gag ggt acc acc gac cca ggc ctc ccc aga tac tcg         7089
Leu Ser Lys Leu Glu Gly Thr Thr Asp Pro Gly Leu Pro Arg Tyr Ser
        2055                2060                2065 ccc acc agg aga tgg tct cca ggt cag gcc gag tca cca cca cgg tca         7137
Pro Thr Arg Arg Trp Ser Pro Gly Gln Ala Glu Ser Pro Pro Arg Ser
    2070                2075                2080 gcg ccg cca ggg aag tgg gcc ttg gct ggg ccg ggc agc ccc tca gcg         7185
Ala Pro Pro Gly Lys Trp Ala Leu Ala Gly Pro Gly Ser Pro Ser Ala
    2085                2090                2095 ggg gag cat ggc cca ggc ttg ggg ctg gcc cca cgg gtt ctc ttc ccg         7233
Gly Glu His Gly Pro Gly Leu Gly Leu Ala Pro Arg Val Leu Phe Pro
2100                2105                2110                2115 ccc gcg cct cta cct cac aag ctc ctc agc aga agc cca gag acc tgc         7281
Pro Ala Pro Leu Pro His Lys Leu Leu Ser Arg Ser Pro Glu Thr Cys
                2120                2125                2130 gcc tcc ccg tgg cag aag gcc gag tcc cga agt ccc tcc tgc tca ccc         7329
Ala Ser Pro Trp Gln Lys Ala Glu Ser Arg Ser Pro Ser Cys Ser Pro
        2135                2140                2145 ggc cct gct cat cct ctc tcc tcc cga ccc ttc tcc gcc ctc cat gac         7377
Gly Pro Ala His Pro Leu Ser Ser Arg Pro Phe Ser Ala Leu His Asp
    2150                2155                2160 ttc cac ggc cac atc ctg gcc cgg aca gag gag aac atc ttc agc cac         7425
Phe His Gly His Ile Leu Ala Arg Thr Glu Glu Asn Ile Phe Ser His
    2165                2170                2175 ctg cct ctg cac tcc cag cac ttg acc cgt gcc cca tgt ccc ttg att         7473
Leu Pro Leu His Ser Gln His Leu Thr Arg Ala Pro Cys Pro Leu Ile
2180                2185                2190                2195 ccc atc ggt ggg atc cag atg gtg cag gcc cgg cca gga gcc cac ccc         7521
Pro Ile Gly Gly Ile Gln Met Val Gln Ala Arg Pro Gly Ala His Pro
                2200                2205                2210 acc ctg ctg cca ggg ccc acc gca gcc tgg gtc agt ggc ttc tcc ggg         7569
Thr Leu Leu Pro Gly Pro Thr Ala Ala Trp Val Ser Gly Phe Ser Gly
        2215                2220                2225
```

```
ggt ggc agc gac ctg aca ggg gcc cgg gag gcc cag gag cga ggc cgc     7617
Gly Gly Ser Asp Leu Thr Gly Ala Arg Glu Ala Gln Glu Arg Gly Arg
        2230                2235                2240 tgg agt ccc act gag agc tcg tca gcc tcc gtg tcg cct gtg gct aag     7665
Trp Ser Pro Thr Glu Ser Ser Ser Ala Ser Val Ser Pro Val Ala Lys
        2245                2250                2255 gtc tcc aaa ttc aca ctc tcc tca gag ctg gag ggc agg gac tac ccc     7713
Val Ser Lys Phe Thr Leu Ser Ser Glu Leu Glu Gly Arg Asp Tyr Pro
2260                2265                2270                2275 aag gag agg gag agg acc ggc gga ggc ccg ggc agg cct cct gac tgg     7761
Lys Glu Arg Glu Arg Thr Gly Gly Gly Pro Gly Arg Pro Pro Asp Trp
                2280                2285                2290 aca ccc cat ggg acc ggg gca cct gca gag ccc aca ccc acg cac agc     7809
Thr Pro His Gly Thr Gly Ala Pro Ala Glu Pro Thr Pro Thr His Ser
        2295                2300                2305 ccc tgc acc cca ccc gac acc ttg ccc cgg ccg ccc cag gga cgc cgg     7857
Pro Cys Thr Pro Pro Asp Thr Leu Pro Arg Pro Pro Gln Gly Arg Arg
        2310                2315                2320 gca gcg cag tcc tgg agc ccc cgc ttg gag tcc ccg cgt gca ccg gcc     7905
Ala Ala Gln Ser Trp Ser Pro Arg Leu Glu Ser Pro Arg Ala Pro Ala
        2325                2330                2335 aac ccc gag cct tct gcc acc ccg ccg ctg gac cgc agc agc tct gtg     7953
Asn Pro Glu Pro Ser Ala Thr Pro Pro Leu Asp Arg Ser Ser Ser Val
2340                2345                2350                2355 ggc tgc ctg gca gag gcc tct gcc cgc ttc cca gcc cgg acg agg aac     8001
Gly Cys Leu Ala Glu Ala Ser Ala Arg Phe Pro Ala Arg Thr Arg Asn
                2360                2365                2370 ctc tcc ggg gaa tcc agg acc agg cag gac tcc ccc aag ccc tca gga     8049
Leu Ser Gly Glu Ser Arg Thr Arg Gln Asp Ser Pro Lys Pro Ser Gly
        2375                2380                2385 agt ggg gag ccc agg gca cat cca cat cag cct gag gac agg gtt ccc     8097
Ser Gly Glu Pro Arg Ala His Pro His Gln Pro Glu Asp Arg Val Pro
        2390                2395                2400 ccc aac gct tagcctctct ccaactgctt cagcatctgg cttccagtgt             8146
Pro Asn Ala
    2405 ccagcaacag acgtttccag ccactttcct cgaatcatcc cacttcctca gccccatctg   8206 tccctccatc caggagctct cacggcccca tctgttgtac cttcccatgt atgcagttac   8266 ctgtgccttt ttctacacct tttgttgctt aaaaagaaac aaaacaaatc acatacatac   8326 atttaaaaaa aaaacaacaa cccacgagga gtctgaggct gtgaatagtt tatggttttg   8386 gggaaaggct gatggtgaag cctcctgacc ctccccgctg tggttggcag ccacccaccc   8446 cagaggctgg cagagggaaa ggggtacact gagggagaaa ggaaaaggaa acttcaaaca   8506 atatagaatt aaatgtaaaa ggcagcactc ctgtgtacag                        8546

<210> SEQ ID NO 2
<211> LENGTH: 2406
<212> TYPE: PRT
<213> ORGANISM: Homo sapiens

<400> SEQUENCE: 2

Met Asp Pro Glu Gln Ser Val Lys Gly Thr Lys Lys Ala Glu Gly Ser
1               5                   10                  15

Pro Arg Lys Arg Leu Thr Lys Gly Glu Ala Ile Gln Thr Ser Val Ser
            20                  25                  30

Ser Ser Val Pro Tyr Pro Gly Ser Gly Thr Ala Pro Thr Gln Glu Ser
        35                  40                  45
```

-continued

```
Pro Ala Gln Glu Leu Leu Ala Pro Gln Pro Phe Pro Gly Pro Ser Ser
    50                  55                  60

Val Leu Arg Glu Gly Ser Gln Glu Lys Thr Gly Gln Gln Lys Pro
65                  70                  75                  80

Pro Lys Arg Pro Pro Ile Glu Ala Ser Val His Ile Ser His Val Pro
                85                  90                  95

Gln His Pro Leu Thr Pro Ala Phe Met Ser Pro Gly Lys Pro Glu His
            100                 105                 110

Leu Leu Glu Gly Ser Thr Trp Gln Leu Val Ser Pro Met Arg Leu Gly
        115                 120                 125

Pro Ser Gly Ser Leu Leu Ala Pro Gly Leu His Pro Gln Ser Gln Leu
    130                 135                 140

Leu Pro Ser His Ala Ser Ile Ile Pro Pro Glu Asp Leu Pro Gly Val
145                 150                 155                 160

Pro Lys Val Phe Val Pro Arg Pro Ser Gln Val Ser Leu Lys Pro Thr
                165                 170                 175

Glu Glu Ala His Lys Lys Glu Arg Lys Pro Gln Lys Pro Gly Lys Tyr
            180                 185                 190

Ile Cys Gln Tyr Cys Ser Arg Pro Cys Ala Lys Pro Ser Val Leu Gln
        195                 200                 205

Lys His Ile Arg Ser His Thr Gly Glu Arg Pro Tyr Pro Cys Gly Pro
    210                 215                 220

Cys Gly Phe Ser Phe Lys Thr Lys Ser Asn Leu Tyr Lys His Arg Lys
225                 230                 235                 240

Ser His Ala His Arg Ile Lys Ala Gly Leu Ala Ser Gly Met Gly Gly
                245                 250                 255

Glu Met Tyr Pro His Gly Leu Glu Met Glu Arg Ile Pro Gly Glu Glu
            260                 265                 270

Phe Glu Glu Pro Thr Glu Gly Glu Ser Thr Asp Ser Glu Glu Thr
        275                 280                 285

Ser Ala Thr Ser Gly His Pro Ala Glu Leu Ser Pro Arg Pro Lys Gln
    290                 295                 300

Pro Leu Leu Ser Ser Gly Leu Tyr Ser Ser Gly Ser His Ser Ser Ser
305                 310                 315                 320

His Glu Arg Cys Ser Leu Ser Gln Ser Ser Thr Ala Gln Ser Leu Glu
                325                 330                 335

Asp Pro Pro Pro Phe Val Glu Pro Ser Ser Glu His Pro Leu Ser His
            340                 345                 350

Lys Pro Glu Asp Thr His Thr Ile Lys Gln Lys Leu Ala Leu Arg Leu
        355                 360                 365

Ser Glu Arg Lys Lys Val Ile Asp Glu Gln Ala Phe Leu Ser Pro Gly
    370                 375                 380

Ser Lys Gly Ser Thr Glu Ser Gly Tyr Phe Ser Arg Ser Glu Ser Ala
385                 390                 395                 400

Glu Gln Gln Val Ser Pro Pro Asn Thr Asn Ala Lys Ser Tyr Ala Glu
                405                 410                 415

Ile Ile Phe Gly Lys Cys Gly Arg Ile Gly Gln Arg Thr Ala Met Leu
            420                 425                 430

Thr Ala Thr Ser Thr Gln Pro Leu Leu Pro Leu Ser Thr Glu Asp Lys
        435                 440                 445

Pro Ser Leu Val Pro Leu Ser Val Pro Arg Thr Gln Val Ile Glu His
    450                 455                 460

Ile Thr Lys Leu Ile Thr Ile Asn Glu Ala Val Val Asp Thr Ser Glu
```

```
              465                 470                 475                 480
Ile Asp Ser Val Lys Pro Arg Ser Ser Leu Ser Arg Arg Ser Ser
                    485                 490                 495

Met Glu Ser Pro Lys Ser Ser Leu Tyr Arg Glu Pro Leu Ser Ser His
                500                 505                 510

Ser Glu Lys Thr Lys Pro Glu Gln Ser Leu Leu Ser Leu Gln His Pro
                515                 520                 525

Pro Ser Thr Ala Pro Pro Val Pro Leu Leu Arg Ser His Ser Met Pro
                530                 535                 540

Ser Ala Ala Cys Thr Ile Ser Thr Pro His His Pro Phe Arg Gly Ser
545                 550                 555                 560

Tyr Ser Phe Asp Asp His Ile Thr Asp Ser Glu Ala Leu Ser Arg Ser
                    565                 570                 575

Ser His Val Phe Thr Ser His Pro Arg Met Leu Lys Pro Gln Pro Ala
                580                 585                 590

Ile Glu Leu Pro Leu Gly Gly Glu Tyr Ser Ser Glu Glu Pro Gly Pro
                595                 600                 605

Ser Ser Lys Asp Thr Ala Ser Lys Pro Ser Asp Glu Val Glu Pro Lys
                610                 615                 620

Glu Ser Glu Leu Thr Lys Lys Thr Lys Lys Gly Leu Lys Thr Lys Gly
625                 630                 635                 640

Val Ile Tyr Glu Cys Asn Ile Cys Gly Ala Arg Tyr Lys Lys Arg Asp
                    645                 650                 655

Asn Tyr Glu Ala His Lys Lys Tyr Tyr Cys Ser Glu Leu Gln Ile Ala
                660                 665                 670

Lys Pro Ile Ser Ala Gly Thr His Thr Ser Pro Glu Ala Glu Lys Ser
                675                 680                 685

Gln Ile Glu His Glu Pro Trp Ser Gln Met Met His Tyr Lys Leu Gly
                690                 695                 700

Thr Thr Leu Glu Leu Thr Pro Leu Arg Lys Arg Lys Glu Lys Ser
705                 710                 715                 720

Leu Gly Asp Glu Glu Glu Pro Ala Phe Glu Ser Thr Lys Ser Gln
                    725                 730                 735

Phe Gly Ser Pro Gly Pro Ser Asp Ala Ala Arg Asn Leu Pro Leu Glu
                740                 745                 750

Ser Thr Lys Ser Pro Ala Glu Pro Ser Lys Ser Val Pro Ser Leu Glu
                755                 760                 765

Gly Pro Thr Gly Phe Gln Pro Arg Thr Pro Lys Pro Gly Ser Gly Ser
                770                 775                 780

Glu Ser Gly Lys Glu Arg Arg Thr Thr Ser Lys Glu Ile Ser Val Ile
785                 790                 795                 800

Gln His Thr Ser Ser Phe Glu Lys Ser Asp Ser Leu Glu Gln Pro Ser
                    805                 810                 815

Gly Leu Glu Gly Glu Asp Lys Pro Leu Ala Gln Phe Pro Ser Pro Pro
                820                 825                 830

Pro Ala Pro His Gly Arg Ser Ala His Ser Leu Gln Pro Lys Leu Val
                835                 840                 845

Arg Gln Pro Asn Ile Gln Val Pro Glu Ile Leu Val Thr Glu Glu Pro
                850                 855                 860

Asp Arg Pro Asp Thr Glu Pro Glu Pro Pro Lys Glu Pro Glu Lys
865                 870                 875                 880

Thr Glu Glu Phe Gln Trp Pro Gln Arg Ser Gln Thr Leu Ala Gln Leu
                    885                 890                 895
```

```
Pro Ala Glu Lys Ala Pro Pro Lys Lys Lys Arg Leu Arg Leu Ala Glu
            900                 905                 910

Met Ala Gln Ser Ser Gly Glu Ser Ser Phe Glu Ser Ser Val Pro Leu
            915                 920                 925

Ser Arg Ser Pro Ser Gln Glu Ser Asn Val Ser Leu Ser Gly Ser Ser
            930                 935                 940

Arg Ser Ala Ser Phe Glu Arg Asp Asp His Gly Lys Ala Glu Ala Pro
945                 950                 955                 960

Asp Pro Ser Ser Asp Met Arg Pro Lys Pro Leu Gly Thr His Met Leu
            965                 970                 975

Thr Val Pro Ser His His Pro His Ala Arg Glu Met Arg Arg Ser Ala
            980                 985                 990

Ser Glu Gln Ser Pro Asn Val Ser His Ser Ala His Met Thr Glu Thr
            995                 1000                1005

Arg Ser Lys Ser Phe Asp Tyr Gly Ser Leu Ser Leu Thr Gly Pro Ser
            1010                1015                1020

Ala Pro Ala Pro Val Ala Pro Ala Gly Glu Ala Pro Glu Arg
1025                1030                1035                1040

Arg Lys Cys Phe Leu Val Arg Ser Pro Ser Leu Ser Arg Pro Pro Glu
            1045                1050                1055

Ser Glu Leu Glu Val Ala Pro Lys Gly Arg Gln Glu Ser Glu Glu Pro
            1060                1065                1070

Gln Pro Ser Ser Ser Lys Pro Ser Ala Lys Ser Ser Leu Ser Gln Ile
            1075                1080                1085

Ser Ser Ala Ala Thr Ser His Gly Gly Pro Pro Gly Gly Lys Gly Pro
            1090                1095                1100

Gly Gln Asp Arg Pro Ala Leu Gly Pro Thr Val Pro Tyr Thr Glu Ala
1105                1110                1115                1120

Leu Gln Val Phe His His Pro Val Ala Gln Thr Pro Leu His Glu Lys
            1125                1130                1135

Pro Tyr Leu Pro Pro Pro Val Ser Leu Phe Ser Phe Gln His Leu Val
            1140                1145                1150

Gln His Glu Pro Gly Gln Ser Pro Glu Phe Phe Ser Thr Gln Ala Met
            1155                1160                1165

Ser Ser Leu Leu Ser Ser Pro Tyr Ser Met Pro Pro Leu Pro Pro Ser
            1170                1175                1180

Leu Phe Gln Ala Pro Pro Leu Pro Leu Gln Pro Thr Val Leu His Pro
1185                1190                1195                1200

Gly Gln Leu His Leu Pro Gln Leu Met Pro His Pro Ala Asn Ile Pro
            1205                1210                1215

Phe Arg Gln Pro Pro Ser Phe Leu Pro Met Pro Tyr Pro Thr Ser Ser
            1220                1225                1230

Ala Leu Ser Ser Gly Phe Phe Leu Pro Leu Gln Ser Gln Phe Ala Leu
            1235                1240                1245

Gln Leu Pro Gly Asp Val Glu Ser His Leu Pro Gln Ile Lys Thr Ser
            1250                1255                1260

Leu Ala Pro Leu Ala Thr Gly Ser Ala Gly Leu Ser Pro Ser Gln Glu
1265                1270                1275                1280

Tyr Ser Ser Asp Ile Arg Leu Pro Pro Val Ala Pro Ala Ser Ser
            1285                1290                1295

Ser Ala Pro Thr Ser Ala Pro Pro Leu Ala Leu Pro Ala Cys Pro Asp
            1300                1305                1310
```

-continued

```
Thr Met Val Ser Leu Val Val Pro Val Arg Val Gln Thr Asn Met Pro
    1315                1320                1325
Ser Tyr Gly Ser Ala Met Tyr Thr Thr Leu Ser Gln Ile Leu Val Thr
    1330                1335                1340
Gln Ser Gln Gly Ser Ser Ala Thr Val Ala Leu Pro Lys Phe Glu Glu
1345                1350                1355                1360
Pro Pro Ser Lys Gly Thr Thr Val Cys Gly Ala Asp Val His Glu Val
                1365                1370                1375
Gly Pro Gly Pro Ser Gly Leu Ser Glu Glu Gln Ser Arg Ala Phe Pro
            1380                1385                1390
Thr Pro Tyr Leu Arg Val Pro Val Thr Leu Pro Glu Arg Lys Gly Thr
        1395                1400                1405
Ser Leu Ser Ser Glu Ser Ile Leu Ser Leu Gly Ser Ser Ser Thr
    1410                1415                1420
Ala Gly Gly Ser Lys Arg Val Leu Ser Pro Ala Gly Ser Leu Glu Leu
1425                1430                1435                1440
Thr Met Glu Thr Gln Gln Gln Lys Arg Val Lys Glu Glu Ala Ser
                1445                1450                1455
Lys Ala Asp Glu Lys Leu Glu Leu Val Lys Pro Cys Ser Val Val Leu
            1460                1465                1470
Thr Ser Thr Glu Asp Gly Lys Arg Pro Glu Lys Ser His Leu Gly Asn
        1475                1480                1485
Gln Gly Gln Gly Arg Arg Glu Leu Glu Met Leu Ser Ser Leu Ser Ser
    1490                1495                1500
Asp Pro Ser Asp Thr Lys Glu Ile Pro Pro Leu Pro His Pro Ala Leu
1505                1510                1515                1520
Ser His Gly Gln Ala Pro Gly Ser Glu Ala Leu Lys Glu Tyr Pro Gln
                1525                1530                1535
Pro Ser Gly Lys Pro His Arg Arg Gly Leu Thr Pro Leu Ser Val Lys
            1540                1545                1550
Lys Glu Asp Ser Lys Glu Gln Pro Asp Leu Pro Ser Leu Ala Pro Pro
        1555                1560                1565
Ser Ser Leu Pro Leu Ser Glu Thr Ser Arg Pro Ala Lys Ser Gln
    1570                1575                1580
Glu Gly Thr Asp Ser Lys Lys Val Leu Gln Phe Pro Ser Leu His Thr
1585                1590                1595                1600
Thr Thr Asn Val Ser Trp Cys Tyr Leu Asn Tyr Ile Lys Pro Asn His
                1605                1610                1615
Ile Gln His Ala Asp Arg Arg Ser Ser Val Tyr Ala Gly Trp Cys Ile
            1620                1625                1630
Ser Leu Tyr Asn Pro Asn Leu Pro Gly Val Ser Thr Lys Ala Ala Leu
        1635                1640                1645
Ser Leu Leu Arg Ser Lys Gln Lys Val Ser Lys Glu Thr Tyr Thr Met
    1650                1655                1660
Ala Thr Ala Pro His Pro Glu Ala Gly Arg Leu Val Pro Ser Ser Ser
1665                1670                1675                1680
Arg Lys Pro Arg Met Thr Glu Val His Leu Pro Ser Leu Val Ser Pro
                1685                1690                1695
Glu Gly Gln Lys Asp Leu Ala Arg Val Glu Lys Glu Glu Arg Arg
            1700                1705                1710
Gly Glu Pro Glu Glu Asp Ala Pro Ala Ser Gln Arg Gly Glu Pro Ala
        1715                1720                1725
Arg Ile Lys Ile Phe Glu Gly Gly Tyr Lys Ser Asn Glu Glu Tyr Val
```

```
                1730                1735                1740
Tyr Val Arg Gly Arg Gly Arg Gly Lys Tyr Val Cys Glu Glu Cys Gly
1745                1750                1755                1760

Ile Arg Cys Lys Lys Pro Ser Met Leu Lys Lys His Ile Arg Thr His
                1765                1770                1775

Thr Asp Val Arg Pro Tyr Val Cys His Cys His Phe Ala Phe Lys
                1780                1785                1790

Thr Lys Gly Asn Leu Thr Lys His Met Lys Ser Lys Ala His Ser Lys
                1795                1800                1805

Lys Cys Gln Glu Thr Gly Val Leu Glu Glu Leu Glu Ala Glu Glu Gly
                1810                1815                1820

Thr Ser Asp Asp Leu Phe Gln Asp Ser Glu Gly Arg Glu Gly Ser Glu
1825                1830                1835                1840

Ala Val Glu Glu His Gln Phe Ser Asp Leu Glu Asp Ser Asp Ser Asp
                1845                1850                1855

Ser Asp Leu Asp Glu Asp Glu Asp Glu Asp Glu Glu Ser Gln Asp
                1860                1865                1870

Glu Leu Ser Arg Pro Ser Ser Glu Ala Pro Pro Gly Pro Pro His
                1875                1880                1885

Ala Leu Arg Ala Asp Ser Ser Pro Ile Leu Gly Pro Gln Pro Pro Asp
                1890                1895                1900

Ala Pro Ala Ser Gly Thr Glu Ala Thr Arg Gly Ser Ser Val Ser Glu
1905                1910                1915                1920

Ala Glu Arg Leu Thr Ala Ser Ser Cys Ser Met Ser Ser Gln Ser Met
                1925                1930                1935

Pro Gly Leu Pro Trp Leu Gly Pro Ala Pro Leu Gly Ser Val Glu Lys
                1940                1945                1950

Asp Thr Gly Ser Ala Leu Ser Tyr Lys Pro Val Ser Pro Arg Arg Pro
                1955                1960                1965

Trp Ser Pro Ser Lys Glu Ala Gly Ser Arg Pro Pro Leu Ala Arg Lys
                1970                1975                1980

His Ser Leu Thr Lys Asn Asp Ser Ser Pro Gln Arg Cys Ser Pro Ala
1985                1990                1995                2000

Arg Glu Pro Gln Ala Ser Ala Pro Ser Pro Gly Leu His Val Asp
                2005                2010                2015

Pro Gly Arg Gly Met Gly Pro Leu Pro Cys Gly Ser Pro Arg Leu Gln
                2020                2025                2030

Leu Ser Pro Leu Thr Leu Cys Pro Leu Gly Arg Glu Leu Ala Pro Arg
                2035                2040                2045

Ala His Val Leu Ser Lys Leu Glu Gly Thr Thr Asp Pro Gly Leu Pro
                2050                2055                2060

Arg Tyr Ser Pro Thr Arg Arg Trp Ser Pro Gly Gln Ala Glu Ser Pro
2065                2070                2075                2080

Pro Arg Ser Ala Pro Pro Gly Lys Trp Ala Leu Ala Gly Pro Gly Ser
                2085                2090                2095

Pro Ser Ala Gly Glu His Gly Pro Gly Leu Gly Leu Ala Pro Arg Val
                2100                2105                2110

Leu Phe Pro Pro Ala Pro Leu Pro His Lys Leu Leu Ser Arg Ser Pro
                2115                2120                2125

Glu Thr Cys Ala Ser Pro Trp Gln Lys Ala Glu Ser Arg Ser Pro Ser
                2130                2135                2140

Cys Ser Pro Gly Pro Ala His Pro Leu Ser Ser Arg Pro Phe Ser Ala
2145                2150                2155                2160
```

```
Leu His Asp Phe His Gly His Ile Leu Ala Arg Thr Glu Glu Asn Ile
            2165                2170                2175

Phe Ser His Leu Pro Leu His Ser Gln His Leu Thr Arg Ala Pro Cys
        2180                2185                2190

Pro Leu Ile Pro Ile Gly Gly Ile Gln Met Val Gln Ala Arg Pro Gly
    2195                2200                2205

Ala His Pro Thr Leu Leu Pro Gly Pro Thr Ala Ala Trp Val Ser Gly
        2210                2215                2220

Phe Ser Gly Gly Gly Ser Asp Leu Thr Gly Ala Arg Glu Ala Gln Glu
2225            2230                2235                2240

Arg Gly Arg Trp Ser Pro Thr Glu Ser Ser Ser Ala Ser Val Ser Pro
            2245                2250                2255

Val Ala Lys Val Ser Lys Phe Thr Leu Ser Ser Glu Leu Glu Gly Arg
        2260                2265                2270

Asp Tyr Pro Lys Glu Arg Glu Arg Thr Gly Gly Pro Gly Arg Pro
    2275                2280                2285

Pro Asp Trp Thr Pro His Gly Thr Gly Ala Pro Ala Glu Pro Thr Pro
    2290                2295                2300

Thr His Ser Pro Cys Thr Pro Pro Asp Thr Leu Pro Arg Pro Pro Gln
2305            2310                2315                2320

Gly Arg Arg Ala Ala Gln Ser Trp Ser Pro Arg Leu Glu Ser Pro Arg
            2325                2330                2335

Ala Pro Ala Asn Pro Glu Pro Ser Ala Thr Pro Pro Leu Asp Arg Ser
        2340                2345                2350

Ser Ser Val Gly Cys Leu Ala Glu Ala Ser Ala Arg Phe Pro Ala Arg
            2355                2360                2365

Thr Arg Asn Leu Ser Gly Glu Ser Arg Thr Arg Gln Asp Ser Pro Lys
        2370                2375                2380

Pro Ser Gly Ser Gly Glu Pro Arg Ala His Pro His Gln Pro Glu Asp
2385            2390                2395                2400

Arg Val Pro Pro Asn Ala
            2405

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
caagaatcca aactcaccag                                             20

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tagcaaccat acattcaaca a                                           21

<210> SEQ ID NO 5
<211> LENGTH: 22
<212> TYPE: DNA
<213> ORGANISM: Artificial Sequence
<220> FEATURE:
```

-continued

```
<223> OTHER INFORMATION: Synthetic oligonucleotide

<400> SEQUENCE: 5
ctccaataca gaattcaagg gc                                               22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 6
tttaggttgg ccagtgtgtg tg                                               22

<210> SEQ ID NO 7
<211> LENGTH: 852
<212> TYPE: PRT
<213> ORGANISM: Homo sapiens

<400> SEQUENCE: 7

Pro Ser Val Leu Gln Lys His Ile Arg Ser His Thr Gly Glu Arg Pro
 1               5                  10                  15

Tyr Pro Cys Gly Pro Cys Gly Phe Ser Phe Lys Thr Lys Ser Asn Leu
            20                  25                  30

Tyr Lys His Arg Lys Ser His Ala His Arg Ile Lys Ala Gly Leu Ala
        35                  40                  45

Ser Gly Met Gly Gly Glu Met Tyr Pro His Gly Leu Glu Met Glu Arg
    50                  55                  60

Ile Pro Gly Glu Glu Phe Glu Glu Pro Thr Glu Gly Glu Ser Thr Asp
65                  70                  75                  80

Ser Glu Glu Glu Thr Ser Ala Thr Ser His Pro Ala Glu Leu Ser
                85                  90                  95

Pro Arg Pro Lys Gln Pro Leu Leu Ser Ser Gly Leu Tyr Ser Ser Gly
            100                 105                 110

Ser His Ser Ser His Glu Arg Cys Ser Leu Ser Gln Ser Ser Thr
        115                 120                 125

Ala Gln Ser Leu Glu Asp Pro Pro Phe Val Glu Pro Ser Ser Glu
    130                 135                 140

His Pro Leu Ser His Lys Pro Glu Asp Thr His Thr Ile Lys Gln Lys
145                 150                 155                 160

Leu Ala Leu Arg Leu Ser Glu Arg Lys Lys Val Ile Asp Glu Gln Ala
                165                 170                 175

Phe Leu Ser Pro Gly Ser Lys Gly Ser Thr Glu Ser Gly Tyr Phe Ser
            180                 185                 190

Arg Ser Glu Ser Ala Glu Gln Gln Val Ser Pro Pro Asn Thr Asn Ala
        195                 200                 205

Lys Ser Tyr Ala Glu Ile Ile Phe Gly Lys Cys Gly Arg Ile Gly Gln
    210                 215                 220

Arg Thr Ala Met Leu Thr Ala Thr Ser Thr Gln Pro Leu Leu Pro Leu
225                 230                 235                 240

Ser Thr Glu Asp Lys Pro Ser Leu Val Pro Leu Ser Val Pro Arg Thr
                245                 250                 255

Gln Val Ile Glu His Ile Thr Lys Leu Ile Thr Ile Asn Glu Ala Val
            260                 265                 270

Val Asp Thr Ser Glu Ile Asp Ser Val Lys Pro Arg Arg Ser Ser Leu
        275                 280                 285
```

```
Ser Arg Arg Ser Ser Met Glu Ser Pro Lys Ser Ser Leu Tyr Arg Glu
    290                 295                 300

Pro Leu Ser Ser His Ser Glu Lys Thr Lys Pro Glu Gln Ser Leu Leu
305                 310                 315                 320

Ser Leu Gln His Pro Pro Ser Thr Ala Pro Pro Val Pro Leu Leu Arg
                325                 330                 335

Ser His Ser Met Pro Ser Ala Ala Cys Thr Ile Ser Thr Pro His His
        340                 345                 350

Pro Phe Arg Gly Ser Tyr Ser Phe Asp Asp His Ile Thr Asp Ser Glu
            355                 360                 365

Ala Leu Ser Arg Ser Ser His Val Phe Thr Ser His Pro Arg Met Leu
    370                 375                 380

Lys Pro Gln Pro Ala Ile Glu Leu Pro Leu Gly Gly Glu Tyr Ser Ser
385                 390                 395                 400

Glu Glu Pro Gly Pro Ser Ser Lys Asp Thr Ala Ser Lys Pro Ser Asp
                405                 410                 415

Glu Val Glu Pro Lys Glu Ser Glu Leu Thr Lys Lys Thr Lys Lys Gly
            420                 425                 430

Leu Lys Thr Lys Gly Val Ile Tyr Glu Cys Asn Ile Cys Gly Ala Arg
    435                 440                 445

Tyr Lys Lys Arg Asp Asn Tyr Glu Ala His Lys Lys Tyr Tyr Cys Ser
    450                 455                 460

Glu Leu Gln Ile Ala Lys Pro Ile Ser Ala Gly Thr His Thr Ser Pro
465                 470                 475                 480

Glu Ala Glu Lys Ser Gln Ile Glu His Glu Pro Trp Ser Gln Met Met
                485                 490                 495

His Tyr Lys Leu Gly Thr Thr Leu Glu Leu Thr Pro Leu Arg Lys Arg
            500                 505                 510

Arg Lys Glu Lys Ser Leu Gly Asp Glu Glu Pro Ala Phe Glu
    515                 520                 525

Ser Thr Lys Ser Gln Phe Gly Ser Pro Gly Pro Ser Asp Ala Ala Arg
    530                 535                 540

Asn Leu Pro Leu Glu Ser Thr Lys Ser Pro Ala Glu Pro Ser Lys Ser
545                 550                 555                 560

Val Pro Ser Leu Glu Gly Pro Thr Gly Phe Gln Pro Arg Thr Pro Lys
                565                 570                 575

Pro Gly Ser Gly Ser Glu Ser Gly Lys Glu Arg Arg Thr Thr Ser Lys
            580                 585                 590

Glu Ile Ser Val Ile Gln His Thr Ser Ser Phe Glu Lys Ser Asp Ser
    595                 600                 605

Leu Glu Gln Pro Ser Gly Leu Glu Gly Glu Asp Lys Pro Leu Ala Gln
    610                 615                 620

Phe Pro Ser Pro Pro Ala Pro His Gly Arg Ser Ala His Ser Leu
625                 630                 635                 640

Gln Pro Lys Leu Val Arg Gln Pro Asn Ile Gln Val Pro Glu Ile Leu
                645                 650                 655

Val Thr Glu Glu Pro Asp Arg Pro Asp Thr Glu Pro Glu Pro Pro
            660                 665                 670

Lys Glu Pro Glu Lys Thr Glu Glu Phe Gln Trp Pro Gln Arg Ser Gln
    675                 680                 685

Thr Leu Ala Gln Leu Pro Ala Glu Lys Ala Pro Pro Lys Lys Lys Arg
    690                 695                 700
```

```
Leu Arg Leu Ala Glu Met Ala Gln Ser Ser Gly Glu Ser Ser Phe Glu
705                 710                 715                 720

Ser Ser Val Pro Leu Ser Arg Ser Pro Ser Gln Glu Ser Asn Val Ser
            725                 730                 735

Leu Ser Gly Ser Ser Arg Ser Ala Ser Phe Glu Arg Asp Asp His Gly
        740                 745                 750

Lys Ala Glu Ala Pro Asp Pro Ser Ser Asp Met Arg Pro Lys Pro Leu
            755                 760                 765

Gly Thr His Met Leu Thr Val Pro Ser His His Pro His Ala Arg Glu
    770                 775                 780

Met Arg Arg Ser Ala Ser Glu Gln Ser Pro Asn Val Ser His Ser Ala
785                 790                 795                 800

His Met Thr Glu Thr Arg Ser Lys Ser Phe Asp Tyr Gly Ser Leu Ser
                805                 810                 815

Leu Thr Gly Pro Ser Ala Pro Ala Pro Val Ala Pro Pro Ala Gly Glu
            820                 825                 830

Ala Pro Pro Glu Arg Arg Lys Cys Phe Leu Val Arg Ser Pro Ser Leu
        835                 840                 845

Ser Arg Pro Pro
    850

<210> SEQ ID NO 8
<211> LENGTH: 786
<212> TYPE: PRT
<213> ORGANISM: Homo sapiens

<400> SEQUENCE: 8

Glu Met Leu Ser Ser Leu Ser Ser Asp Pro Ser Asp Thr Lys Glu Ile
1               5                   10                  15

Pro Pro Leu Pro His Pro Ala Leu Ser His Gly Gln Ala Pro Gly Ser
            20                  25                  30

Glu Ala Leu Lys Glu Tyr Pro Gln Pro Ser Gly Lys Pro His Arg Arg
        35                  40                  45

Gly Leu Thr Pro Leu Ser Val Lys Lys Glu Asp Ser Lys Glu Gln Pro
    50                  55                  60

Asp Leu Pro Ser Leu Ala Pro Pro Ser Ser Leu Pro Leu Ser Glu Thr
65                  70                  75                  80

Ser Ser Arg Pro Ala Lys Ser Gln Glu Gly Thr Asp Ser Lys Lys Val
                85                  90                  95

Leu Gln Phe Pro Ser Leu His Thr Thr Thr Asn Val Ser Trp Cys Tyr
            100                 105                 110

Leu Asn Tyr Ile Lys Pro Asn His Ile Gln His Ala Asp Arg Arg Ser
        115                 120                 125

Ser Val Tyr Ala Gly Trp Cys Ile Ser Leu Tyr Asn Pro Asn Leu Pro
    130                 135                 140

Gly Val Ser Thr Lys Ala Ala Leu Ser Leu Leu Arg Ser Lys Gln Lys
145                 150                 155                 160

Val Ser Lys Glu Thr Tyr Thr Met Ala Thr Ala Pro His Pro Glu Ala
                165                 170                 175

Gly Arg Leu Val Pro Ser Ser Arg Lys Pro Arg Met Thr Glu Val
            180                 185                 190

His Leu Pro Ser Leu Val Ser Pro Glu Gly Gln Lys Asp Leu Ala Arg
        195                 200                 205

Val Glu Lys Glu Glu Glu Arg Arg Gly Glu Pro Glu Glu Asp Ala Pro
    210                 215                 220
```

-continued

```
Ala Ser Gln Arg Gly Glu Pro Ala Arg Ile Lys Ile Phe Glu Gly Gly
225                 230                 235                 240

Tyr Lys Ser Asn Glu Glu Tyr Val Tyr Val Arg Gly Arg Gly Arg Gly
                245                 250                 255

Lys Tyr Val Cys Glu Glu Cys Gly Ile Arg Cys Lys Lys Pro Ser Met
                260                 265                 270

Leu Lys Lys His Ile Arg Thr His Thr Asp Val Arg Pro Tyr Val Cys
                275                 280                 285

Lys His Cys His Phe Ala Phe Lys Thr Lys Gly Asn Leu Thr Lys His
                290                 295                 300

Met Lys Ser Lys Ala His Ser Lys Lys Cys Gln Glu Thr Gly Val Leu
305                 310                 315                 320

Glu Glu Leu Glu Ala Glu Gly Thr Ser Asp Asp Leu Phe Gln Asp
                325                 330                 335

Ser Glu Gly Arg Glu Gly Ser Glu Ala Val Glu Glu His Gln Phe Ser
                340                 345                 350

Asp Leu Glu Asp Ser Asp Ser Asp Leu Asp Glu Asp Glu Asp
                355                 360                 365

Glu Asp Glu Glu Glu Ser Gln Asp Glu Leu Ser Arg Pro Ser Ser Glu
370                 375                 380

Ala Pro Pro Gly Pro Pro His Ala Leu Arg Ala Asp Ser Ser Pro
385                 390                 395                 400

Ile Leu Gly Pro Gln Pro Pro Asp Ala Pro Ala Ser Gly Thr Glu Ala
                405                 410                 415

Thr Arg Gly Ser Ser Val Ser Glu Ala Glu Arg Leu Thr Ala Ser Ser
                420                 425                 430

Cys Ser Met Ser Ser Gln Ser Met Pro Gly Leu Pro Trp Leu Gly Pro
                435                 440                 445

Ala Pro Leu Gly Ser Val Glu Lys Asp Thr Gly Ser Ala Leu Ser Tyr
450                 455                 460

Lys Pro Val Ser Pro Arg Arg Pro Trp Ser Pro Ser Lys Glu Ala Gly
465                 470                 475                 480

Ser Arg Pro Pro Leu Ala Arg Lys His Ser Leu Thr Lys Asn Asp Ser
                485                 490                 495

Ser Pro Gln Arg Cys Ser Pro Ala Arg Glu Pro Gln Ala Ser Ala Pro
                500                 505                 510

Ser Pro Pro Gly Leu His Val Asp Pro Gly Arg Gly Met Gly Pro Leu
                515                 520                 525

Pro Cys Gly Ser Pro Arg Leu Gln Leu Ser Pro Leu Thr Leu Cys Pro
530                 535                 540

Leu Gly Arg Glu Leu Ala Pro Arg Ala His Val Leu Ser Lys Leu Glu
545                 550                 555                 560

Gly Thr Thr Asp Pro Gly Leu Pro Arg Tyr Ser Pro Thr Arg Arg Trp
                565                 570                 575

Ser Pro Gly Gln Ala Glu Ser Pro Arg Ser Ala Pro Gly Lys
                580                 585                 590

Trp Ala Leu Ala Gly Pro Gly Ser Pro Ser Ala Gly Glu His Gly Pro
                595                 600                 605

Gly Leu Gly Leu Ala Pro Arg Val Leu Phe Pro Ala Pro Leu Pro
                610                 615                 620

His Lys Leu Leu Ser Arg Ser Pro Glu Thr Cys Ala Ser Pro Trp Gln
625                 630                 635                 640
```

-continued

```
Lys Ala Glu Ser Arg Ser Pro Ser Cys Ser Pro Gly Pro Ala His Pro
            645             650             655

Leu Ser Ser Arg Pro Phe Ser Ala Leu His Asp Phe His Gly His Ile
            660             665             670

Leu Ala Arg Thr Glu Glu Asn Ile Phe Ser His Leu Pro Leu His Ser
            675             680             685

Gln His Leu Thr Arg Ala Pro Cys Pro Leu Ile Pro Ile Gly Gly Ile
            690             695             700

Gln Met Val Gln Ala Arg Pro Gly Ala His Pro Thr Leu Leu Pro Gly
705             710             715             720

Pro Thr Ala Ala Trp Val Ser Gly Phe Ser Gly Gly Gly Ser Asp Leu
            725             730             735

Thr Gly Ala Arg Glu Ala Gln Glu Arg Gly Arg Trp Ser Pro Thr Glu
            740             745             750

Ser Ser Ser Ala Ser Val Ser Pro Val Ala Lys Val Ser Lys Phe Thr
            755             760             765

Leu Ser Ser Glu Leu Glu Gly Arg Asp Tyr Pro Lys Glu Arg Glu Arg
    770             775             780

Thr Gly
785
```